US011164655B2

(12) United States Patent
Bell et al.

(10) Patent No.: US 11,164,655 B2
(45) Date of Patent: Nov. 2, 2021

(54) SYSTEMS AND METHODS FOR PREDICTING HOMOLOGOUS RECOMBINATION DEFICIENCY STATUS OF A SPECIMEN

(71) Applicant: Tempus Labs, Inc., Chicago, IL (US)

(72) Inventors: Joshua S K Bell, Chicago, IL (US); Catherine Igartua, Chicago, IL (US); Benjamin Leibowitz, Chicago, IL (US)

(73) Assignee: Tempus Labs, Inc., Chicago, IL (US)

( * ) Notice: Subject to any disclaimer, the term of this patent is extended or adjusted under 35 U.S.C. 154(b) by 0 days.

(21) Appl. No.: 17/118,227

(22) Filed: Dec. 10, 2020

(65) Prior Publication Data

US 2021/0172024 A1 Jun. 10, 2021

Related U.S. Application Data

(60) Provisional application No. 62/946,347, filed on Dec. 10, 2019.

(51) Int. Cl.
*G16B 20/00* (2019.01)
*G16B 30/10* (2019.01)
*G16B 5/00* (2019.01)
*G16B 25/10* (2019.01)
*G16B 50/30* (2019.01)
*G16B 30/20* (2019.01)
*C12Q 1/6886* (2018.01)

(52) U.S. Cl.
CPC .............. *G16B 20/00* (2019.02); *G16B 5/00* (2019.02); *G16B 25/10* (2019.02); *G16B 30/10* (2019.02); *G16B 30/20* (2019.02); *G16B 50/30* (2019.02); *C12Q 1/6886* (2013.01); *C12Q 2600/154* (2013.01)

(58) Field of Classification Search
None
See application file for complete search history.

(56) References Cited

U.S. PATENT DOCUMENTS

| 2013/0029926 A1 | 1/2013 | Timms et al. |
| 2017/0283879 A1 | 10/2017 | Abkevich et al. |
| 2018/0030544 A1 | 2/2018 | Abkevich et al. |

FOREIGN PATENT DOCUMENTS

| WO | WO 2017/165270 A1 | 9/2017 |
| WO | WO 2017/178509 A1 | 10/2017 |

OTHER PUBLICATIONS

Abkevich et al. 2012 Patterns of genomic loss of heterozygosity predict homologous recombination repair defects in epithelial ovarian cancer British Journal of Cancer vol. 107, pp. 1776-1782 (Year: 2012).*
Lu et al. Correlation between gene expression and mutator phenotype predicts homologous recombination deficiency and outcome in ovarian cancer Journal of Molecular Medicine vol. 92, pp. 1159-1168 (Year: 2014).*
Subramanian et al. Gene set enrichment analysis: A knowledge-based approach for interpreting genome-wide expression profiles Proceedings of the National Academy of Sciences USA vol. 102, pp. 15545-15550 (Year: 2005).*
Konstantinopoulos et al. Gene Expression Profile of BRCAness That Correlates With Responsiveness to Chemotherapy and With Outcome in Patients With Epithelial Ovarian Cancer Journal of Clinical Oncology vol. 28, pp. 3555-3561 (Year: 2010).*
Tomczaketal. The Cancer Genome Atlas (TCGA) an immeasurable source of knowledge Contemporary Oncology vol. 19, pp. A68-A77 (Year: 2015).*
Kawazu et al. Integrative analysis of genomic alterations in triple-negative breast cancer in association with homologous recombination deficiency PLOS Genetics vol. 13, article e1006853 (Year: 2017).*
Aguilera, Andrés, et al. "Transcription and Recombination: When RNA Meets DNA," Cold Spring Harbor Perspect Biol, 2014, 6:a016543, pp. 17.
Belli, et al. "Homologous recombination deficiency in triple negative breast cancer," The Breast, 45, pp. 15-21 (2019).
Bonadio, et al. "Homologous recombination deficiency in ovarian cancer: a review of its epidemiology and management," Clinics, pp. 1-6 (2018).
Broderick, "BRCA Mutations Linked to Longer Survival in Ovarian Cancer," pp. 1-2.
Caffrey, "Myriad Genetics Submits myChoice HRD as Companion Diagnostic for Niraparib," https://www.ajmc.com/newsroom/myriad-genetics-submits-mychoice-hrd-as-companion-diagnostic-for-niraparib, pp. 1.
Chang, et al. "Homologous recombination deficiency (HRD) by BROCA-HR and survival outcomes after surgery for patients (pts) with pancreatic adenocarcinoma (PC): A single institution experience," Journal of Clinical Oncology, 38, No. 4, pp. 1-3 (Feb. 4, 2020).
Coleman, et al. "Rucaparib maintenance treatment for recurrent ovarian carcinoma after response to platinum therapy (ARIEL3): a randomised, double-blind, placebo-controlled, phase 3 trial," Lancet. Author manuscript; available in PMC, pp. 1-26 (Apr. 16, 2018).
Criscuolo, et al. "New combinatorial strategies to improve the PARP inhibitors efficacy in the urothelial bladder Cancer treatment," Journal of Experimental & Clinical Cancer Research, pp. 1-9 (2019).

(Continued)

*Primary Examiner* — John S Brusca
(74) *Attorney, Agent, or Firm* — Andrew J. Antczak; Brett A. Lovejoy; Morgan, Lewis & Bockius, LLP

(57) ABSTRACT

Methods, systems, and software are provided for an ensemble model trained to distinguish between cancers with homologous recombination pathway deficiencies (HRD positive cancers) and cancers without homologous recombination pathway deficiencies (HRD negative cancers) based on nucleic acid sequencing data, e.g., both RNA and DNA sequencing data, generated from a cancerous tissue sample of the subject.

26 Claims, 40 Drawing Sheets

(12 of 40 Drawing Sheet(s) Filed in Color)

(56) References Cited

OTHER PUBLICATIONS

Davies, et al. "HRDetect is a predictor of BRCA1 and BRCA2 deficiency based on mutational-signatures," Nat. Med., pp. 1-28 (2017).
Fogelman, et al. "Evidence for the Efficacy of Iniparib, a PARP-1 Inhibitor, in BRCA2-associated Pancreatic Cancer," Anticancer Research, 31, pp. 1417-1420 (2011).
Gray, et al. "TumorNext: A comprehensive tumor profiling assay that incorporates high resolution copy number analysis and germline status to improve testing accuracy," www.impactjournals.com/oncotarget/, Oncotarget, vol. 7, No. 42, pp. 68206-68228.
Gulhan, et al. "Detecting the mutational signature of homologous recombination deficiency in clinical samples," nature genetics, vol. 51, pp. 912-922 (May 2019).
Heeke, et al. "Prevalence of Homologous Recombination Deficiency (HRD) Among All Tumor Types," ASCO Annual Meeting '17, pp. 1-20.
Heeke, et al. "Prevalence of Homologous Recombination-Related Gene Mutations Across Multiple Cancer Types," JCO Precis Oncol., pp. 1-18, (2018).
Helfand, "ESMO: AZ, Merck's Lynparza brings precision medicine to prostate cancer with 'game-changer' results," FiercePharma, pp. 1-6 (Sep. 30, 2019).
Hodgson, et al. "Candidate biomarkers of PARP inhibitor sensitivity in ovarian cancer beyond the BRCA genes," British Journal of Cancer, pp. 1401-1409 (2018).
Hoppe, et al. "Biomarkers for Homologous Recombination Deficiency in Cancer," JNCI J Natl Cancer Inst 110 (7), pp. 704-713 (May 18, 2018).
Kausar, et al. "Sensitization of Pancreatic Cancers to Gemcitabine Chemoradiation by WEE1 Kinase Inhibition Depends on Homologous Recombination Repair," Neoplasia, vol. 17, No. 10, pp. 757-766 (Oct. 2015).
Knijnenburg, et al. "Genomic and Molecular Landscape of DNA Damage Repair Deficiency across the Cancer Genome Atlas," Cell Reports, pp. 1-23 (2018).
Longo, "Personalized Medicine for Primary Treatment of Serous Ovarian Cancer," The New England Journal of Medicine, 381, 25, pp. 2471-2474 (Dec. 19, 2019).
Marquard, et al. "Abstract 2822: A pan-cancer analysis of inferred homologous recombination deficiency identifies potential platinum benefit in novel subtypes," American Associate for Cancer Research, pp. 1-4 (Oct. 2014).
Mateo, et al. "DNA-Repair Defects and Olaparib in Metastatic Prostate Cancer," The New England Journal of Medicine, vol. 373, No. 18, pp. 1697-1708 (Oct. 29, 2015).
McDevitt, Shane, et al. "How RNA transcripts coordinate DNA recombination and repair," Nature Communications, 2018, 9:1091, pp. 10.
Mirza, et al. "Niraparib Maintenance Therapy in Platinum-Sensitive, Recurrent Ovarian Cancer," The New England Journal of Medicine, pp. 2154-2164 (Oct. 8, 2016).
Naipal, et al. "Functional Ex Vivo Assay to Select Homologous Recombination-Deficient Breast Tumors for PARP Inhibitor Treatment," Clinical Cancer Research, pp. 4816-4827 (Sep. 15, 2014).
Nguyen, et al. "Pan-cancer landscape of homologous recombination deficiency," bioRxiv, http://dx.doi.org/10.1101/2020.01.13.905026, pp. 1-32 (Jan. 14, 2020).
O'Kane, et al. "Homologous recombination deficiency (HRD) scoring in pancreatic ductal adenocarcinoma (PDAC) and response to chemotherapy," Journal of Clinical Oncology, 38, pp. 1-2 (Feb. 1, 2020).
Peng, Guang, et al. "Genome-wide Transcriptome Profiling of Homologous Recombination DNA Repair," Nat Commun. Author manuscript, Jul. 1, 2014, pp. 21.
Pokataev, et al. "Efficacy of platinum-based chemotherapy and prognosis of patients with pancreatic cancer with homologous recombination deficiency: comparative analysis of published clinical studies," ESMO Open Cancer Horizons, pp. 1-8 (Jan. 29, 2020).
Stronach, "Biomarker Assessment of HR Deficiency, Tumor BRCA1/2 Mutations, and CNE1 Copy Number in Ovarian Cancer: Associations with Clinical Outcome Following Platinum Monotherapy," American Association for Cancer Research, pp. 1103-1112 (2018).
Sztupinszki, et al. "Detection of molecular signatures of homologous recombination deficiency in prostate cancer with or without BRCA1/2 mutations Running title: Homologous recombination deficiency in prostate cancer," Clinical Cancer Research, pp. 1-29 (Feb. 18, 2020).
Takaya, et al. "Homologous recombination deficiency status-based classification of high-grade serous ovarian carcinoma," Scientific Reports, pp. 1-8 (2020).
Teo, et al. "Is it time to split strategies to treat homologous recombinant deficiency in pancreas cancer?", Journal of Gastrointestinal Oncology, pp. 738-749 (2016).
Telli, et al. "Homologous Recombination Deficiency (HRD) Score Predicts Response to Platinum-Containing Neoadjuvant Chemotherapy in Patients with Triple-Negative Breast Cancer," Clinical Cancer Research, 22(15), pp. 3764-3774 (Aug. 1, 2016).
Timms, et al. "Association of BRCA1/2 defects with genomic scores predictive of DNA damage repair deficiency among breast cancer subtypes," Breast Cancer Research, pp. 1-9 (2014).
Vencken, et al. "Chemosensitivity and outcome of BRCA1- and BRCA2- associated ovarian cancer patients after first-line chemotherapy compared with sporadic ovarian cancer patients," Annals of Oncology 22: pp. 1346-1352 (2011).
Zhao, et al. "Homologous Recombination Deficiency and Platinum-Based Therapy Outcomes in Advanced Breast Cancer," Clinical Cancer Research, pp. 7521-7531 (Dec. 15, 2017).
A Phase I/II Study of MED14736 in Combination With Olaparib in Patients With Advanced Solid Tumors (MEDIOLA), U.S. National Library of Medicine, pp. 1-11.
A Study to Evaluate Rucaparib in Combination With Other Anticancer Agents in Patients With a Solid Tumor (SEASTAR), U.S. National Library of Medicine, pp. 1-6.
A Study of Durvalumab Alone and Durvalumab+Olaparib in Advanced, Platinum-Ineligible Bladder Cancer (BAYOU) (BAYOU), U.S. National Library of Medicine, pp. 1-8.
BeiGene Announces Clinical Data on Tislelizumab and Pamiparib Presented at the European Society for Medical Oncology (ESMO) Congress 2019, BeiGene, pp. 1-4 (Sep. 30, 2-19).
Breakthrough From PAOLA1 GINECO/ENGOT-OV25 Trial: Adding Olaparib to Bevacizumab Maintenance Demonstrates Substantial Clinical Benefit in Newly Diagnosed Advanced Ovarian Cancer, ESMO, pp. 1-3 (Sep. 28, 2019).
Draft FoundationFocus CDxBRCA LOH Technical Information Summary, pp. 1-27.
ESMO 2019—Clovis is running out of waves to catch, Vantage, pp. 1-3 (Oct. 1, 2019).
ESMO 2019: Pre-Specified Interim Analysis of GALAHAD: A Phase 2 Study of Niraparib in Patients with mCRPC and Biallelic DNA-Repair Gene Defects, pp. 1-3.
ESMO 2019: Preliminary Results from the TRITON2 Study of Rucaparib in Patients with Dna Damage Repair-deficient mCRPC: Updated Analyses, pp. 1-4.
FoundationFocus CDxBRCA LOH—P160018/S001, pp. 1-2.
FoundationOne CDx—Technical Information, pp. 1-45.
FoundationOneLiquid FoundationOne Liquid is our next-generation liquid biopsy test for solid tumors utilizing circulating tumor DNA (ctDNA), pp. 1-5.
Incorporating Veliparib Into Chemotherapy and Continuing With Veliparib Maintenance Significantly Improved PFS in Newly Diagnosed High-Grade Serous Ovarian Cancer, ESMO, pp. 1-3 (Sep. 28, 2019).
Label: Lynparza—olaparib tablet, film coated, pp. 1-42 (Dec. 27, 2019).
List of Cleared or Approved Companion Diagnostic Devices (In Vitro and Imaging Tools), pp. 1-8.
Lynparza achieved a 72% objective response rate in patients with relapsed, germline BRCAmutated advanced ovarian cancer, pp. 1-4 (Jun. 3, 2019).
MyChoice CDx®—Technical Information, bit.ly/myChoiceCDxSpecs, pp. 1-17.

(56) References Cited

OTHER PUBLICATIONS

Myriad Genetics myChoice HRD® Update, pp. 1-24 (Jun. 30, 2016).
Myriad myChoice® HRD—Technical Specifications, (2017) pp. 1-3.
Myriad Files sPMA With FDA for Test to ID Best Responders to Lynparza, Avastin Combination, genomeweb, pp. 1-2 (Feb. 11, 2020).
Niraparib Prolongs PFS in Patients With Newly Diagnosed Advanced Ovarian Cancer, ESMO, pp. 1-3 (Sep. 28, 2019).
Phase III PROfound Study Evaluates Olaparib in Setting of Metastatic, Castration-Resistant Prostate Cancer, ESMO, pp. 1-5 (Nov. 10, 2019).
Tesaro'S Niraparib Significantly Improved Progression-Free Survival, The Clearity Foundation, pp. 1-5.
Tesaro Announces Expansion to Second Stage of JASPER Trial of Zejula® in Combination With TSR-042 in Non-Small Cell Lung Cancer, pp. 1-5 (Sep. 10, 2018).
Test Requisition Form, Foundation Medicine, pp. 1-2.
Test Request Form, Myriad myChoice CDx, pp. 1-2.
The Importance of HRD Testing, oncology,specialty pharmacy,HSE,hrd testing, pp. 1-2.
The role of PARP-1 in the repair of single stranded break (SSB), Novus Biologicals a biotechne brand, pp. 1-2 (Apr. 22, 2016).
TumorNext—HRD, Ambry Genetics, pp. 1-3.
TumorNext—HRD: Paired Germline and Tumor Analyses of Genes Associated with Hereditary Ovarian Cancer, Sample Report, Ambry Genetics, pp. 1-7.
Tumor Test Requisition Form, Ambry Genetics, pp. 1-2.
What is Myriad myChoice CDx? Myriad myChoice CDx, https://bit.ly/myChoiceCDxSpecs, pp. 1-5.
Ha, Gavin, et al. "Integrative analysis of genome-wide loss of heterozygosity and mono-allelic expression at nucleotide resolution reveals disrupted pathways in triple negative breast cancer", http://genome.cship.org/subscriptions, Cold Spring Harbor Laboratory Press, May 21, 2012, pp. 1-38.

* cited by examiner

Test subject database 120
- Test subject 1 122-1
  - Biographical data 124-1
    - Cancer type 125-1-a
    - Personal characteristics 125-1-b
    - Medical history 125-1-c
    - Clinical features 125-1-d
  - Cancer tissue DNA Sequencing data 126-1
    - DNA sequencing run 1 127-1-1
      - Sequence read 1 128-1-1-1
      - ⋮
      - Sequence read K 128-1-1-K
      - Aligned sequences (e.g., BAM file) 129-1-1
    - ⋮
    - DNA sequencing run L 127-1-L
  - Normal tissue DNA Sequencing data 130-1
    - DNA sequencing run 1 131-1-1
      - Sequence read 1 132-1-1-1
      - ⋮
      - Sequence read K 132-1-1-M
      - Aligned sequences (e.g., BAM file) 133-1-1
    - ⋮
    - DNA sequencing run L 131-1-N
  - RNA Sequencing data 134-1
    - RNA sequencing run 1 135-1-1
      - Sequence read 1 136-1-1-1
      - ⋮
      - Sequence read O 136-1-1-O
      - Aligned sequences (e.g., BAM file) 137-1-1
      - Expression data 138-1-1
    - ⋮
    - RNA sequencing run P 135-1-P
  - Ensemble classifier outputs 140-1
- ⋮
- Test subject Q 122-Q Non-persistent memory 111

FIG. 1B

| | |
|---|---|
| Non-persistent memory 111 | Test subject database 120 |

| Test subject database 120 |
|---|
| Test subject 1 122-1 |
|   Biographical data 124-1 |
|   Cancer tissue DNA sequencing data 126-1 |
|   Normal tissue DNA sequencing data 130-1 |
|   RNA sequencing data 134-1 |
|   Ensemble classifier outputs 140-1 |
|     HRD determination 1 141-1-1 |
|       Gene expression model score 142-1-1 |
|       Methylation model score 143-1-1 |
|       gwLOH model score 144-1-1 |
|       Gene rearrangement model score 145-1-1 |
|       ssGSEA model score 146-1-1 |
|       HRD ensemble model score 147-1-1 |
|     ⋮ |
|     HRD determination R 141-1-R |
| ⋮ |
| Test subject Q 122-Q |

FIG. 1C

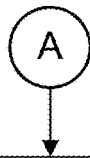

514 Generate a subject data construct including:
(i) the first prediction for the homologous recombination pathway status of the cancerous tissue of the subject and
(ii) the second prediction for the homologous recombination pathway status of the cancerous tissue of the subject.

516 (Continued) The subject data construct further includes:
iii) the third prediction for the homologous recombination pathway status of the cancerous tissue of the subject.

518 (Continued) The subject data construct further includes:
iii) the third prediction for the homologous recombination pathway status of the cancerous tissue of the subject.

522 (Continued) The subject data construct further includes:
iv) the fourth prediction for the homologous recombination pathway status of the cancerous tissue of the subject.

520 (Continued) The subject data construct further includes:
iv) the one or more methylation scores for the cancerous tissue.

528 Input the subject data construct into an ensemble model trained to distinguish between cancers with homologous recombination pathway deficiencies and cancers without homologous recombination pathway deficiencies, thus determining the homologous recombination pathway status of the test subject.

530 When it is determined that the cancer in the test subject is homologous recombination deficient, treat the cancer by administering a poly ADP ribose polymerase (PARP) inhibitor to the test subject.

When it is determined the cancer in the test subject is not homologous recombination deficient, treat the cancer with a therapy that does not include administration of a PARP inhibitor to the test subject.

FIG. 5C

HRD STATUS

GENOME-WIDE LOH

Your patient's Genome-wide LOH: 50%

GENOMIC VARIANTS

Genes analyzed for HRD status include ATM, BARD1, BRIP1, CHEK2, MRE11A, NBN, PALB2, RAD51C, RAD51D, BRCA1, BRCA2, and [list not finalized].

| Genomic Variants | | Details |
|---|---|---|
| ATM | p.F1774fs - LOF | 29% VAF |
| BRCA1 | p.L79P | Germline |

ZEJULA® (niraparib) is a PARP inhibitor indicated for the treatment of adult patients with advanced ovarian, fallopian tube, or primary peritoneal cancer who have been treated with three or more prior chemotherapy regimens and whose cancer is associated with HRD positive status as determined by an FDA-approved test. HRD positive status is defined by either a deleterious or suspected deleterious BRCA mutation, or genomic instability and who have progressed more than six months after response to the last platinum-based chemotherapy.

FIG. 6C

| Cancer | Data | Alpha | N Samples | MAE | RMSE | Cor (Pearson) | Cor (Spearman) | N Genes |
|---|---|---|---|---|---|---|---|---|
| BRCA | Testing | 0.25 | 228 | 7.11 | 9.65 | 0.87 | 0.86 | 388 |
| BRCA | Training | 0.25 | 684 | 6.07 | 7.92 | 0.93 | 0.92 | 388 |
| UCEC | Testing | 0.25 | 40 | 9.3 | 11.51 | 0.83 | 0.85 | 167 |
| UCEC | Training | 0.25 | 120 | 6.58 | 8.45 | 0.95 | 0.89 | 167 |
| BLCA | Testing | 0.25 | 92 | 10.38 | 12.57 | 0.82 | 0.82 | 357 |
| BLCA | Training | 0.25 | 276 | 8.18 | 10.49 | 0.84 | 0.85 | 357 |
| STAD | Testing | 0.25 | 77 | 12.06 | 13.77 | 0.77 | 0.74 | 59 |
| STAD | Training | 0.25 | 228 | 11.05 | 13.64 | 0.83 | 0.85 | 59 |
| SARC | Testing | 0.25 | 54 | 8.9 | 11.73 | 0.76 | 0.78 | 112 |
| SARC | Training | 0.25 | 159 | 7.85 | 9.66 | 0.93 | 0.93 | 112 |

FIG. 8

| data_type | model | y_test | y_pred | y_pred_proba | fold | f3_score |
|---|---|---|---|---|---|---|
| fusions | fusions | 0.024409 | 0.259014 | 0.371031 | 1.998010 | 0.348347 |
| gwloh | gwloh | 0.027573 | 0.296885 | 0.374998 | 1.993800 | 0.387877 |
| pathways | pathways | 0.023956 | 0.102449 | 0.168599 | 1.996037 | 0.453833 |
| tcga_rna | tcga_rna | 0.023956 | 18.495794 | NaN | 1.996037 | NaN |
| tempus_rna | tempus_rna | 0.023956 | 0.110434 | 0.188235 | 1.996037 | 0.480873 |

SYSTEMS AND METHODS FOR PREDICTING HOMOLOGOUS RECOMBINATION DEFICIENCY STATUS OF A SPECIMEN

CROSS REFERENCE TO RELATED APPLICATIONS

This application claims priority to U.S. Provisional Patent Application No. 62/946,347, filed on Dec. 10, 2019, the content of which is hereby incorporated by reference in its entirety for all purposes.

TECHNICAL FIELD

The present disclosure relates generally to use of machine-learning classifiers trained against RNA and/or DNA sequencing of cancerous tissues to predict homologous recombination deficiency.

BACKGROUND

Precision oncology is the practice of tailoring cancer therapy to the unique genomic, epigenetic, and/or transcriptomic profile of an individual tumor. This is in contrast to conventional methods for treating a cancer patient based merely on the type of cancer the patient is afflicted with, e.g., treating all breast cancer patients with a first therapy and all lung cancer patients with a second therapy. Precision oncology was borne out of many observations that different patients diagnosed with the same type of cancer, e.g., breast cancer, responded very differently to common treatment regimes. Over time, researchers have identified genomic, epigenetic, and transcriptomic markers that facilitate some level of prediction as to how an individual cancer will respond to a particular treatment modality.

Therapy targeted to specific genomic alterations is already the standard of care in several tumor types (e.g., as suggested in the National Comprehensive Cancer Network (NCCN) guidelines for melanoma, colorectal cancer, and non-small cell lung cancer). These few, well known mutations in the NCCN guidelines can be addressed with individual assays or small next generation sequencing (NGS) panels. However, for the largest number of patients to benefit from personalized oncology, molecular alterations that can be targeted with off-label drug indications, combination therapy, or tissue agnostic immunotherapy should be assessed. See Schwaederle et al. 2016 *JAMA Oncol.* 2, 1452-1459; Schwaederle et al. 2015 *J Clin Oncol.* 32, 3817-3825; and Wheler et al. 2016 *Cancer Res.* 76, 3690-3701. Large panel NGS assays also cast a wider net for clinical trial enrollment. See Coyne et al. 2017 *Curr. Probl. Cancer* 41, 182-193; and Markman 2017 *Oncology* 31, 158,168.

Genomic analysis of tumors is rapidly becoming routine clinical practice to provide tailored patient treatments and improve outcomes. See Fernandes et al. 2017 *Clinics* 72, 588-594. Indeed, recent studies indicate that clinical care is guided by NGS assay results for 30-40% of patients receiving such testing. See Hirshfield et al. 2016 *Oncologist* 21, 1315-1325; Groisberg et al. 2017 *Oncotarget* 8, 39254-39267; Ross et al. *JAMA Oncol.* 1, 40-49; and Ross et al. 2015 *Arch. Pathol. Lab Med.* 139, 642-649. There is growing evidence that patients who receive therapeutic advice guided by genetics have better outcomes. See, for example Wheler et al. who used matching scores (e.g., scores based on the number of therapeutic associations and genomic aberrations per patient) to demonstrate that patients with higher matching scores have a greater frequency of stable disease, longer time to treatment failure, and greater overall survival (2016 *Cancer Res.* 76, 3690-3701). Such methods may be particularly useful for patients who have already failed multiple lines of therapy.

Targeted therapies have shown significant improvements in patient outcomes, especially in terms of progression-free survival. See Radovich et al. 2016 *Oncotarget* 7, 56491-56500. Recent evidence reported from the IMPACT trial, which involved genetic testing of advanced stage tumors from 3,743 patients and where approximately 19% of patients received matched targeted therapies based on their tumor biology, showed a response rate of 16.2% in patients with matched treatments versus 5.2% in patients with non-matched treatments. See Bankhead. "IMPACT Trial: Support for Targeted Cancer Tx Approaches." *MedPageToday.* Jun. 5, 2018. The IMPACT study further found that the three-year overall survival for patients given a molecularly matched therapy was more than twice that of non-matched patients (15% vs. 7%). See Id. and ASCO Post. "2018 ASCO: IMPACT Trial Matches Treatment to Genetic Changes in the Tumor to Improve Survival Across Multiple Cancer conditions." *The ASCO POST.* Jun. 6, 2018. Estimates of the proportion of patients for whom genetic testing changes the trajectory of their care vary widely, from approximately 10% to more than 50%. See Fernandes et al. 2017 *Clinics* 72, 588-594.

One example of a genomic trait that has been linked to the efficacy of particular therapies are mutations in the BRCA1, BRCA2, or PALB2 homologous recombination genes. A class of pharmacological inhibitors of Poly ADP ribose polymerase 1 (PARP1), known as PARP inhibitors (PARPi), have therapeutic efficacy for treating some cancers containing a mutation in the BRCA1, BRCA2, or PALB2 homologous recombination genes. PARP1 is an essential enzyme in the error-prone microhomology-mediated end joining (MMEJ) DNA repair pathway. Sharma S. et al., Cell Death Dis. 6(3):e1697 (2015). In the absence of PARP1 activity, DNA replication forks stall when encountering a single-strand break. Fork stalling ultimately results in double-stranded chromosomal breaks that can be repaired by homologous recombination (HR) repair, which is much less error prone than the MMEJ pathway.

Unlike other DNA repair proteins, which are commonly deficient in cancer cells, PARP1 has been shown to be over-expressed in certain cancer types. It has been theorized that increased MMEJ DNA repair, relative to homologous repair, results in the accumulation of genomic mutations, which can lead to the development of cancer. However, the efficacy of PARP inhibitors is not completely understood. For instance, not all cancers with a BRCA1, BRCA2, or PALB2 mutation are sensitive to PARP inhibitors. Further, some cancers without a mutation in any homologous recombination protein are sensitive to PARP inhibitors.

Homologous recombination (HR) is a normal, highly conserved DNA repair process that enables the exchange of genetic information between identical or closely related DNA molecules. It is most widely used by cells to accurately repair harmful breaks (i.e. damage) that occur on both strands of DNA. DNA damage may occur from exogenous (external) sources like UV light, radiation, or chemical damage; or from endogenous (internal) sources like errors in DNA replication or other cellular processes that create DNA damage. Double strand breaks are a type of DNA damage.

HRD is a biomarker of PARP inhibitor sensitivity, and is defined as a disease state arising in tumors through loss of the homologous recombination DNA repair pathway, most commonly through biallelic inactivation of BRCA1/2. HRD is conventionally detected in DNA sequencing data by counting certain characteristic megabase-scale copy number alterations that accumulate over time in the absence of HR repair. However, this DNA-based method can fail to detect patient specimens that have yet to amass a large number of genetic lesions, either due to chance or recent HRD. These undetected patients may not have the opportunity to be prescribed PARP inhibitors or other DNA-damaging therapies without an HRD diagnosis. There is a need for a method that detects a greater percentage of HRD-positive patients.

Using poly (ADP-ribose) polymerase (PARP) inhibitors in patients with HRD compromises two pathways of DNA repair, resulting in cell death (apoptosis). The efficacy of PARP inhibitors is improved not only in ovarian cancers displaying germline or somatic BRCA mutations, but also in cancers in which HRD is caused by other underlying etiologies.

Poly (ADP-ribose) polymerase (PARP) is a family of proteins involved in a number of cellular processes such as DNA repair, genomic stability, and programmed cell death. Homologous recombination deficiency ("HR deficiency" or "HRD") is a deficiency that has been shown to increase the efficacy of PARP inhibitors (PARPi) and platinum-based therapies for patients. The most common lesions in cell DNA are single strand breaks (SSB), happening in tens of thousands per cells per day. PARPs are DNA repair enzymes that help repair single stranded breaks. When these PARPs are not working or are blocked (through a PARP inhibitor therapy, for example), this often leads to what are called double stranded breaks (DSBs). Homologous recombination repair (HRR) is the main way the body repairs these DSBs. If cancer cells have HRD (or, in other words, deficient HRR), the likelihood of the cell recovering from the DSB lowers, leading the cell into apoptosis (programmed cell death), instead of the cell continuing to proliferate. Causing cancer cells to die is one way to stop a person's cancer from growing.

HRD is considered by some as a disease state arising in tumors through loss of the homologous recombination DNA repair pathway, commonly caused by biallelic inactivation of BRCA1/2. The deficiency is often signaled by a mutation in the BRCA genes, but, as is common in cancer, there are other ways a tumor can have a HR deficiency.

Across cancers, HRD occurs at a frequency of about 6%. Rates can be as high as 30% for ovarian cancer, and intermediate for breast, pancreatic and prostate cancer (12-13%). HRD may be driven by biallelic inactivation of BRCA1, BRCA2, RAD51C and PALB2. Loss of heterozygosity (LOH) and deletions (especially of BRCA2) are also thought to be a major cause.

SUMMARY

Given the above background, what is needed in the art are improved ways to predict which cancers are homologous recombination deficiency (HRD) positive, e.g., to identify which cancer patients are more likely to respond favorably to PARP inhibitors and/or platinum-containing neoadjuvant chemotherapy. The present disclosure addresses these and other needs by providing systems and methods for evaluating RNA and/or DNA sequencing results from cancerous tissues using a machine-learning algorithm trained to predict the homologous recombination status of a cancer.

Loss of homologous recombination is a widely-recognized determinant of cancer progression. Yet, few computational resources exist to estimate homologous recombination deficiency (HRD) from patient genomes. Canonically, HRD is primarily known to result from biallelic loss of BRCA1 or of BRCA2. While biallelic loss is definitional of HRD, a number of other factors can result in HRD, including mutation of other DNA repair genes, epigenetic mechanisms, and unknown factors. However, identifying HRD positive cancers that do not have biallelic loss of BRCA1 or of BRCA2 is difficult. Advantageously, the present disclosure provides genomics-based HRD ensemble systems and methods that are not reliant upon detection of biallelic loss of BRCA1 or of BRCA2 to identify HRD cancers. Such testing is valuable for cancer diagnostics and could be used for patient stratification towards treatment with, for example, PARPi and/or platinum-containing neoadjuvant chemotherapy.

In one aspect, methods and systems for determining a homologous recombination pathway status of a cancer in a test subject are provided. All or portions of such methods are performed at a computer system having one or more processors, and memory storing one or more programs for execution by the one or more processors. The method includes obtaining a first plurality of sequence reads, in electronic form, of a DNA sample from the test subject, the DNA sample comprising DNA molecules from a cancerous tissue of the subject. The method also includes obtaining a second plurality of sequence reads, in electronic form, of an RNA sample from the test subject, the RNA sample comprising RNA molecules from the cancerous tissue of the subject. The method includes determining, based on the first plurality of sequence reads, a first prediction for the homologous recombination pathway status of the cancerous tissue of the subject based on a measure of genome-wide loss of heterozygosity for the cancerous tissue of the subject. The method includes determining, based on the second plurality of sequence reads, a second prediction for the homologous recombination pathway status of the cancerous tissue of the subject based on the expression levels of a plurality of genes in the cancerous tissue of the subject. The method includes generating a subject data construct comprising (i) the first prediction for the homologous recombination pathway status of the cancerous tissue of the subject and (ii) the second prediction for the homologous recombination pathway status of the cancerous tissue of the subject. The method includes inputting the subject data construct into an ensemble model trained to distinguish between cancers with homologous recombination pathway deficiencies and cancers without homologous recombination pathway deficiencies, thereby determining the homologous recombination pathway status of the test subject.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A, 1B, and 1C collectively illustrates a block diagram of an example of a computing device for using information derived from DNA sequencing and RNA sequencing of cancerous tissue to predict the homologous recombination status of a cancer, in accordance with some embodiments of the present disclosure.

FIGS. 5A, 5B, and 5C collectively provide a flow chart of an example method 500 for using information derived from DNA sequencing and RNA sequencing of cancerous tissue to predict the homologous recombination status of a cancer, in accordance with some embodiments of the present disclosure.

FIGS. 6A, 6B, and 6C illustrate example components of a clinical report, showing advice based on results of an HRD ensemble model as described herein, issued to provide clinical support for personalized cancer therapy, in accordance with some embodiments of the present disclosure.

FIG. 8 is a table illustrating example trained elastic net models, e.g., trained as described in block 310 of FIG. 3, with the top five performance metrics, in accordance with some embodiments of the present disclosure.

FIGS. 11A and 11B illustrate metrics for the best-performing individual models of each data type, trained as described in Example 6, where ground truth HRD status is defined using bi-allelic inactivation (BRCA-deficient, at least two pathogenic mutations or copy-loss events in either BRCA1 or BRCA2) as a proxy for HRD+ status.

FIGS. 12A and 12B illustrate confusion matrices for the performance of a stacked model where ground truth HRD status is defined using bi-allelic inactivation (BRCA-deficient, at least two pathogenic mutations or copy-loss events in either BRCA1 or BRCA2) as a proxy for HRD+ status (FIG. 12A) and confusion matrices for the performance of the stacked model on single cancer-type cohorts, again using bi-allelic inactivation as a proxy for HRD+ status (FIG. 12B).

DETAILED DESCRIPTION

Figure 1A:
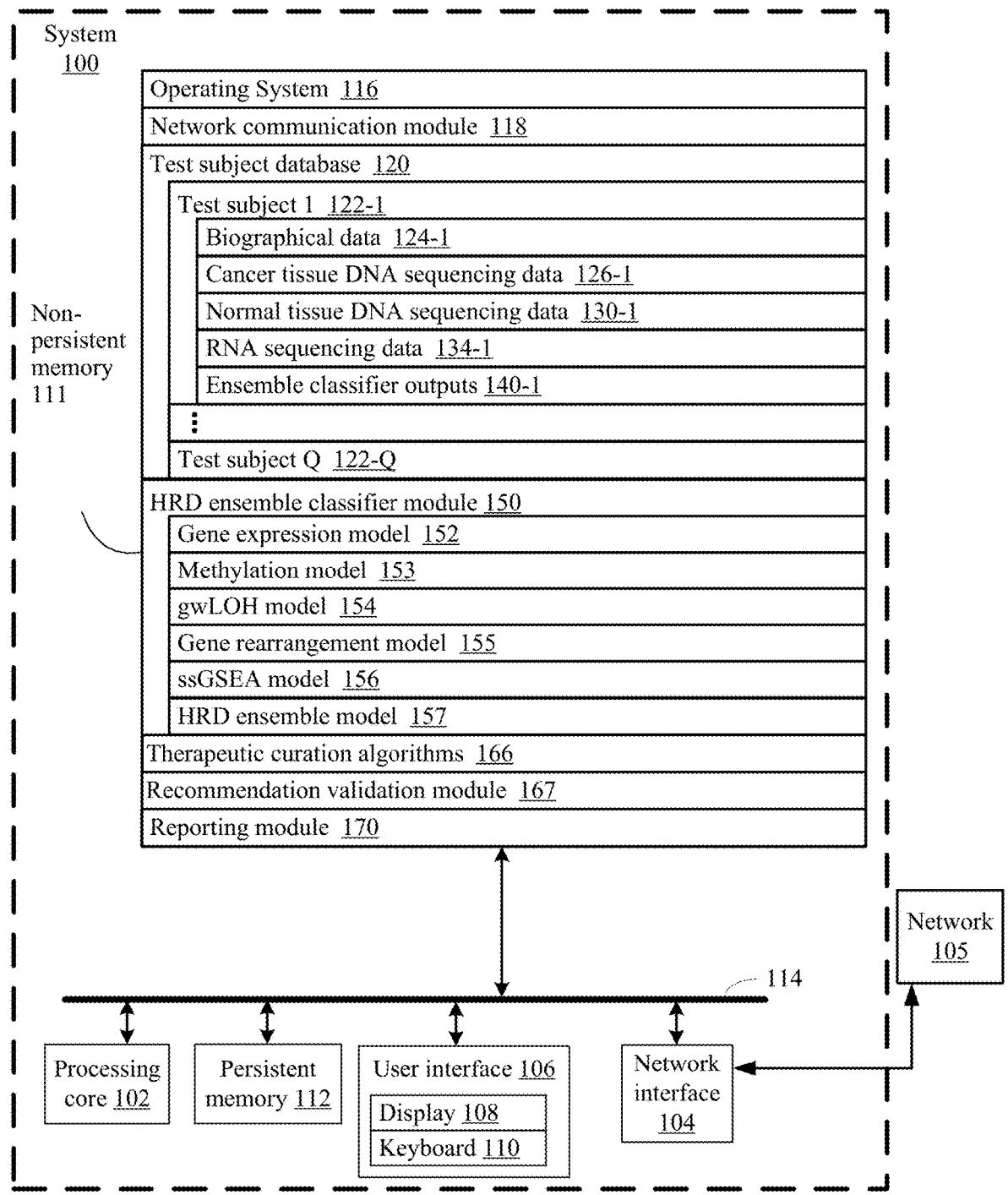

The present disclosure provides systems and methods for using information derived from RNA sequencing and DNA sequencing of cancerous tissue to predict the homologous recombination status of a cancer, to improve treatment predictions and outcomes. In some embodiments, DNA sequencing data from matched cancerous tissue and germline tissue are used together to improve the accuracy of the predictions.

In some embodiments, ensemble classifiers, e.g., that stack HRD predictions made separately from RNA sequencing data and DNA sequencing data improve HRD status predictions. For example, as described in Example 7, use of an ensemble model that combines HRD status predictions made from a first model trained against mRNA transcription data generated from a cancerous tissue or a subject and a second model trained against genome-wide loss of heterozygosity (gwLOH) determined from DNA sequencing data generated from a cancerous tissue, and optionally DNA sequencing from a matched non-cancerous tissue sample from the subject, provides significantly improved performance relative to the performance of either model alone. See, for example, performance metrics reported in Examples 17 and 18.

In some embodiments, the systems and methods provided herein facilitate improved HRD prediction by leveraging data from both RNA sequencing and DNA sequencing of cancerous tissue samples. In some embodiments, this data is integrated together in an ensemble classifier, in which one or more classifier is trained against features of the RNA sequencing data, one or more classifiers is trained against features of the DNA sequencing data, and then an ensemble classifier is trained against the output from the one or more RNA sequencing data classifiers and the one or more DNA sequencing data classifiers. In some embodiments, the classifiers are further trained against the cancer type, as well as the RNA and/or DNA sequencing features.

One obstacle to training a model for determining HRD status is the relative unavailability of ground truth target labels for the training data. Specifically, determining which specimens in a training dataset actually have HRD and would respond, e.g., to PARPi therapy and/or platinum-containing neoadjuvant chemotherapy, and which do not. In some embodiments, an HRD prediction model described herein is trained against a data set where a genetic trait is used as a proxy for HRD status, to provide a ground truth label enabling training over a much larger training cohort. In some embodiments, bi-alleleic BRCA deficiency—bi-allelic loss of either BRCA1 or BRCA2—is used as a proxy for HRD positive status, and completely wild-type BRCA1 and BRCA2 status—e.g., no single nucleotide variants, no short insertions or deletions, and diploid copy number of both the BRCA1 and BRCA2 genes—is used as a proxy for HRD negative status. Accordingly, possible samples in a master training cohort database that contain a nucleotide variant, insertion, or deletion in a BRCA1 or BRCA2 gene, or are not diploid for either the BRCA1 or BRCA2 gene, but that do not demonstrate bi-alleleic BRCA deficiency, are excluded from the training cohort. In some embodiments, it may be difficult to determine whether each BRCA1 or BRCA2 allele is associated with a loss of function variant, for example, two variants in BRCA1 may be on the same allele. These samples may be excluded or may be assumed to have a bi-allelic loss of BRCA1 or BRCA2.

Accordingly, in one aspect, the disclosure provides a method for training a classifier for predicting the HRD status of a test sample. The method includes selecting, from a larger database comprising RNA and/or DNA sequencing data from a cancerous tissue, a first subset of samples that show bi-alleleic BRCA deficiency and a second subset of samples that are completely wild type for the BRCA1 and BRCA2 genes. The first subset of samples is labeled as HRD positive, and the second subset of samples is labeled as HRD negative. A model is then trained against data constructs, for each of the samples in the first subset and second subset, that include (i) one or more features of the RNA and/or DNA sequencing data (e.g., one or more of mRNA expression levels for a plurality of genes, a measure of loss of genomic heterozygosity, a measure of genomic and/or transcriptomic rearrangements (e.g., one or more of insertions, deletions, gene fusions, inversions, etc.), a measure of genomic methylation, etc.), (ii) the HRD label assigned to the sample based on the BRCA status of the sample, and (iii) optionally a cancer type label for the sample.

Definitions

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Furthermore, to the extent that the terms "including," "includes," "having," "has," "with," or variants thereof are used in either the detailed description and/or the claims, such terms are intended to be inclusive in a manner similar to the term "comprising."

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject," "user," and "patient" are used interchangeably herein.

As used herein, the term "subject" refers to any living or non-living human. In some embodiments, a subject is a male or female of any stage (e.g., a man, a woman or a child).

As used herein, the terms "control," "control sample," "reference," "reference sample," "normal," and "normal sample" describe a sample from a subject that does not have a particular condition, or is otherwise healthy. In an example, a method as disclosed herein can be performed on a subject having a tumor, where the reference sample is a sample taken from a healthy tissue of the subject. A reference sample can be obtained from the subject, or from a database. The reference can be, e.g., a reference genome that is used to map sequence reads obtained from sequencing a sample from the subject. A reference genome can refer to a haploid or diploid genome to which sequence reads from the biological sample and a constitutional sample can be aligned and compared. An example of a constitutional sample can be DNA of whole blood or blood cells obtained from the subject. For a haploid genome, there can be only one nucleotide at each locus. For a diploid genome, heterozygous loci can be identified; each heterozygous locus can have two alleles, where either allele can allow a match for alignment to the locus.

As used herein, the term "locus" refers to a position (e.g., a site) within a genome, e.g., on a particular chromosome. In some embodiments, a locus refers to a single nucleotide position within a genome, i.e., on a particular chromosome. In some embodiments, a locus refers to a small group of nucleotide positions within a genome, e.g., as defined by a mutation (e.g., substitution, insertion, or deletion) of consecutive nucleotides within a cancer genome. Because normal mammalian cells have diploid genomes, a normal mammalian genome (e.g., a human genome) will generally have two copies of every locus in the genome, or at least two copies of every locus located on the autosomal chromosomes, e.g., one copy on the maternal autosomal chromosome and one copy on the paternal autosomal chromosome.

As used herein, the term "allele" refers to a particular sequence of one or more nucleotides at a chromosomal locus.

As used herein, the term "reference allele" refers to the sequence of one or more nucleotides at a chromosomal locus that is either the predominant allele represented at that chromosomal locus within the population of the species (e.g., the "wild-type" sequence), or an allele that is predefined within a reference genome for the species.

As used herein, the term "variant allele" refers to a sequence of one or more nucleotides at a chromosomal locus that is either not the predominant allele represented at that chromosomal locus within the population of the species (e.g., not the "wild-type" sequence), or not an allele that is predefined within a reference genome for the species.

As used herein, the term "single nucleotide variant" or "SNV" refers to a substitution of one nucleotide to a different nucleotide at a position (e.g., site) of a nucleotide sequence, e.g., a sequence read from an individual. A substitution from a first nucleobase X to a second nucleobase Y may be denoted as "X>Y." For example, a cytosine to thymine SNV may be denoted as "C>T."

As used herein, the term "mutation" or "variant" refers to a detectable change in the genetic material of one or more cells. In a particular example, one or more mutations can be found in, and can identify, cancer cells (e.g., driver and passenger mutations). A mutation can be transmitted from a parent cell to a daughter cell. A person having skill in the art will appreciate that a genetic mutation (e.g., a driver mutation) in a parent cell can induce additional, different mutations (e.g., passenger mutations) in a daughter cell. A mutation generally occurs in a nucleic acid. In a particular example, a mutation can be a detectable change in one or more deoxyribonucleic acids or fragments thereof. A mutation generally refers to nucleotides that are added, deleted, substituted for, inverted, or transposed to a new position in a nucleic acid. A mutation can be a spontaneous mutation or an experimentally induced mutation. A mutation in the sequence of a particular tissue is an example of a "tissue-specific allele." For example, a tumor can have a mutation that results in an allele at a locus that does not occur in normal cells. Another example of a "tissue-specific allele" is a fetal-specific allele that occurs in the fetal tissue, but not the maternal tissue.

As used herein, the term "loss of heterozygosity" refers to the loss of one copy of a segment (e.g., including part or all of one or more genes) of the genome of a diploid subject (e.g., a human) or loss of one copy of a sequence encoding a functional gene product in the genome of the diploid subject, in a tissue, e.g., a cancerous tissue, of the subject. As used herein, when referring to a metric representing loss of heterozygosity across the entire genome of the subject, loss of heterozygosity is caused by the loss of one copy of various segments in the genome of the subject. Loss of heterozygosity across the entire genome may be estimated without sequencing the entire genome of a subject, and such methods for such estimations based on gene panel targeting-based sequencing methodologies are described in the art. Accordingly, in some embodiments, a metric representing loss of heterozygosity across the entire genome of a tissue of a subject is represented as a single value, e.g., a percentage or fraction of the genome. In some cases a tumor is composed of various sub-clonal populations, each of which may have a different degree of loss of heterozygosity across their respective genomes. Accordingly, in some embodiments, loss of heterozygosity across the entire genome of a cancerous tissue refers to an average loss of heterozygosity across a heterogeneous tumor population. As used herein, when referring to a metric for loss of heterozygosity in a particular gene, e.g., a DNA repair protein such as a protein involved in the homologous DNA recombination pathway (e.g., BRCA1 or BRCA2), loss of heterozygosity refers to complete or partial loss of one copy of the gene encoding the protein in the genome of the tissue and/or a mutation in one copy of the gene that prevents translation of a full-length gene product, e.g., a frameshift or truncating (creating a premature stop codon in the gene) mutation in the gene of interest. In some cases a tumor is composed of various sub-clonal populations, each of which may have a different mutational status in a gene of interest. Accordingly, in some embodiments, loss of heterozygosity for a particular gene of interest is represented by an average value for loss of heterozygosity for the gene across all sequenced sub-clonal populations of the cancerous tissue. In other embodiments, loss of heterozygosity for a particular gene of interest is represented by a count of the number of unique incidences of loss of heterozygosity in the gene of interest across all sequenced sub-clonal populations of the cancerous tissue (e.g., the number of unique frame-shift and/or truncating mutations in the gene identified in the sequencing data).

As used herein the term "cancer," "cancerous tissue," or "tumor" refers to an abnormal mass of tissue in which the growth of the mass surpasses and is not coordinated with the growth of normal tissue. A cancer or tumor can be defined as "benign" or "malignant" depending on the following characteristics: degree of cellular differentiation including morphology and functionality, rate of growth, local invasion and metastasis. A "benign" tumor can be well differentiated, have characteristically slower growth than a malignant tumor and remain localized to the site of origin. In addition, in some cases a benign tumor does not have the capacity to infiltrate, invade or metastasize to distant sites. A "malignant" tumor can be poorly differentiated (anaplasia), have characteristically rapid growth accompanied by progressive infiltration, invasion, and destruction of the surrounding tissue. Furthermore, a malignant tumor can have the capacity to metastasize to distant sites. Accordingly, a cancer cell is a cell found within the abnormal mass of tissue whose growth is not coordinated with the growth of normal tissue. Accordingly, a "tumor sample" refers to a biological sample obtained or derived from a tumor of a subject, as described herein. A cancerous tissue can refer to blood cells if the cancer is a hematological (blood) cancer.

As used herein, the terms "sequencing," "sequence determination," and the like as used herein refers generally to any and all biochemical processes that may be used to determine the order of biological macromolecules such as nucleic acids or proteins. For example, sequencing data can include all or a portion of the nucleotide bases in a nucleic acid molecule such as an mRNA transcript or a genomic locus.

As used herein, the term "sequence reads" or "reads" refers to nucleotide sequences produced by any sequencing process described herein or known in the art. Reads can be generated from one end of nucleic acid fragments ("single-end reads"), and sometimes are generated from both ends of nucleic acids (e.g., paired-end reads, double-end reads). The length of the sequence read is often associated with the particular sequencing technology. High-throughput methods, for example, provide sequence reads that can vary in size from tens to hundreds of base pairs (bp). In some embodiments, the sequence reads are of a mean, median or average length of about 15 bp to 900 bp long (e.g., about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. In some embodiments, the sequence reads are of a mean, median or average length of about 1000 bp, 2000 bp, 5000 bp, 10,000 bp, or 50,000 bp or more. Nanopore sequencing, for example, can provide sequence reads that can vary in size from tens to hundreds to thousands of base pairs. Illumina parallel sequencing can provide sequence reads that do not vary as much, for example, most of the sequence reads can be smaller than 200 bp. A sequence read (or sequencing read) can refer to sequence information corresponding to a nucleic acid molecule (e.g., a string of nucleotides). For example, a sequence read can correspond to a string of nucleotides (e.g., about 20 to about 150) from part of a nucleic acid fragment, can correspond to a string of nucleotides at one or both ends of a nucleic acid fragment, or can correspond to nucleotides of the entire nucleic acid fragment. A sequence read can be obtained in a variety of ways, e.g., using sequencing techniques or using probes, e.g., in hybridization arrays or capture probes, or amplification techniques, such as the polymerase chain reaction (PCR) or linear amplification using a single primer or isothermal amplification.

As used herein, the term "read segment" or "read" refers to any nucleotide sequences including sequence reads obtained from an individual and/or nucleotide sequences derived from the initial sequence read from a sample obtained from an individual. For example, a read segment can refer to an aligned sequence read, a collapsed sequence read, or a stitched read. Furthermore, a read segment can refer to an individual nucleotide base, such as a single nucleotide variant.

As used herein, the term, "reference exome" refers to any particular known, sequenced or characterized exome, whether partial or complete, of any tissue from any organism or pathogen that may be used to reference identified sequences from a subject. Example reference exomes used for human subjects as well as many other organisms are provided in the on-line genome browser hosted by the National Center for Biotechnology Information ("NCBI").

As used herein, the term "reference genome" refers to any particular known, sequenced or characterized genome, whether partial or complete, of any organism or pathogen that may be used to reference identified sequences from a subject. Exemplary reference genomes used for human subjects as well as many other organisms are provided in the on-line genome browser hosted by the National Center for Biotechnology Information ("NCBI") or the University of California, Santa Cruz (UCSC). A "genome" refers to the complete genetic information of an organism or pathogen, expressed in nucleic acid sequences. As used herein, a reference sequence or reference genome often is an assembled or partially assembled genomic sequence from an individual or multiple individuals. In some embodiments, a reference genome is an assembled or partially assembled genomic sequence from one or more human individuals. The reference genome can be viewed as a representative example of a species' set of genes. In some embodiments, a reference genome comprises sequences assigned to chromosomes. Exemplary human reference genomes include but are not limited to NCBI build 34 (UCSC equivalent: hg16), NCBI build 35 (UCSC equivalent: hg17), NCBI build 36.1 (UCSC equivalent: hg18), GRCh37 (UCSC equivalent: hg19), and GRCh38 (UCSC equivalent: hg38).

As used herein, the term "assay" refers to a technique for determining a property of a substance, e.g., a nucleic acid, a protein, a cell, a tissue, or an organ. An assay (e.g., a first assay or a second assay) can comprise a technique for determining the copy number variation of nucleic acids in a sample, the methylation status of nucleic acids in a sample, the fragment size distribution of nucleic acids in a sample, the mutational status of nucleic acids in a sample, or the fragmentation pattern of nucleic acids in a sample. Any assay known to a person having ordinary skill in the art can be used to detect any of the properties of nucleic acids mentioned herein. Properties of a nucleic acids can include a sequence, genomic identity, copy number, methylation state at one or more nucleotide positions, size of the nucleic acid, presence or absence of a mutation in the nucleic acid at one or more nucleotide positions, and pattern of fragmentation of a nucleic acid (e.g., the nucleotide position(s) at which a nucleic acid fragments). An assay or method can have a particular sensitivity and/or specificity, and their relative usefulness as a diagnostic tool can be measured using ROC-AUC statistics.

The term "classification" can refer to any number(s) or other characters(s) that are associated with a particular property of a sample. For example, in some embodiments, the term "classification" can refer to a type of cancer in a subject or sample, a stage of cancer in a subject or sample, a prognosis for a cancer in a subject or sample, a tumor load in a subject, a presence of tumor metastasis in a subject, and the like. The classification can be binary (e.g., positive or negative) or have more levels of classification (e.g., a scale from 1 to 10 or 0 to 1). The terms "cutoff" and "threshold" can refer to predetermined numbers used in an operation. For example, a cutoff size can refer to a size above which fragments are excluded. A threshold value can be a value above or below which a particular classification applies. Either of these terms can be used in either of these contexts.

Several aspects are described below with reference to example applications for illustration. It should be understood that numerous specific details, relationships, and methods are set forth to provide a full understanding of the features described herein. One having ordinary skill in the relevant art, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

Example System Embodiments

Now that an overview of some aspects of the present disclosure and some definitions used in the present disclosure have been provided, details of an exemplary system for determining a homologous recombination pathway status of a cancer in a test subject are now described in conjunction with FIGS. 1A-C. FIGS. 1A-C collectively illustrate the topology of an example system for determining a homologous recombination pathway status of a cancer, in accordance with some embodiments of the present disclosure. Advantageously, the example system illustrated in FIGS. 1A-C improves upon conventional methods for providing clinical support for personalized cancer therapy by utilizing an ensemble model for improved classification of HRD status in cancers, thus informing treatment recommendations.

FIG. 1A is a block diagram illustrating a system in accordance with some implementations. The device 100 in some implementations includes one or more processing units CPU(s) 102 (also referred to as processors), one or more network interfaces 104, a user interface 106, e.g., including a display 108 and/or an input 110 (e.g., a mouse, touchpad, keyboard, etc.), a non-persistent memory 111, a persistent memory 112, and one or more communication buses 114 for interconnecting these components. The one or more communication buses 114 optionally include circuitry (sometimes called a chipset) that interconnects and controls communications between system components. The non-persistent memory 111 typically includes high-speed random access memory, such as DRAM, SRAM, DDR RAM, ROM, EEPROM, flash memory, whereas the persistent memory 112 typically includes CD-ROM, digital versatile disks (DVD) or other optical storage, magnetic cassettes, magnetic tape, magnetic disk storage or other magnetic storage devices, magnetic disk storage devices, optical disk storage devices, flash memory devices, or other non-volatile solid state storage devices. The persistent memory 112 optionally includes one or more storage devices remotely located from the CPU(s) 102. The persistent memory 112, and the non-volatile memory device(s) within the non-persistent memory 112, comprise non-transitory computer readable storage medium. In some implementations, the non-persistent memory 111 or alternatively the non-transitory computer readable storage medium stores the following programs, modules and data structures, or a subset thereof, sometimes in conjunction with the persistent memory 112:

- an operating system 116, which includes procedures for handling various basic system services and for performing hardware dependent tasks;
- a network communication module (or instructions) 118 for connecting the system 100 with other devices and/or a communication network 105;
- a test subject database 120 for storing one or more collections of data from test subjects (e.g., cancer patients);
- an HRD ensemble classifier module 150 for inputting sequencing data, obtaining model scores from sequencing data, and obtaining classifications of HRD status based on model scores;
- a therapeutic curation algorithm module 166 for obtaining treatment recommendations based on classifications obtained from the HRD ensemble classifier module 150;
- a recommendation validation module 167 for validating treatment recommendations obtained from the therapeutic curation algorithm module 166; and
- a reporting module 170 for generating and transmitting reports that provide clinical support for personalized cancer therapy.

Although FIGS. 1A-C depict a "system 100," the figures are intended more as a functional description of the various features that may be present in computer systems than as a structural schematic of the implementations described herein. In practice, and as recognized by those of ordinary skill in the art, items shown separately could be combined and some items could be separated. Moreover, although FIG. 1A depicts certain data and modules in non-persistent memory 111, some or all of these data and modules may be in persistent memory 112. For example, in various implementations, one or more of the above identified elements are stored in one or more of the previously mentioned memory devices, and correspond to a set of instructions for performing a function described above. The above identified modules, data, or programs (e.g., sets of instructions) need not be implemented as separate software programs, procedures, datasets, or modules, and thus various subsets of these modules and data may be combined or otherwise re-arranged in various implementations.

In some implementations, the non-persistent memory 111 optionally stores a subset of the modules and data structures identified above. Furthermore, in some embodiments, the memory stores additional modules and data structures not described above. In some embodiments, one or more of the above-identified elements is stored in a computer system, other than that of system 100, that is addressable by system 100 so that system 100 may retrieve all or a portion of such data when needed.

For purposes of illustration in FIG. 1A, system 100 is represented as a single computer that includes all of the functionality for providing clinical support for personalized cancer therapy. However, while a single machine is illustrated, the term "system" shall also be taken to include any collection of machines that individually or jointly execute a set (or multiple sets) of instructions to perform any one or more of the methodologies discussed herein.

For example, in some embodiments, system 100 includes one or more computers. In some embodiments, the functionality for providing clinical support for personalized cancer therapy is spread across any number of networked computers and/or resides on each of several networked computers and/or is hosted on one or more virtual machines at a remote location accessible across the communications network 105. For example, different portions of the various modules and data stores illustrated in FIGS. 1A-C can be stored and/or executed on the various instances of a processing device and/or processing server/database in the distributed diagnostic environment 210 illustrated in FIG. 2 (e.g., processing devices 224, 234, 244, and 254, processing server 262, and database 264).

The system may operate in the capacity of a server or a client machine in client-server network environment, as a peer machine in a peer-to-peer (or distributed) network environment, or as a server or a client machine in a cloud computing infrastructure or environment. The system may be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine.

In another implementation, the system comprises a virtual machine that includes a module for executing instructions for performing any one or more of the methodologies disclosed herein. In computing, a virtual machine (VM) is an emulation of a computer system that is based on computer architectures and provides functionality of a physical computer. Some such implementations may involve specialized hardware, software, or a combination of hardware and software.

One of skill in the art will appreciate that any of a wide array of different computer topologies are used for the application and all such topologies are within the scope of the present disclosure.

Test Subject Database (120)

Referring to FIG. 1B, in some embodiments, the system (e.g., system 100) includes a test subject database 120 that stores data for test subjects 122-1 to 122-Q (e.g., cancer patients or patients being tested for cancer) including one or more bibliographic data 124 (e.g., 124-1), one or more cancer tissue DNA sequencing data 126 (e.g., 126-1), one or more normal tissue DNA sequencing data 130 (e.g., 130-1), one or more RNA sequencing data 134 (e.g., 134-1), and one or more ensemble classifier outputs 140 (e.g., 140-1). These data are used and/or generated by the various processes stored in system 100. In some embodiments, the data stored for one test subject may include a different set of features that the data stored for another test subject. Further, while illustrated as a single data construct in FIG. 1B, different sets of subject data may be stored in different databases or modules spread across one or more system memories.

In some embodiments, the test subject database 120 includes bibliographic data 124. In some embodiments, the bibliographic data 124 includes a cancer type of the subject 125-1-$a$. In some embodiments, the bibliographic data 124 includes personal characteristics 125-1-$b$ of the subject, such as patient name, date of birth, gender, ethnicity, physical address, smoking status, alcohol consumption characteristic, anthropomorphic data, etc. In some embodiments, the bibliographic data 124 includes medical history data 125-1-$c$ for the subject, such as cancer diagnosis information (e.g., date of initial diagnosis, date of metastatic diagnosis, cancer staging, tumor characterization, tissue of origin, previous treatments and outcomes, adverse effects of therapy, therapy group history, clinical trial history, previous and current medications, surgical history, etc.), previous or current symptoms, previous or current therapies, previous treatment outcomes, previous disease diagnoses, diabetes status, diagnoses of depression, diagnoses of other physical or mental maladies, and family medical history. In some embodiments, the bibliographic data 124 includes clinical features 125-1-$d$, such as pathology data, medical imaging data, laboratory testing results, and tissue culture and/or tissue organoid culture data. In some embodiments, the bibliographic data 124 further includes a record of treatments administered to the subject (e.g., patient) and subject outcomes following therapy. In some embodiments, bibliographic data 124 is collected from various sources, including at intake directly from the patient, from an electronic medical record (EMR) or electronic health record (EHR) for the patient, or curated from other sources, such as fields from various testing records (e.g., genetic sequencing reports).

In some embodiments, the test subject database 120 includes cancer tissue DNA sequencing data 126 (e.g., obtained from solid-tissue tumor biopsy and/or liquid biopsy). In some embodiments, the cancer tissue DNA sequencing data 126 includes one or more DNA sequencing runs 127 (e.g., 127-1-1, . . . , 127-1-L). In some embodiments, each respective DNA sequencing run 127 comprises a plurality of sequence reads 128 (e.g., 128-1-1-1, . . . , 128-1-1-K) and/or a plurality of aligned sequences 129-1-1 (e.g., as a BAM file).

In some embodiments, the test subject database 120 includes normal tissue DNA sequencing data 130 (e.g., obtained from solid-tissue normal biopsy and/or liquid biopsy). In some embodiments, the normal tissue DNA sequencing data 130 includes one or more DNA sequencing runs 131 (e.g., 131-1-1, . . . , 131-1-N). In some embodiments, each respective DNA sequencing run 131 comprises a plurality of sequence reads 132 (e.g., 132-1-1-1, . . . , 132-1-1-M) and/or a plurality of aligned sequences 133-1-1 (e.g., as a BAM file).

In some embodiments, the test subject database 120 includes RNA sequencing data 134 (e.g., obtained from solid-tissue tumor biopsy). In some embodiments, the RNA sequencing data 134 includes one or more RNA sequencing runs 135 (e.g., 135-1-1, . . . , 135-1-P). In some embodiments, each respective DNA sequencing run 135 comprises a plurality of sequence reads 136 (e.g., 136-1-1-1, . . . , 136-1-1-O), a plurality of aligned sequences 137-1-1 (e.g., as a BAM file), and/or expression data 138-1-1 (e.g., obtained from a gene expression analysis of the RNA sequencing data for a plurality of genes).

In some embodiments, sequencing data in the test subject database 120 includes different sets of sequencing data from a single subject, corresponding to different samples from the subject (e.g., a tumor sample, liquid biopsy sample, tumor organoid derived from a tumor, and/or a normal sample), and/or to samples acquired at different times (e.g., while monitoring the progression, regression, remission, and/or recurrence of a cancer in a subject). Each plurality of sequence reads may be in any suitable file format (e.g., BCL, FASTA, FASTQ, etc.). In some embodiments, sequencing data is accessed by a sequencing data processing module, which performs various pre-processing, genome alignment, and demultiplexing operations. In some embodiments, a plurality of sequence reads is aligned to a reference construct (e.g., a reference sequence and/or a reference genome).

Referring to FIG. 1C, in some embodiments, the test subject database 120 includes one or more ensemble classifier outputs 140. In some embodiments, the ensemble classifier outputs 140 include outputs derived from machine learning approaches (e.g., based at least in part on evaluation of any relevant bibliographic data 124, cancer tissue DNA sequencing data 126, normal tissue DNA sequencing data 130, and/or RNA sequencing data 134, considered alone or in combination. In some embodiments, the ensemble classifier outputs 140 include an HRD ensemble model score 147 (e.g., 147-1-1), based on one or more individual outputs (e.g., model scores). For example, in some embodiments, an HRD ensemble model score 147 is based on any one or more of a gene expression model store 142 (142-1-1), a methylation model score 143 (143-1-1), a genome-wide loss of heterozygosity model score 144 (144-1-1), a gene rearrangement model score 145 (145-1-1), and/or a single-sample gene set enrichment analysis model score 146 (146-1-1). In some embodiments, the one or more ensemble classifier outputs 140 further comprise a plurality of HRD determinations 141 (e.g., 141-1-1, . . . , 141-1-R), based on one or more individual outputs (e.g., model scores).

The skilled artisan will know of other types of subject data useful for providing HRD status determination. The listing of features above is merely representative and should not be construed to be limiting.

HRD Ensemble Classifier Module (150)

Referring to FIG. 1A, the system 100 further includes an HRD ensemble classifier module 150 for inputting sequencing data, obtaining model scores from sequencing data, and obtaining classifications of HRD status based on model scores, using, for example, any of the subject data stored in the test subject database 120.

In some embodiments, the HRD ensemble classifier module 150 includes a gene expression model 152, a methylation model 153, a gwLOH model 154, a gene rearrangement model 155, an ssGSEA model 156, and/or an HRD ensemble model 157. The HRD ensemble classifier module 150 and models 152-157 are described in greater detail below with reference to FIGS. 4 and 5A-C. Outputs from the HRD ensemble classifier module 150 and models 152-157 can be stored in the ensemble classifier outputs 140.

In some embodiments, one or more models (e.g., classifiers) in the HRD ensemble classifier module 150 is implemented as an artificial intelligence engine and may include gradient boosting models, random forest models, neural networks (NN), regression models, Naive Bayes models, and/or machine learning algorithms (MLA). A MLA or a NN may be trained from a training data set that includes one or more subject data, including bibliographic data 124, cancer tissue DNA sequencing data 126, normal tissue DNA sequencing data 130, RNA sequencing data 134, and/or ensemble classifier outputs 140. MLAs include supervised algorithms (such as algorithms where the features/classifications in the data set are annotated) using linear regression, logistic regression, decision trees, classification and regression trees, naïve Bayes, nearest neighbor clustering; unsupervised algorithms (such as algorithms where no features/classification in the data set are annotated) using Apriori, means clustering, principal component analysis, random forest, adaptive boosting; and semi-supervised algorithms (such as algorithms where an incomplete number of features/classifications in the data set are annotated) using generative approach (such as a mixture of Gaussian distributions, mixture of multinomial distributions, hidden Markov models), low density separation, graph-based approaches (such as mincut, harmonic function, manifold regularization), heuristic approaches, or support vector machines.

NNs include conditional random fields, convolutional neural networks, attention based neural networks, deep learning, long short term memory networks, or other neural models where the training data set includes a plurality of tumor samples, RNA expression data for each sample, and pathology reports covering imaging data for each sample.

While MLA and neural networks identify distinct approaches to machine learning, the terms may be used interchangeably herein. Thus, a mention of MLA may include a corresponding NN or a mention of NN may include a corresponding MLA unless explicitly stated otherwise. Training may include providing optimized datasets, labeling these traits as they occur in patient records, and training the MLA to predict or classify based on new inputs. Artificial NNs are efficient computing models which have shown their strengths in solving hard problems in artificial intelligence. They have also been shown to be universal approximators, that is, they can represent a wide variety of functions when given appropriate parameters.

In some embodiments, system 100 includes a classifier training module that includes instructions for training one or more untrained or partially trained classifiers based on feature data from a training dataset. In some embodiments, system 100 also includes a database of training data for use in training the one or more classifiers. In other embodiments, the classifier training module accesses a remote storage device hosting training data. In some embodiments, the training data includes a set of training features, including but not limited to, various types of the subject data 120 illustrated in FIG. 1B.

Therapeutic Curation Algorithms (166)

In some embodiments, referring to FIG. 1A, the system 100 includes a therapeutic curation algorithm 166 that assembles actionable variants and characteristics such as an HRD determination 141, matched therapies, and/or relevant clinical trials identified for the subject. For example, in some embodiments, a therapy is curated for a subject based on an HRD classification of the cancer in the subject, where, when the cancer in the subject is determined to be homologous recombination deficiency (HRD) positive, a first treatment is administered, and when the cancer in the subject is determined not to be homologous recombination deficiency (HRD) positive, a second treatment other than the first treatment is administered. In some embodiments, the therapeutic curation algorithm 166 evaluates certain criteria related to which actionable variants and characteristics (e.g., HRD determination 141), matched therapies, and/or relevant clinical trials should be reported and/or whether certain matched therapies, considered alone or in combination, may be counter-indicated or contraindicated for the subject, e.g., based on subject bibliographic data and/or known drug-drug interactions. In some embodiments, the therapeutic curation algorithm generates one or more clinical reports for the subject. In some embodiments, the therapeutic curation algorithm generates a first clinical report that is to be reported to a medical professional treating the subject and a second clinical report that will not be communicated to the medical professional, but may be used to improve various algorithms within the system.

Recommendation Validation Module (167)

In some embodiments, the system 100 includes a recommendation validation module 167 that includes an interface allowing a clinician (for example, a pathologist) to review, modify, and approve a clinical report prior to the report being sent to a medical professional, e.g., an oncologist, treating the patient. For example, in some embodiments, clinical assessment data is generated, modified, and/or validated by evaluation of subject data 120 (e.g., including ensemble classifier outputs 140) by a clinician such as an oncologist. For instance, in some embodiments, a clinician (e.g., at clinical environment 220) uses HRD ensemble classifier module 150, or accesses test subject database 120 directly, to evaluate ensemble classifier outputs 140 to make recommendations for personalized cancer treatment of a patient. Similarly, in some embodiments, a clinician (e.g., at clinical environment 220) reviews recommendations determined using therapeutic curation algorithms 166 and approves, rejects, or modifies the recommendations, e.g., prior to the recommendations being sent to a medical professional treating the cancer patient.

In some embodiments, each of the one or more test subject databases, classifier modules, therapeutic curation algorithms, recommendation validation modules, and/or reporting modules are communicatively coupled to a data bus to transfer data between each module for processing and/or storage. In some alternative embodiments, each of the feature collection, alteration module(s), structural variant and feature store are communicatively coupled to each other for independent communication without sharing the data bus.

Further details on systems and exemplary embodiments of modules and feature collections are discussed in PCT Application PCT/US19/69149, titled "A METHOD AND PROCESS FOR PREDICTING AND ANALYZING PATIENT COHORT RESPONSE, PROGRESSION, AND SURVIVAL," filed Dec. 31, 2019, which is hereby incorporated herein by reference in its entirety.

FIG. 2B: Distributed Diagnostic and Clinical Environment

Figure 2:
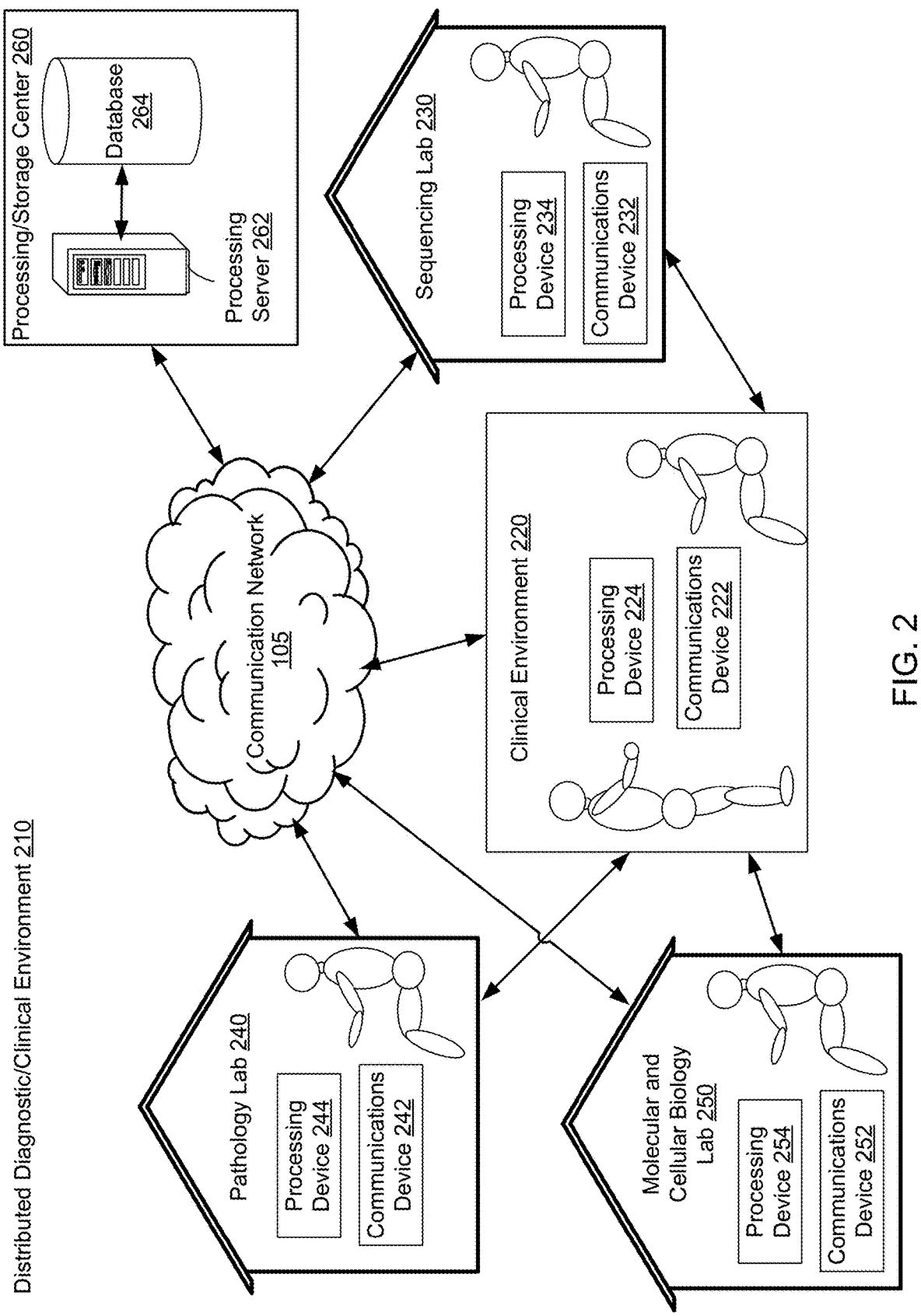
FIG. 2 illustrates an example of a distributed diagnostic environment for collecting and evaluating patient data for the purpose of precision oncology, in accordance with some embodiments of the present disclosure.

In some aspects, the methods described herein for providing clinical support for personalized cancer therapy are performed across a distributed diagnostic/clinical environment, e.g., as illustrated in FIG. 2. However, in some embodiments, the improved methods described herein for predicting the homologous recombination status of a cancer, are performed at a single location, e.g., at a single computing system or environment, although ancillary procedures supporting the methods described herein, and/or procedures that make further use of the results of the methods described herein, may be performed across a distributed diagnostic/clinical environment.

FIG. 2B illustrates an example of a distributed diagnostic/clinical environment 210. In some embodiments, the distributed diagnostic/clinical environment is connected via communication network 105. In some embodiments, one or more biological samples, e.g., one or more liquid biopsy samples, solid tumor biopsy, normal tissue samples, and/or control samples, are collected from a subject in clinical environment 220, e.g., a doctor's office, hospital, or medical clinic, or at a home health care environment (not depicted). Advantageously, while solid tumor samples should be collected within a clinical setting, liquid biopsy samples can be acquired in a less invasive fashion and are more easily collected outside of a traditional clinical setting. In some embodiments, one or more biological samples, or portions thereof, are processed within the clinical environment 220 where collection occurred, using a processing device 224, e.g., a nucleic acid sequencer for obtaining sequencing data, a microscope for obtaining pathology data, a mass spectrometer for obtaining proteomic data, etc. In some embodiments, one or more biological samples, or portions thereof are sent to one or more external environments, e.g., sequencing lab 230, pathology lab 240, and/or molecular biology lab 250, each of which includes a processing device 234, 244, and 254, respectively, to generate biological data 121 for the subject. Each environment includes a communications device 222, 232, 242, and 252, respectively, for communicating biological data 121 about the subject to a processing server 262 and/or database 264, which may be located in yet another environment, e.g., processing/storage center 260. Thus, in some embodiments, different portions of the systems and methods described herein are fulfilled by different processing devices located in different physical environments.

Accordingly, in some embodiments, a method for providing clinical support for personalized cancer therapy, e.g., with improved methodology for predicting the homologous recombination status of a cancer, is performed across one or more environments, as illustrated in FIG. 2B. For instance, in some such embodiments, a biopsy sample is collected at clinical environment 220 or in a home healthcare environment. The sample, or a portion thereof, is sent to sequencing lab 230 where raw sequence reads 123 of nucleic acids in the sample are generated by sequencer 234. The raw sequencing data 123 is communicated, e.g., from communications device 232, to database 264 at processing/storage center 260, where processing server 262 extracts features from the sequence reads by executing one or more of the processes in bioinformatics module 140, thereby generating genomic features 131 for the sample. Processing server 262 may then analyze the identified features by executing one or more of the processes in feature analysis module 160, thereby generating clinical assessment 139, including a clinical report 139-3. A clinician may access clinical report 139-3, e.g., at processing/storage center 260 or through communications network 105, via recommendation validation module 167. After final approval, clinical report 139-3 is transmitted to a medical professional, e.g., an oncologist, at clinical environment 220, who uses the report to support clinical decision making for personalized treatment of the patient's cancer.

Example Methods

Now that details of a system 100 for determining a homologous recombination pathway status of a cancer in a test subject and/or training an algorithm for determining a homologous recombination pathway status of a cancer have been disclosed, details regarding processes and features of the system, in accordance with various embodiment of the present disclosure, are disclosed below. Specifically, example processes are described below with reference to FIGS. 3, 4, and 5. In some embodiments, such processes and features of the system are carried out by modules 118, 150, 166, 167, and/or 170, as illustrated in FIG. 1. Referring to these methods, the systems described herein (e.g., system 100) include instructions for determining a homologous recombination pathway status of a cancer in a test subject and/or training an algorithm for determining a homologous recombination pathway status of a cancer.

Figure 3:
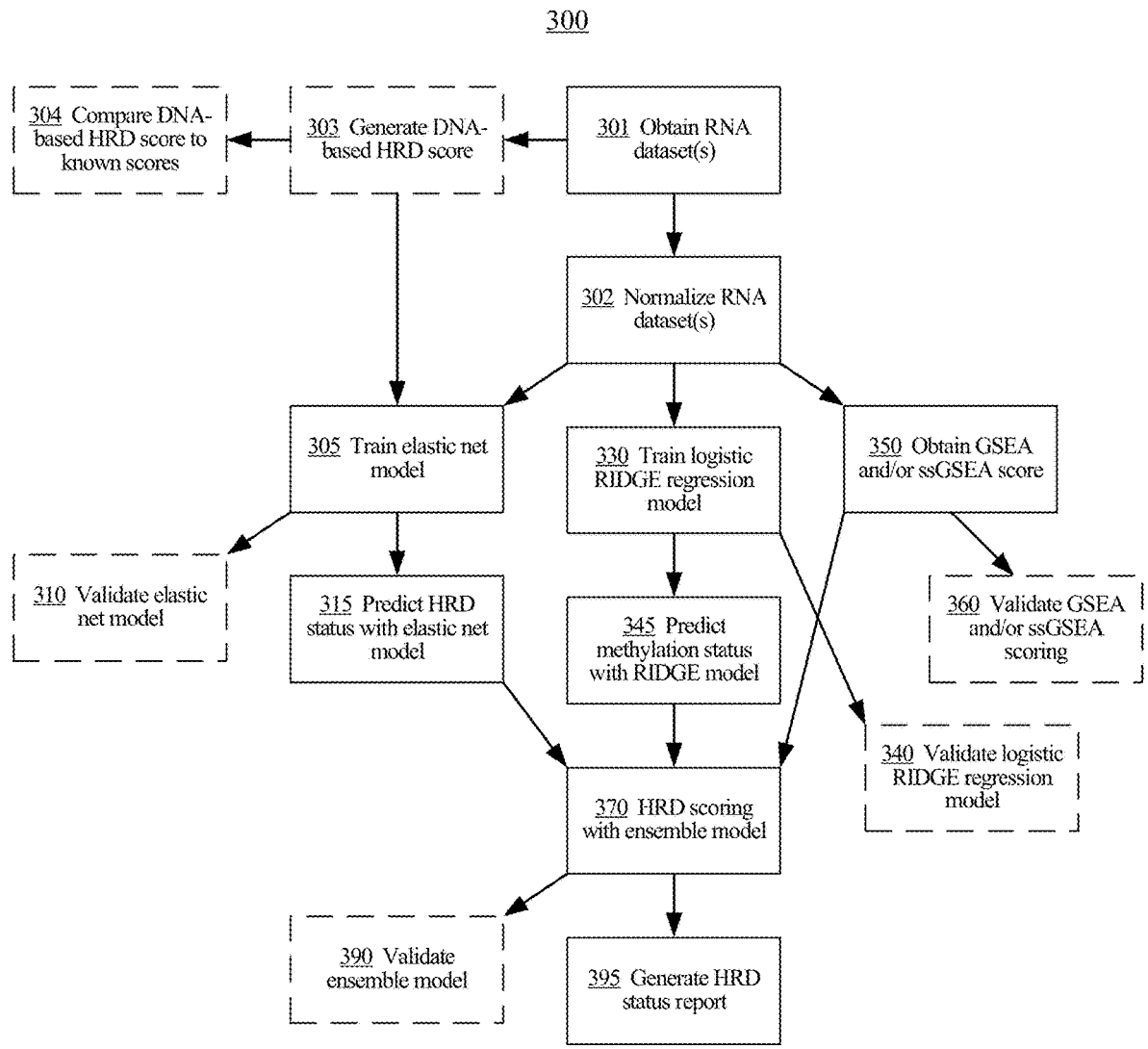
FIG. 3 provides a flow chart of an example method 300 for determining the homologous recombination status of a cancer, based on DNA sequencing and RNA sequencing of cancerous tissue, in accordance with some embodiments of the present disclosure.

FIG. 3 illustrates an example workflow 300 for determining a homologous recombination pathway status of a cancer in a test subject, in accordance with various embodiments of the present disclosure. Further details on various implementations of the steps illustrated in workflow 300 are described with more particularity below. The skilled artisan will know of suitable alternatives for performing each of the steps shown in workflow 300.

In block 301, at least one RNA dataset is received, containing specimen RNA datasets. In one example, each specimen RNA dataset is obtained by processing a human patient specimen or a tumor organoid through RNA-sequencing or expression microarray protocol. The RNA-sequencing may be whole exome RNA-sequencing. In other aspects, a panel of predetermined genes may be assessed through more specific capture methods, as well as qPCR or dPCR assays for single genes.

In other aspects, a cell line dataset may be received. Such dataset may be particularly useful, for example, when used in combination with drug testing methods and/or analysis of cellular material.

In one example, one of the RNA datasets is a training dataset, one is a testing dataset, and one is an input unknown dataset. In one embodiment, the training dataset and the testing dataset include specimen RNA datasets (including RNA-seq transcriptomes and/or SNP array data where available) from The Cancer Genome Atlas (TCGA) and each specimen RNA dataset in each RNA dataset is associated with a cancer type and a DNA-based HRD score (See Knijnenburg et al. 2018 Cell Reports 23(1):239-254). In one embodiment, the training and testing datasets further include specimen RNA datasets that are not in the TCGA database and each of these specimen RNA datasets is associated with a cancer type and a DNA-based HRD score. In one embodiment, the combination of the training and testing datasets contain more than 5, 10, 15, 20, 25, 30, 35, 40, 45, 50, 55, 60, 65, 70, 65, 80, 85, 90, 95, 100, 125, 150, 200, 250, 300, 400, 500, 750, 1000, 10,000, or more specimen RNA datasets.

Each specimen RNA dataset may be further associated with methylation status data. In one example, methylation status data may include a numerical score and/or classes, for example hypomethylated, normal, and hypermethylated classes. In one example, methylation probes used to generate methylation status data may be chosen based on distance between the probe binding site and the gene transcription start site (TSS), and concordance between methylation data status and gene expression. In one example, methylation probes may be chosen that do not bind to a gene body of a gene that shares a promoter with the target gene.

In block 302, the specimen RNA datasets are normalized. In one example, the normalization method is done in accordance with U.S. patent application Ser. No. 16/581,706, which is incorporated by reference herein.

In block 303, a DNA-based HRD score is optionally generated or received for at least one specimen RNA dataset. In one example, the DNA-sequencing data used to generate a DNA-based HRD score are whole exome DNA-sequencing data. In one example, the DNA-sequencing data used to generate a DNA-based HRD score are targeted panel DNA-sequencing data and the DNA-based HRD score is determined by calculating the percent of nucleotide bases covered by the assay that had detectable loss of heterozygosity (LOH). In one embodiment, the targeted panel targets approximately 500 genes.

In block 304, the DNA-based HRD score of a specimen RNA dataset is optionally compared to known DNA-based HRD scores associated with the specimen RNA dataset.

In block 305, an elastic net model is trained with the training specimen RNA datasets and may also be trained with the DNA-based HRD scores generated in block 303. In one example, a separate elastic net model is trained for each TCGA cohort, meaning that a dataset having specimen RNA datasets associated with only one cancer type (or other characteristic defining a cohort) in the TCGA database is used to train each elastic net model. In another example, many cancer types are associated with the training specimen RNA datasets.

In one embodiment, the elastic net transcriptome models were trained to predict DNA-based HRD scores derived from exome and SNP array data for each tumor type represented in TCGA.

In one example, Elastic Net models (with alpha 0, 0.25, 0.5, 0.75, or 1) were trained utilizing RNA data from TCGA processed in-house and DNA-based HRD prediction scores from the literature (Knijnenburg Cell Rep 2018) for each of the 33 TCGA cancers (75% of the specimen RNA datasets from each cancer type were used as training data and 25% as testing data). While certain cancer types where HRD does not appear to be relevant (thyroid, melanoma) did not yield robust models, 11 tumor types produced models with >70% accuracy. In particular, breast, uterine endometrial, and bladder cancer, each of which has literature evidence for HRD, had the best performance (87%, 83% and 82%, respectively).

In one example, another type of linear model may be used instead of an elastic net model.

In block 310, the trained elastic net model is optionally tested by using the trained model to predict an HRD status for individual specimen RNA datasets within the testing dataset and comparing the model output for each specimen RNA dataset to the DNA-based HRD status associated with the specimen RNA dataset. In one example, the testing specimen RNA datasets used for validation are each associated with the same cancer type as the training specimen RNA datasets.

In one example, trained elastic net models each exhibit >80% accuracy in withheld testing data and are well powered to discriminate BRCA-deficient (HRD+, biallelic genetic BRCA1/2 inactivation or deletion) from BRCA-intact (generally HRD-, BRCA1/2 wildtype) specimens.

In block 315, the trained elastic net model predicts an HRD status for at least one specimen RNA dataset in the input unknown dataset. In one example, the model input is a gene expression matrix and the model is trying to predict a numerical DNA-based HRD score.

In block 330, a logistic RIDGE regression model is trained with the methylation status data and specimen RNA datasets in a training dataset. In one embodiment, the methylation status data are associated with a gene promoter region of DNA. In one example, the promoter is the BRCA1 gene promoter.

In one example, a logistic model is trained to detect BRCA1 promoter hypermethylation from specimen RNA datasets in TCGA data.

Promoter methylation is an epigenetic means of inactivating a gene by chemically modifying the DNA to prevent its transcription, rather than genetic mutation which changes the DNA sequence itself. This is a common means of inactivating BRCA1 or other genes in tumors that may be difficult to detect in DNA sequencing data, but which may be detected indirectly by RNA sequencing.

In various embodiments, the trained promoter methylation RIDGE regression model does not use BRCA1 gene expression levels as a feature. While gene promoter hypermethylation may cause low expression levels of that gene, certain specimens with low expression levels of HR pathway-related genes have very low HRD scores. This may be caused by HRD tumors that inactivated BRCA1 through other means and upregulated the gene as a compensatory mechanism.

In one example, another type of linear model may be used instead of a RIDGE regression model.

In block 340, the trained RIDGE regression model is optionally tested by using the trained model to predict a methylation status for specimen RNA datasets within the testing dataset and comparing the model output for a specimen RNA dataset to the actual methylation status associated with the specimen RNA dataset. In one example, the testing specimen RNA datasets used for validation are each associated with the same cancer type as the training specimen RNA datasets.

In one example, the output of a linear model is a continuous numerical variable termed the 'predictor'. In one example, to convert the predictor output into a binary score (for example, 1 or 0, representing hypermethylated and not hypermethylated, respectively), the predictor is compared to a threshold value and if the predictor is higher than that threshold value, the predictor is categorized as hypermethylated. In one example, the validation includes varying the threshold values (for example, in the range of approximately 0.1 to 0.4), analyzing the performance of the trained RIDGE regression model in categorizing the training datasets having known methylation statuses, and calculating an F1 score (for example, the harmonic mean of recall and precision) for the model for each threshold value analyzed. In one example, the threshold value resulting in the highest F1 score is selected.

In one example, the trained RIDGE regression model exhibits >80% accuracy in withheld testing data and are well powered to discriminate BRCA-deficient (HRD+, biallelic genetic BRCA1/2 inactivation or deletion) from BRCA-intact (generally HRD−, BRCA1/2 wildtype) specimens.

In block 345, the trained RIDGE regression model predicts a methylation status for at least one transcriptome in the input unknown dataset. In various embodiments, the methylation status may be a numerical variable in the range −2 to 1 or a binary score of 0 or 1.

In block 350, a GSEA and/or ssGSEA score (See Sergushichev 2016 BioRxiv doi:10.1101/060012 and Foroutan et al. 2018 BMC Bioinformatics 19:404) for at least one gene set is received or generated for at least one transcriptome in the input unknown dataset. In one example, GSEA and/or ssGSEA scores are generated for a transcriptome by comparing expression levels of genes within the gene set to expression levels of other genes. In one example, only ssGSEA scores are received or generated.

In one example, block 350 includes leveraging the mSigDB collection of annotated gene sets to conduct single sample gene set enrichment analysis (ssGSEA) on Tempus-sequenced patients, selecting over a hundred gene sets that were predictive of BRCA-deficiency, using LASSO.

In one embodiment, the gene set is derived either from annotation or specific biological experiments. In one example, the ssGSEA score is a Hereditary Breast Cancer gene set ssGSEA score, wherein the gene set derives from comparing gene expression in hereditary breast cancers (which are enriched for BRCA1/2 loss) and other breast cancers.

In block 360, the GSEA and/or ssGSEA score generation step is optionally tested by generating GSEA and/or ssGSEA scores for individual transcriptomes within the training and/or testing dataset and calculating the correlation between the score for a transcriptome and the DNA-based HRD status associated with the transcriptome. In one example, the training and testing data transcriptomes used for validation are each associated with the same cancer type as the input unknown specimen RNA datasets.

In block 370, at least one output of blocks 315, 345, and 350 are combined in an ensemble model to generate an ensemble predicted HRD score. The DNA-based HRD score of block 303 may also be incorporated into the ensemble model.

In one embodiment, the ensemble model is a linear model. This model takes the direct predictors from the elastic net model, the binarized prediction from the RIDGE regression hypermethylation model (hypermethylated or not), and the GSEA and/or ssGSEA enrichment score of the pathway, plus the DNA-based HRD score (these are the outputs of blocks 315, 345, 350, and 303, respectively).

In one example, a stacked, linear-regression model is trained, incorporating each of these 4 features (outputs of blocks 315, 345, 350, and 303) to distinguish BRCA-intact from BRCA-deficient patients. In one example, this stacked model is highly accurate and outperforms any single RNA- or DNA-based model, identifying many patients missed by DNA models alone who are likely to respond to PARP inhibitors. The success of this model highlights the value of RNA sequencing for the clinical treatment of cancer and the power of integrating multiple sequencing modalities to refine diagnosis, inform prognosis, and deliver the most effective therapies to patients.

In various embodiments, the ensemble model has a low alpha penalty (0.1, L1 regularization), weights HRD positive scores higher (has imbalanced classes), increases lambda (L2 regularization), and/or binarizes the output of the hypermethylation predictor of block 330. "Class imbalance" refers to there being more HRD− than HRD+ samples available, and the weighting is designed to compensate.

In block 390, the ensemble model is optionally validated.

In one example, a specimen RNA dataset and an orthogonal specimen RNA dataset associated with the same specimen are analyzed by the systems and methods disclosed here and the ensemble predicted HRD score generated for the specimen RNA dataset is compared to the ensemble predicted HRD score generated for the orthogonal specimen RNA dataset.

In one example, an orthogonal specimen RNA dataset is generated by processing a specimen by an orthogonal sequencing method to generate (for example, if next-generation sequencing is used to generate the specimen RNA datasets received in block 201, microarray may be used as an orthogonal sequencing method).

In another example, a group of specimens with evidence of genetic BRCA1/2 loss and a group of specimens with BRCA1/2-intact may be analyzed by the systems and methods disclosed herein and another method to generate receiver operating characteristic (ROC) curves and calculate the area under the curve (AUC) for each method. While HRD can occur through other means, patients with genetic loss are definitionally HRD and most HRD is caused by BRCA1/2 loss. In this example, demonstrated that the integrated RNA/DNA model outperformed any single RNA or DNA-based metric (See FIG. 4 for an example).

In block 395, an HRD status report is generated containing the predicted HRD status of the patient specimen or organoid associated with the specimen RNA dataset. The HRD status report may also contain the likelihood of drug sensitivity of cancer cells in the original specimen, especially to drugs that damage DNA, including PARP inhibitors and platinums, and prognostics, including predicted patient survival and/or progression free survival.

The report may be digital (for example, available as a digital file such as a PDF or JPG, or accessible through a user interface such as a portal or website) or it may be a hard copy (for example, printed on paper). The report may be delivered to a physician, medical professional, patient, pharmaceutical designer or manufacturer, or organoid culturing laboratory, especially to guide treatment decisions and design of clinical trials or experiments.

In one example, for each patient specimen in a population that receives RNA sequencing, an RNA-based HRD prediction using each of the three models as described above will be generated. This may be combined in an ensemble model with the DNA-based score. Patients may receive on the report an indicator of whether they were positive for HRD, and if so, may be matched with PARP inhibitor therapy or enrollment in PARP inhibitor trials, especially trials that have positive HRD status as an inclusion criterion. Platinum-based chemotherapy may also be recommended, especially if PARP inhibitors are contraindicated.

These systems and methods may match PARP inhibitors to a greater number of HRD positive patients that can benefit from receiving them, by detecting a greater number of HRD positive patients.

In one embodiment, the final HRD score is a continuous number variable (e.g. a number between 1 and 100). In one example, the HRD score includes a percentile or confidence rating, derived by comparing the HRD score of a single specimen to actual or predicted HRD scores associated with a group of specimens, wherein the group may represent a database, population, cancer type cohort, or other cohort of specimens. The group of specimens may be represented by a histogram and the specimen's position in that histogram may be indicated, for example, by a dotted line or other indicator. In another example, the final HRD score is categorized as low, medium, or high by comparing the final HRD score to a threshold. For example, anything <30 is low, 30-60 is medium, and >60 is high. In one example, these labels are HRD negative (low), HRD ambiguous (medium), and HRD positive (high). In one example, the report may include a cancer type for the specimen. In one example, the report may include a link to a citation, for example a citation describing the systems and methods for calculating the final HRD score disclosed herein, or a citation describing HRD score calculation in general, or a citation describing the basis for matching a therapy to a specimen having a certain HRD score. The report may include information about genetic variants or copy number variants detected in the specimen, especially in BRCA or PALB2 genes.

The report may further include a DNA-based HRD score for the specimen, and a histogram to compare that DNA-based HRD score to a database of DNA-based HRD scores for many specimens.

The report may further include information about the specimen, for example, the collection site, specimen type, tissue type, cancer type, date of collection, tumor percentage, tumor purity, collection method, dissection method, fixation method, etc.

The report may further include information about the methylation status (for example, the name and/or genetic location of the gene(s) and/or promoter(s) associated with the methylation status). The report may further include information about the ssGSEA score (for example, the gene set used to calculate the ssGSEA score).

Figure 6A:
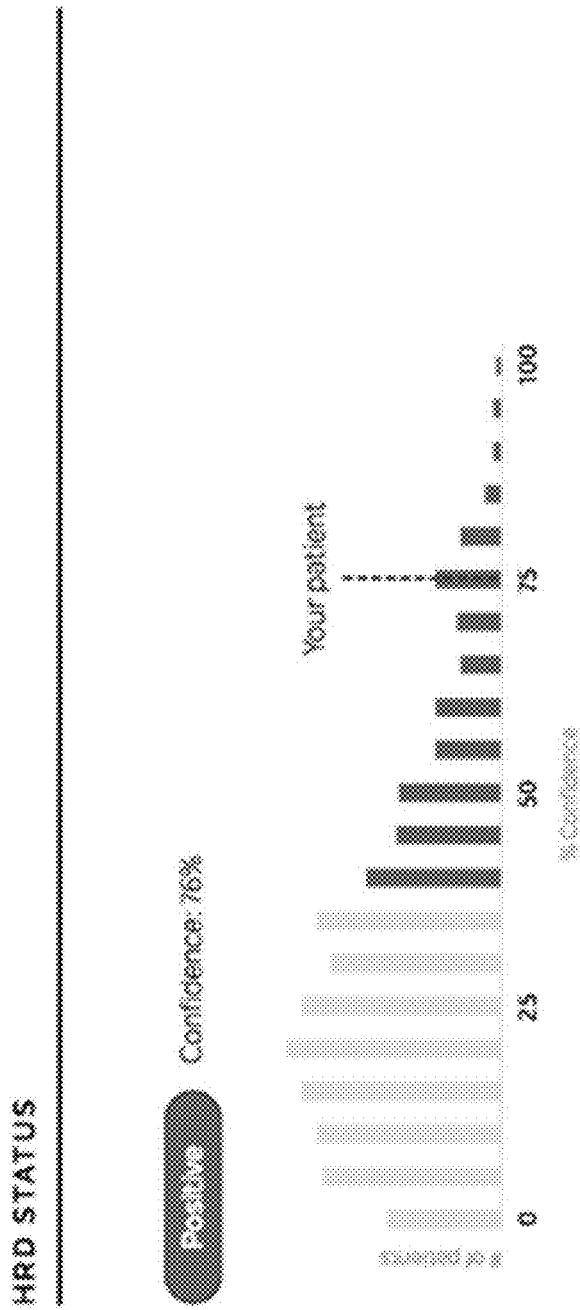
Figure 6B:
Figure 6B:
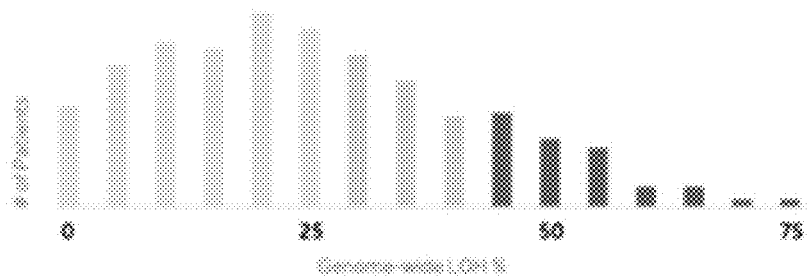

FIGS. 6A, 6B, and 6C collectively illustrate examples of portions of an HRD status report, e.g., as generated in block 395.

FIG. 6A illustrates a positive HRD status and a histogram. In this example, the cutoff (for example, threshold) for a negative versus positive HRD status is 40th percentile and the specimen has an HRD score in the 76th percentile of a database. FIG. 3B illustrates a high HRD status and information about a DNA-based HRD score. FIG. 3C illustrates information about a therapy in the HRD report that was matched based on an HRD score.

Homologous Recombination Deficiency (HRD) is a robust predictor of survival and drug sensitivity (especially to therapeutics that induce DNA-damage, including PARP inhibitors and platinums) in a growing number of cancer types. Unlike normal cells, HRD tumors are unable to repair drug-induced damage, leading to cell death. HRD is defined as the loss of ability to repair DNA damage through the homologous recombination pathway, resulting in genomic instability and certain characteristic copy number alterations (CNAs) that can be used to diagnose HRD.

Prominently, HRD can arise from biallelic loss of BRCA1 or BRCA2 through mutation or promoter hypermethylation. However, alterations in many other DNA repair genes may also be involved, including PALB2 and RAD51, and many more genes likely remain uncharacterized as affecting HRD status. Indeed, BRCA status alone is a relatively weak predictor of HRD status or sensitivity to PARP inhibitors; in most cases, the latter two characteristics are more tightly correlated.

Current methods of diagnosing HRD in a specimen may utilize DNA sequence data, including the detection of variants in BRCA1/2, variants in other genes related to the HR pathway (including PALB2 and RAD51), or CNAs commonly caused by chronic HRD. Due to the stochastic nature of CNA generation, a cell may not acquire CNAs for some time after becoming recombination deficiency (HRD) positive. Even for cells that have acquired CNAs, DNA-based tests may fail to detect HRD cells for many reasons, for example if data are sparse, if the full genome is not covered by the DNA panel, if the panel is biased toward detecting certain portions of a genome over others, or if the result is close to a threshold. Furthermore, analyzing DNA sequence data alone does not detect hypermethylation silencing of HR genes, recombination deficiency (HRD) positive cells that do not have variants in genes related to the HR pathway, or cells that have not acquired CNAs.

In contrast, substantial transcriptome changes can arise shortly after induction of HRD through BRCA1/2 silencing in cellular models, suggesting that some HRD tumors that would be sensitive to PARP inhibitors may exhibit only the transcriptional signature of HRD, not a substantial copy number change burden, and may not be detected by strictly DNA-based tests.

In various embodiments, the systems and methods disclosed herein are one or more algorithms for analyzing RNA-seq data to improve the accuracy of predicting HRD in specimens, especially cancer specimens. The systems and methods may supplement DNA-based measuring of HRD.

In various embodiments, the systems and methods comprise three distinct transcriptome-based predictive models that, when combined with a DNA-based HRD score in an ensemble model, generate more accurate predictions of HRD status with lower rates of false negatives.

In one embodiment, the systems and methods comprise the following transcriptome models: (1) a TCGA-trained transcriptome HRD elastic net, (2) a BRCA1 promoter methylation model, and (3) approximately 100 ssGSEA gene set scores, including a Hereditary Breast Cancer gene set ssGSEA score. In one example, the gene sets are selected for ssGSEA gene set scoring by a LASSO model trained to distinguish BRCA-deficient from BRCA-intact patients.

In one embodiment, the systems and methods include models trained on data related to PARP inhibitor sensitivity, including data derived from tumor organoid models and/or RWE patient data.

In one embodiment, the systems and methods include other machine learning methods (regression trees, support vector machines, etc.). Machine learning models may be trained to perform in the presence of covariates and confounders, including tissue site and tumor purity.

In various embodiments, the systems and methods include an optional analysis of the accuracy of the HRD models in predicting patient survival or response to therapy across tumor types. This analysis may incorporate longitudinal data (including slides and/or outcomes/response data) for patients receiving PARP inhibitors or platinums, or enrolled in clinical trials for these drugs. The analysis may include data generated by tumor-derived organoid experiments, especially experiments that determine whether organoids predicted to have HRD are eliminated or have their growth reduced by PARP inhibitor or platinum-based therapies.

In various embodiments, the systems and methods disclosed herein are for detecting homologous recombination deficiency (HRD) in a specimen by receiving a set of data derived from the specimen and generating an HRD status based on the set of data. In various embodiments, the systems and methods include a medical device that receives a set of data derived from the specimen and generates an HRD status based on the set of data. In various embodiments, the systems and methods include a cloud-based information processing system that receives a set of data derived from the specimen and generates an HRD status based on the set of data. In various embodiments, the systems and methods disclosed herein further include sequencing a cancer specimen by generating a set of data from a cancer specimen; and generating an HRD status based on the set of data. In one example, the medical device is a genetic analyzer system, including a next-generation sequencer, nanopore sequencer, etc. In another example, the medical device is a laboratory developed test. In various embodiments, the set of data includes RNA data, DNA data, and/or methylation data. In various embodiments, the specimen is a cancer specimen from a human patient, an organoid, or an organoid derived from a human cancer specimen.

In various embodiments, the systems and methods disclosed herein further include prescribing or matching a therapy to a specimen, based on the HRD status of the specimen. In one example, the matched therapy is a DNA-damaging therapy, including a poly ADP ribose polymerase (PARP) inhibitor, or a platinum-based chemotherapy.

In various embodiments, the systems and methods disclosed herein further include matching a clinical trial for a specimen, based on the HRD status of the specimen. In one example, the matched clinical trial has inclusion criteria that match the HRD status of the specimen. In another example, the matched clinical trial has exclusion criteria that do not match the HRD status of the specimen.

In various embodiments, the systems and methods disclosed herein further include designing an experiment to test organoid sensitivity to therapy, by matching a therapy based on the HRD status of the specimen, and designing an experiment to monitor the growth of the organoid after exposing the organoid to the matched therapy. In one example, the matched therapy is a DNA-damaging therapy, including a poly ADP ribose polymerase (PARP) inhibitor, or a platinum-based chemotherapy.

It should be noted that details of other processes described herein with respect to other methods described herein (e.g., methods 400 and 500) are also applicable in an analogous manner to method 300 described above. For example, details relating to cancerous biological samples, non-cancerous biological samples, DNA samples, RNA samples, DNA sequencing, RNA sequencing, data normalization, data collection, data processing, classifiers, classifier ensembles, test subjects, associated therapies, etc., described above with reference to method 300 optionally have one or more of the characteristics of the cancerous biological samples, non-cancerous biological samples, DNA samples, RNA samples, DNA sequencing, RNA sequencing, data normalization, data collection, data processing, classifiers, classifier ensembles, test subjects, associated therapies, etc., described herein with reference to other methods described herein (e.g., methods 400 and 500). For brevity, these details are not repeated here.

FIGS. 4 and 5A-C illustrate example workflows 400 and 500 for determining a homologous recombination pathway status of a cancer, where optional steps are indicated by dashed boxes, in accordance with some embodiments of the present disclosure. Further details on various implementation of the steps illustrated in workflows 400 and 500 are described with more particularity below. The skilled artisan will know of suitable alternatives for performing each of the steps shown in workflows 400 and 500.

Referring to Block 500 of FIG. 5, the present disclosure provides a method of determining a homologous recombination pathway status of a cancer in a test subject. In some embodiments, the cancer is breast cancer, ovarian cancer, colorectal cancer, fallopian tube cancer, pancreatic cancer, peritoneal cancer, and/or prostate cancer. In some embodiments, the cancer is associated with a BRCA1, BRCA2, PTEN and/or PALB2 mutation.

Sample Acquisition and Preparation.

In some embodiments, a predicted HRD status is generated based on RNA and/or DNA sequencing data from a tumor tissue sample (e.g., a biopsy), blood samples containing tumor DNA, and/or matched normal samples from a patient. In some embodiments, the tumor tissue sample may be of a cancer of one of many different subtypes, including hematological and solid tumors. In some embodiments, the sample type utilized for comprehensive genomic profiling may be fixed formalin, paraffin embedded (FFPE) slides, peripheral blood, or bone marrow aspirate. The samples may be collected in a repository such a potassium ethylenediaminetetraacetic acid (EDTA) tube. The specimen may be a tissue block or a plurality of FFPE slides, such as up to 3 slides, up to 5 slides, up to 10 slides, or up to 20 slides. In some embodiments, the matched normal specimen is peripheral blood or saliva.

Accordingly, in some embodiments, the method includes obtaining a biological sample from the test subject. For example, as illustrated in Block 402 of FIG. 4, in some embodiments, sample acquisition comprises obtaining a cancer biopsy 452, a liquid biopsy 456, and/or a normal (e.g., healthy) tissue biopsy 454. In some embodiments, the method comprises obtaining a plurality of samples from the test subject (e.g., one or more cancer biopsies, one or more liquid biopsies, and/or one or more normal tissue biopsies). However, in other embodiments, the methods described herein begin by acquiring sequencing data (e.g., raw or pre-processed) and/or patient data constructs formed of the feature data input into an HRD ensemble classifier, as described herein.

As illustrated in Block 404, in some embodiments, a biological sample obtained from the test subject is processed for extraction of nucleic acids and/or library preparation. For example, in some embodiments, a DNA sample is prepared from a solid-tissue tumor biopsy from the subject (e.g., cancerous tissue DNA sample 458 is prepared from cancer biopsy 452). In some embodiments, a DNA sample is prepared from a liquid biopsy from the subject (e.g., cell-free DNA sample 464 is prepared from liquid biopsy 456). In some embodiments, an RNA sample is prepared from a solid-tissue tumor biopsy from the subject (e.g., cancerous tissue RNA/cDNA sample 460 is prepared from cancer biopsy 452).

In some embodiments, a second DNA sample is prepared from a solid-tissue normal biopsy from the subject (e.g., normal tissue DNA sample 462 is prepared from normal tissue biopsy 454).

In some embodiments, a plurality of samples is prepared from each respective cancer biopsy, liquid biopsy, and/or normal tissue biopsy. For example, in some embodiments, a plurality of DNA samples and/or RNA/cDNA samples is prepared from a respective cancer (e.g., solid-tissue tumor) biopsy. In some embodiments, a plurality of DNA samples is prepared from a respective liquid biopsy. In some embodiments, a plurality of DNA samples is prepared from a respective normal tissue biopsy. In some embodiments, a plurality of aliquots is prepared from each respective sample.

In some embodiments, germline ("normal", non-cancerous) DNA may be extracted from either blood (for example, if a patient has cancer that is not a blood cancer) or saliva (for example, if a patient has blood cancer). Normal blood samples may be collected from patients using commercially available blood collection vessels, for example, in PAXgene Blood DNA Tubes, and saliva samples may be collected from patients using commercially available saliva collection vessels, for example, in Oragene DNA Saliva Kits.

Blood cancer samples may be collected from patients (for example, in EDTA collection tubes). Macrodissected FFPE tissue sections (which may be mounted on a histopathology slide) from solid tumor samples may be analyzed by pathologists to determine overall tumor amount in the sample and percent tumor cellularity as a ratio of tumor to normal nuclei. For each section, background tissue may be excluded or removed such that the section meets a tumor purity threshold (in one example, at least 20% of the nuclei in the section are tumor nuclei). Then, DNA may be isolated from blood samples, saliva samples, and tissue sections using commercially available reagents, including proteinase K to generate a liquid solution of DNA.

Each solution of isolated DNA may be subjected to a quality control protocol to determine the concentration and/or quantity of the DNA molecules in the solution, which may include the use of a fluorescent dye and a fluorescence microplate reader, standard spectrofluorometer, or filter fluorometer.

For each cancer sample and each normal sample, isolated DNA molecules may be mechanically sheared to an average length using an ultrasonicator (for example, a Covaris ultrasonicator). The DNA molecules may also be analyzed to determine their fragment size, which may be done through gel electrophoresis techniques and may include the use of a device such as a LabChip GX Touch.

DNA libraries may be prepared from the isolated DNA, for example, using the KAPA Hyper Prep Kit, a New England Biolabs (NEB) kit, or a similar kit. DNA library preparation may include the ligation of adapters onto the DNA molecules. For example, UDI adapters, including Roche SeqCap dual end adapters, or UMI adapters (for example, full length or stubby Y adapters) may be ligated to the DNA molecules.

Similarly, methods for isolating RNA, e.g., mRNA, from tissue samples are known in the art. In some embodiments, isolated RNA is then reverse transcribed into cDNA, from which cDNA/RNA libraries can be prepared in an analogous fashion as the DNA libraries described below.

In some embodiments, adapters are used during DNA/cDNA library construction. Adaptors are nucleic acid molecules that may serve as barcodes to identify DNA/cDNA molecules according to the sample from which they were derived and/or to facilitate the downstream bioinformatics processing and/or the next generation sequencing reaction. The sequence of nucleotides in the adapters may be specific to a sample in order to distinguish samples. The adapters may facilitate the binding of the DNA/cDNA molecules to anchor oligonucleotide molecules on the sequencer flow cell and may serve as a seed for the sequencing process by providing a starting point for the sequencing reaction.

DNA/cDNA libraries may be amplified and purified using reagents, for example, Axygen MAG PCR clean up beads. Then the concentration and/or quantity of the DNA/cDNA molecules may be quantified using a fluorescent dye and a fluorescence microplate reader, standard spectrofluorometer, or filter fluorometer.

DNA/cDNA libraries may be pooled (two or more DNA/cDNA libraries may be mixed to create a pool) and treated with reagents to reduce off-target capture, for example Human COT-1 and/or IDT xGen Universal Blockers. Pools may be dried in a vacufuge and resuspended. DNA libraries or pools may be hybridized to a probe set (for example, a probe set specific to a panel that includes approximately 100, 600, 1,000, 10,000, etc. of the 19,000 known human genes) and amplified with commercially available reagents (for example, the KAPA HiFi HotStart ReadyMix).

Pools may be incubated in an incubator, PCR machine, water bath, or other temperature modulating device to allow probes to hybridize. Pools may then be mixed with Streptavidin-coated beads or another means for capturing hybridized DNA/cDNA-probe molecules, such as DNA molecules representing exons of the human genome and/or genes selected for a genetic panel.

Pools may be amplified and purified more than once using commercially available reagents, for example, the KAPA HiFi Library Amplification kit and Axygen MAG PCR clean up beads, respectively. The pools or DNA/cDNA libraries may be analyzed to determine the concentration or quantity of DNA/cDNA molecules, for example by using a fluorescent dye (for example, PicoGreen pool quantification) and a fluorescence microplate reader, standard spectrofluorometer, or filter fluorometer.

In one example, a DNA/cDNA library preparation and/or whole exome capture steps may be performed with an automated system, using a liquid handling robot (for example, a SciClone NGSx).

Nucleic Acid Sequencing.

The library amplification may be performed on a device, for example, an Illumina C-Bot2, and the resulting flow cell containing amplified target-captured DNA/cDNA libraries may be sequenced on a next generation sequencer, for example, an Illumina HiSeq 4000 or an Illumina NovaSeq 6000 to a unique on-target depth selected by the user, for example, 300×, 400×, 500×, 10,000×, etc. Samples may be further assessed for uniformity with each sample required to have 95% of all targeted bp sequenced to a minimum depth selected by the user, for example, 300×. The next generation sequencer may generate a FASTQ, BCL, or other file for each flow cell or each patient sample.

Accordingly, referring to Blocks 502 and 504 of FIG. 5, in some embodiments, the method includes sequencing a DNA sample from a cancerous tissue of the test subject and/or an RNA sample from the cancerous tissue of the test subject.

Figure 4:
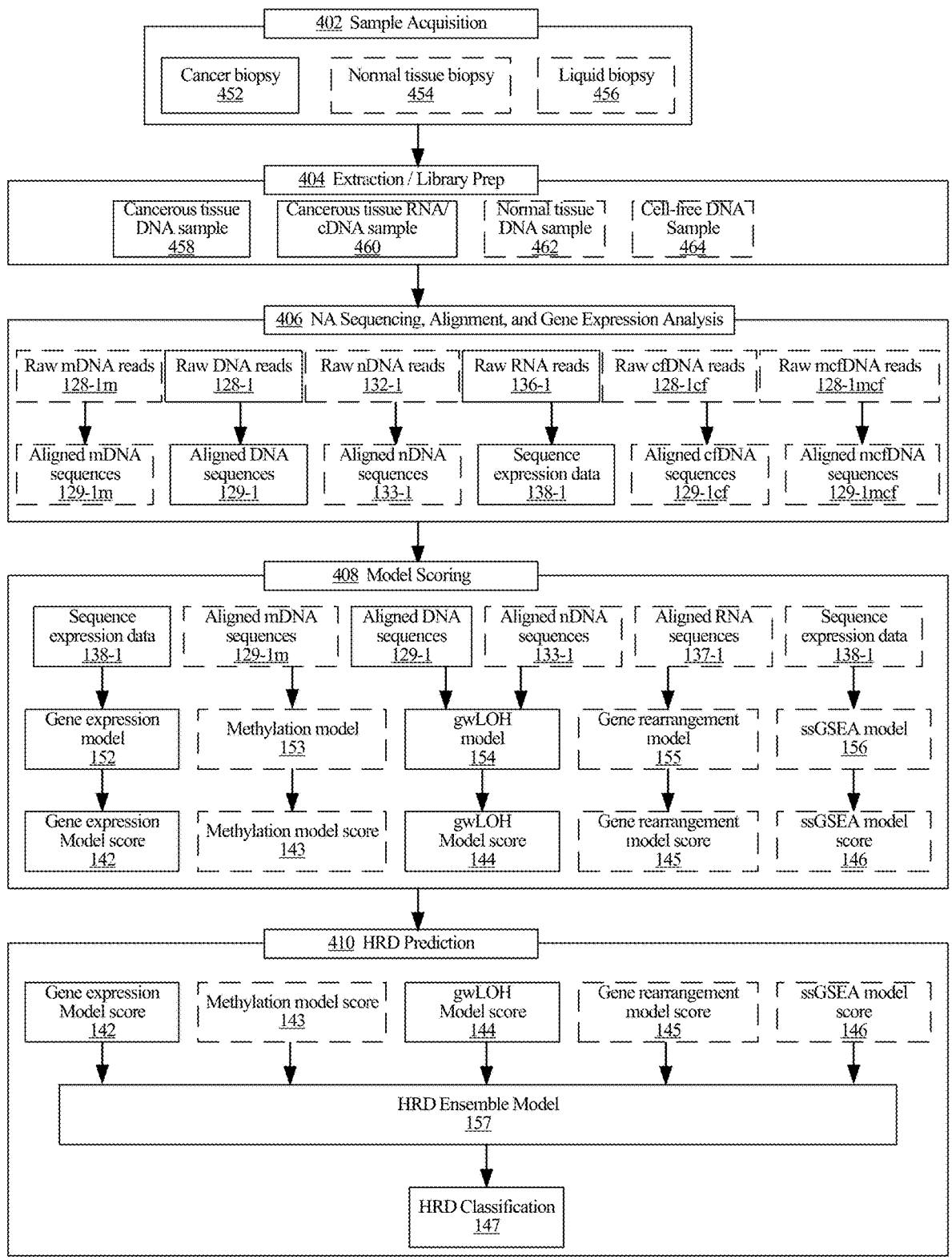
FIG. 4 provides a flow chart of an example method 400 for using information derived from DNA sequencing and RNA sequencing of cancerous tissue to predict the homologous recombination status of a cancer, in accordance with some embodiments of the present disclosure.
Figure 5A:
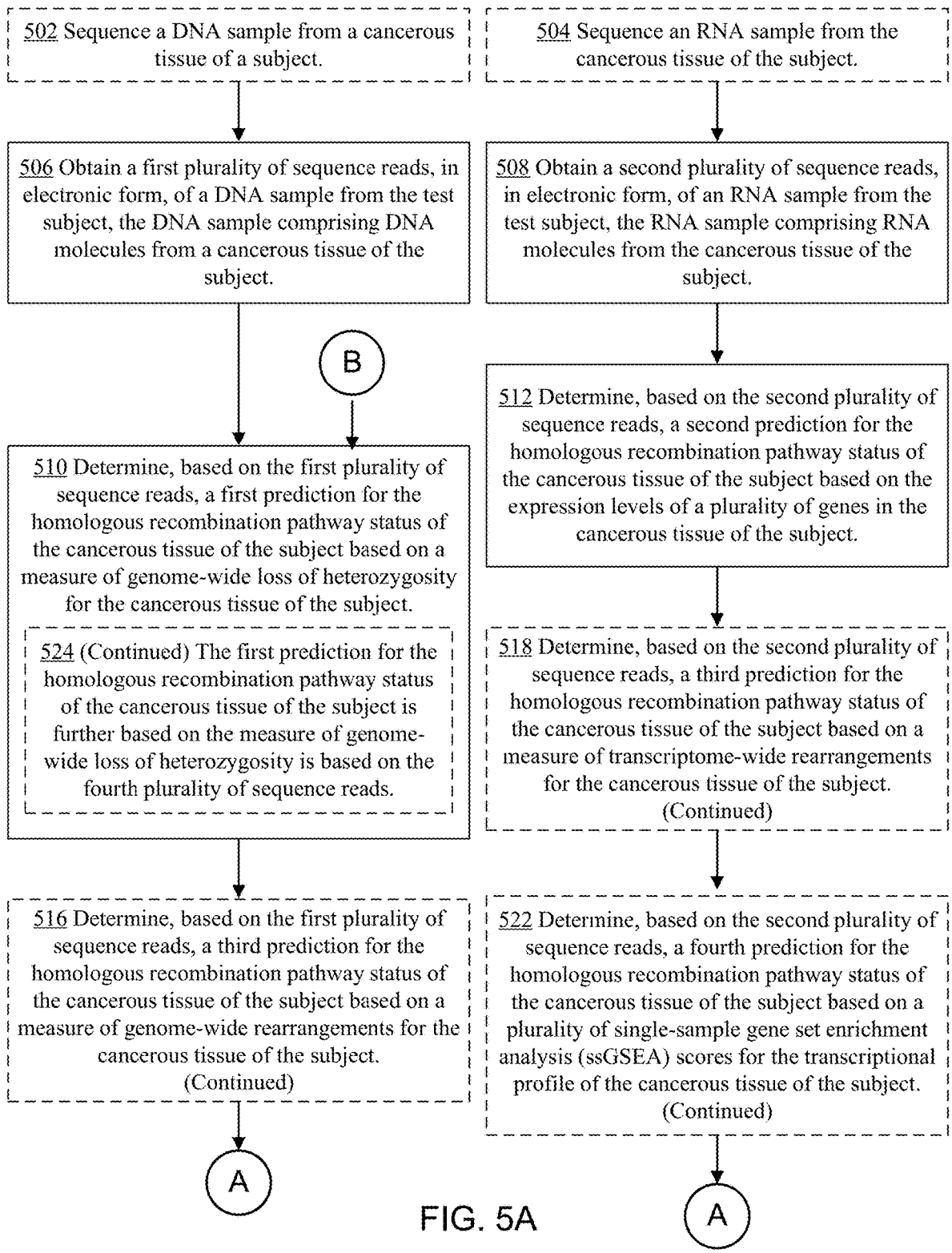
Figure 5B:
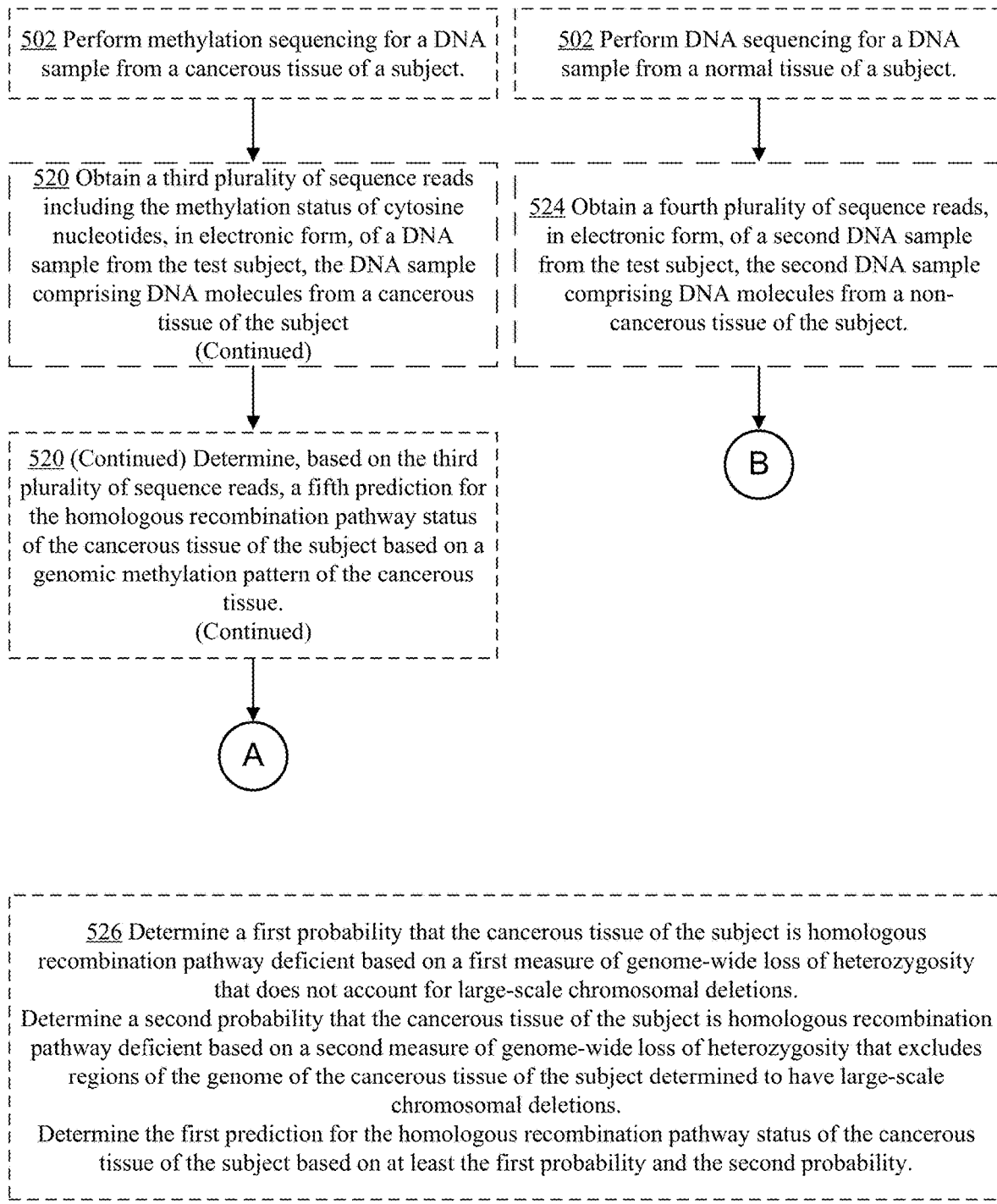

For example, as illustrated in Block 406 of FIG. 4, in some embodiments, one or more samples obtained from a tissue of a subject (e.g., cancerous tissue DNA sample 458, cancerous tissue RNA/cDNA sample 460, normal tissue DNA sample 462, and/or cell-free DNA sample 464) are further processed for nucleic acid sequencing, alignment, and/or gene expression analysis. For instance, in some embodiments, a DNA sample is sequenced using a targeted-panel DNA sequencing reaction. In some such embodiments, the targeted-panel DNA sequencing reaction uses a plurality of nucleic acid probes to enrich nucleic acids from the cancerous tissue of the subject, for a panel of genomics regions). In some embodiments, a DNA sample is sequenced using a low-pass whole genome sequencing reaction. In some such embodiments, the average sequencing coverage across the genome is less than 3×, less than 2.5×, less than 2×, less than 1.5×, less than 1×, less than 0.75×, or lower. In some embodiments, the DNA sequencing reaction generates a plurality of sequence reads (e.g., raw DNA reads obtained from a cancerous tissue DNA sample 128-1, raw DNA reads obtained from a normal tissue DNA sample (nDNA) 132-1, and/or raw cell-free DNA reads obtained from a cell-free DNA sample (cfDNA) 128-1$cf$).

In some embodiments, an RNA sample is sequenced by a whole-exome sequencing reaction. In some embodiments, an RNA sample is sequenced by a targeted-panel RNA sequencing reaction. In some embodiments, the RNA sequencing reaction generates a plurality of sequence reads (e.g., raw RNA reads obtained from a cancerous tissue RNA/cDNA sample 136-1).

In some embodiments, a DNA sample (e.g., obtained from a solid-tissue tumor biopsy, a liquid biopsy, and/or a normal tissue biopsy) is sequenced by a methylation sequencing reaction (e.g., bisulfite sequencing). In some embodiments, the methylation sequencing reaction generates a plurality of sequence reads (e.g., raw methylation DNA reads (mDNA) obtained from a cancerous tissue DNA sample 128-1$m$ and/or raw methylation DNA reads obtained from a cell-free DNA sample (mcfDNA) 128-1$mcf$).

In some embodiments, a first sequencing reaction and a second sequencing reaction are performed using different aliquots of the same sample (e.g., a DNA sample comprising the DNA molecules from the cancerous tissue of the subject). For example, in some embodiments, a DNA sample is divided into two aliquots, the first aliquot is used for a DNA sequencing reaction (e.g., targeted-panel or whole genome), and the second aliquot is used for a bisulfite sequencing reaction.

In some embodiments, a first sequencing reaction and a second sequencing reaction are performed using a corresponding first sample (e.g., a first DNA sample) and a corresponding second sample (e.g., a second DNA sample obtained from the same tissue biopsy as the first DNA sample).

Referring to Block 506 of FIG. 5, the method further includes obtaining a first plurality of sequence reads, in electronic form, of a DNA sample from the test subject, the DNA sample comprising DNA molecules from a cancerous tissue of the subject (e.g., raw DNA reads 128-1 and/or raw cfDNA reads 128-1$cf$). In some embodiments, the first plurality of sequence reads is generated from a targeted-panel DNA sequencing reaction or a low-pass whole genome sequencing reaction. In some embodiments, the first plurality of sequence reads comprises at least 10,000 sequence reads. In some embodiments, the first plurality of sequence reads comprises at least 100,000 sequence reads. In some embodiments, the first plurality of sequence reads comprises at least 1,000,000 sequence reads. In some embodiments, the first plurality of sequence reads comprises at least 5,000,000 sequence reads. In some embodiments, the first plurality of sequence reads comprises at least 10,000,000 sequence reads. In some embodiments, the first plurality of sequence reads includes from 100,000 sequence reads to 100,000,000 sequence reads. In some embodiments, the first plurality of sequence reads includes from 500,000 sequence reads to 50,000,000 sequence reads.

Referring to Block 508, the method further includes obtaining a second plurality of sequence reads, in electronic form, of an RNA sample from the test subject, the RNA sample comprising RNA molecules from the cancerous tissue of the subject (e.g., raw RNA reads 136-1). In some embodiments, the second plurality of sequence reads is generated from a whole-exome sequencing reaction or a targeted-panel RNA sequencing reaction. In some embodiments, the second plurality of sequence reads comprises at least 10,000 sequence reads. In some embodiments, the second plurality of sequence reads comprises at least 100,000 sequence reads. In some embodiments, the second plurality of sequence reads comprises at least 1,000,000 sequence reads. In some embodiments, the second plurality of sequence reads comprises at least 5,000,000 sequence reads. In some embodiments, the second plurality of sequence reads comprises at least 10,000,000 sequence reads. In some embodiments, the second plurality of sequence reads includes from 100,000 sequence reads to 100,000,000 sequence reads. In some embodiments, the second plurality of sequence reads includes from 500,000 sequence reads to 50,000,000 sequence reads.

In some embodiments, the method further comprises obtaining a third plurality of sequence reads comprising the methylation status of cytosine nucleotides, in electronic form, of a DNA sample from the test subject, the DNA sample comprising DNA molecules from a cancerous tissue of the subject (e.g., raw mDNA reads 128-1$m$ and/or raw mcfDNA reads 128-1$mcf$). In some embodiments, the third plurality of sequence reads was generated by bisulfite sequencing. In some embodiments, the first plurality of sequence reads and the third plurality of sequence reads were generated using different aliquots of the same DNA sample comprising the DNA molecules from the cancerous tissue of the subject. In some embodiments, the third plurality of sequence reads comprises at least 10,000 sequence reads. In some embodiments, the third plurality of sequence reads comprises at least 100,000 sequence reads. In some embodiments, the third plurality of sequence reads comprises at least 1,000,000 sequence reads. In some embodiments, the third plurality of sequence reads comprises at least 5,000,000 sequence reads. In some embodiments, the third plurality of sequence reads comprises at least 10,000,000 sequence reads. In some embodiments, the third plurality of sequence reads includes from 100,000 sequence reads to 100,000,000 sequence reads. In some embodiments, the third plurality of sequence reads includes from 500,000 sequence reads to 50,000,000 sequence reads.

In some embodiments, the method further comprises obtaining a fourth plurality of sequence reads, in electronic form, of a second DNA sample from the test subject, the second DNA sample comprising DNA molecules from a non-cancerous (e.g., normal) tissue of the subject (e.g., raw nDNA reads 132-1). In some embodiments, the fourth plurality of sequence reads comprises at least 10,000 sequence reads. In some embodiments, the fourth plurality of sequence reads comprises at least 100,000 sequence reads. In some embodiments, the fourth plurality of sequence reads comprises at least 1,000,000 sequence reads. In some embodiments, the fourth plurality of sequence reads comprises at least 5,000,000 sequence reads. In some embodiments, the fourth plurality of sequence reads comprises at least 10,000,000 sequence reads. In some embodiments, the fourth plurality of sequence reads includes from 100,000 sequence reads to 100,000,000 sequence reads. In some embodiments, the fourth plurality of sequence reads includes from 500,000 sequence reads to 50,000,000 sequence reads.

In some embodiments, referring again to Block 406, a plurality of sequence reads (e.g., the first, third, and/or fourth plurality of sequence reads (DNA)) is aligned to a reference sequence and/or a reference genome (e.g., aligned DNA sequences 129-1, aligned cfDNA sequences 129-1cf, aligned mDNA sequences 129-1m, aligned mcfDNA sequences 129-1mcf, and/or aligned nDNA sequences 133-1).

In some embodiments, a plurality of sequence reads (e.g., the second plurality of sequence reads (RNA)) are used to perform gene expression analysis (e.g., sequence expression data 138-1). In some embodiments, the gene expression analysis comprises transcriptome analysis, gene set expression analysis (GSEA), microarrays, RNAseq, qPCR, and/or fluorescent in situ hybridization.

In some embodiments, a plurality of sequence reads (e.g., raw sequence reads, aligned sequences, and/or sequence expression data) is stored in a data store. For instance, referring to FIG. 1B, in some embodiments, the data store is a subject data construct for each subject 122 in a test subject database 120. In some embodiments, the obtaining a plurality of sequence reads (e.g., the first, second, third, and/or fourth plurality of sequence reads) comprises obtaining the plurality of sequence reads from a data store. In some embodiments, the obtaining a plurality of sequences comprises obtaining a plurality of raw sequence reads. In some embodiments, the obtaining a plurality of sequence reads comprises obtaining a plurality of aligned sequences and/or sequence expression data.

Model Scoring.

Referring to Block 510 of FIG. 5, the method further includes determining, based on the first plurality of sequence reads, a first prediction for the homologous recombination pathway status of the cancerous tissue of the subject based on a measure of genome-wide loss of heterozygosity for the cancerous tissue of the subject.

For instance, as illustrated in Block 408 of FIG. 4, the determining the first prediction comprises obtaining a model score using a model. In some such embodiments, the model scoring comprises obtaining a plurality of aligned DNA sequences 129-1 (e.g., from a cancerous tissue DNA sample), applying the plurality of aligned DNA sequences to a genome-wide loss of heterozygosity (gwLOH) model 154, and obtaining a gwLOH model score 144, thus obtaining the first prediction based on the measure of gwLOH for the cancerous tissue of the subject.

Referring to Block 524, in some embodiments, the method further includes obtaining a fourth plurality of sequence reads, in electronic form, of a second DNA sample from the test subject, the second DNA sample comprising DNA molecules from a non-cancerous tissue of the subject (as described above; see "Nucleic acid sequencing"), and determining the first prediction based on the first plurality of sequence reads and the fourth plurality of sequence reads.

For example, as illustrated in Block 408, in some embodiments, the model scoring comprises obtaining a plurality of aligned DNA sequences 129-1 (e.g., from a cancerous tissue DNA sample) and a plurality of aligned nDNA sequences 133-1 (e.g., from a normal tissue DNA sample), applying the plurality of aligned DNA sequences and the plurality of aligned nDNA sequences to a genome-wide loss of heterozygosity (gwLOH) model 154, and obtaining a gwLOH model score 144, thus obtaining the first prediction based on the measure of gwLOH for the cancerous tissue of the subject and the non-cancerous tissue of the subject.

In some embodiments, the determining the first prediction is further based on a cancer type of the cancerous tissue of the subject.

Referring to Block 526, in some embodiments, the determining the first prediction further includes determining a first probability that the cancerous tissue of the subject is homologous recombination deficiency (HRD) positive based on a first measure of genome-wide loss of heterozygosity that does not account for whole-arm or whole-chromosome deletions, determining a second probability that the cancerous tissue of the subject is homologous recombination deficiency (HRD) positive based on a second measure of genome-wide loss of heterozygosity that excludes regions of the genome of the cancerous tissue of the subject determined to have whole-arm or whole-chromosome deletions, and determining the first prediction for the homologous recombination pathway status of the cancerous tissue of the subject based on at least the first probability and the second probability.

Referring to Block 512, the method further includes determining, based on the second plurality of sequence reads, a second prediction for the homologous recombination pathway status of the cancerous tissue of the subject based on the expression levels of a plurality of genes in the cancerous tissue of the subject.

For example, as illustrated in Block 408, in some embodiments, the model scoring comprises obtaining sequence expression data 138-1 (e.g., from a cancerous tissue RNA/cDNA sample), applying the sequence expression data to a gene expression model 152, and obtaining a gene expression model score 142, thus obtaining the second prediction based on the measure of expression levels of a plurality of genes in the cancerous tissue of the subject.

In some embodiments, the determining the second prediction is based on expression values, determined from the second plurality of sequence reads, for at least 100 genes. In some embodiments, the determining the second prediction is based on expression values, determined from the second plurality of sequence reads, for at least 1000 genes. In some embodiments, the determining the second prediction is based on expression values, determined from the second plurality of sequence reads, for at least 10, at least 20, at least 50, at least 100, at least 200, at least 300, at least 400, at least 500, at least 600, at least 700, at least 800, at least 900, at least 1000, at least 2000, at least 3000, at least 4000, at least 5000, at least 10,000, at least 20,000, or at least 30,000 genes.

Referring to Block 514, the method includes generating a subject data construct comprising (i) the first prediction for the homologous recombination pathway status of the cancerous tissue of the subject and (ii) the second prediction for the homologous recombination pathway status of the cancerous tissue of the subject. In some embodiments, the subject data construct is stored for each subject 122 in a test subject database 120.

Referring to Block 516, in some embodiments, the method further includes determining, based on the first plurality of sequence reads, a third prediction for the homologous recombination pathway status of the cancerous tissue of the subject based on a measure of genome-wide rearrangements for the cancerous tissue of the subject. The subject data construct further comprises the third prediction for the homologous recombination pathway status of the cancerous tissue of the subject. In some embodiments, the measure of genome-wide rearrangements is a measure of sequence insertions, sequence deletions, sequence inversions, and sequence translocations identified in the first plurality of sequence reads. In some embodiments, the determining the third prediction is further based on a cancer type of the cancerous tissue of the subject.

Referring to Block 518, in some embodiments, the method further includes determining, based on the second plurality of sequence reads, a third prediction for the homologous recombination pathway status of the cancerous tissue of the subject based on a measure of transcriptome-wide rearrangements for the cancerous tissue of the subject. The subject data construct further comprises the third prediction for the homologous recombination pathway status of the cancerous tissue of the subject. In some embodiments, the measure of transcriptome-wide rearrangements is a measure of sequence insertions, sequence deletions, sequence inversions, and sequence translocations identified in the second plurality of sequence reads.

For example, as illustrated in Block 408, the model scoring comprises obtaining a plurality of aligned RNA sequences 137-1 (e.g., from a cancerous tissue RNA/cDNA sample), applying the plurality of aligned RNA sequences to a gene rearrangement model 155, and obtaining a gene rearrangement model score 145, thus obtaining the third prediction based on the measure of transcriptome-wide rearrangements for the cancerous tissue of the subject.

Referring to Block 522, in some embodiments, the method further includes determining, based on the second plurality of sequence reads, a fourth prediction for the homologous recombination pathway status of the cancerous tissue of the subject based on a plurality of single-sample gene set enrichment analysis (ssGSEA) scores for the transcriptional profile of the cancerous tissue of the subject. The subject data construct further comprises the fourth prediction for the homologous recombination pathway status of the cancerous tissue of the subject. In some embodiments, the plurality of single-sample gene set enrichment analysis (ssGSEA) scores is at least 10 ssGSEA scores. In some embodiments, the plurality of single-sample gene set enrichment analysis (ssGSEA) scores is at least 50 ssGSEA scores. In some embodiments, the plurality of single-sample gene set enrichment analysis (ssGSEA) scores is at least 100 ssGSEA scores. In some embodiments, the plurality of single-sample gene set enrichment analysis (ssGSEA) scores is at least 1000 ssGSEA scores. In some embodiments, the plurality of single-sample gene set enrichment analysis (ssGSEA) scores is at least 20, at least 50, at least 100, at least 200, at least 300, at least 400, at least 500, at least 600, at least 700, at least 800, at least 900, at least 1000, at least 2000, at least 3000, at least 4000, at least 5000, at least 10,000, at least 20,000, or at least 30,000 ssGSEA scores.

For instance, as illustrated in Block 408, the model scoring comprises obtaining sequence expression data 138-1 (e.g., from a cancerous tissue RNA/cDNA sample), applying the sequence expression data to a single-sample GSEA model 156, and obtaining an ssGSEA model score 146, thus obtaining the fourth prediction based on the transcriptional profile of the cancerous tissue of the subject.

In some embodiments, the determining the fourth prediction is further based on a cancer type of the cancerous tissue of the subject.

Referring to Block 520, in some embodiments, the method further includes obtaining a third plurality of sequence reads comprising the methylation status of cytosine nucleotides, in electronic form, of a DNA sample from the test subject, the DNA sample comprising DNA molecules from a cancerous tissue of the subject (as described above; see "Nucleic acid sequencing"). Based on the third plurality of sequence reads, a fifth prediction for the homologous recombination pathway status of the cancerous tissue of the subject is determined, based on a genomic methylation pattern of the cancerous tissue. The subject data construct further comprises the one or more methylation scores (e.g., the fifth prediction) for the cancerous tissue.

In some embodiments, the third plurality of sequence reads is obtained using a methylation sequencing (e.g., bisulfite sequencing). In some embodiments, the third plurality of sequence reads is aligned to a reference sequence (e.g., a reference genome). In some embodiments, the third plurality of sequence reads comprises a genomic methylation pattern, based on an alignment of the third plurality of sequence reads to the reference genome.

In some embodiments, the fifth prediction for the homologous recombination pathway status of the cancerous tissue of the subject comprises one or more methylation scores for the cancerous tissue. In some embodiments, a methylation score in the one or more methylation scores is a beta-value and/or an M-value (see, for example, Du et al., "Comparison of Beta-value and M-value methods for quantifying methylation levels by microarray analysis," BMC Bioinf. 2020, 11:587, which is hereby incorporated herein by reference in its entirety.

In some embodiments, the genomic methylation pattern of the cancerous tissue comprises a methylation pattern for a promoter region of a homologous recombination gene. In some embodiments, the genomic methylation pattern of the cancerous tissue comprises a methylation pattern for at least 100 genomic regions. In some embodiments, the genomic methylation pattern of the cancerous tissue comprises a methylation pattern for at least 1000 genomic regions. In some embodiments, the genomic methylation pattern of the cancerous tissue comprises a methylation pattern for at least 10, at least 20, at least 50, at least 100, at least 200, at least 300, at least 400, at least 500, at least 600, at least 700, at least 800, at least 900, at least 1000, at least 2000, at least 3000, at least 4000, at least 5000, at least 10,000, or at least 50,000 genomic regions.

In some embodiments, the determining the fifth prediction is further based on a cancer type of the cancerous tissue of the subject.

For instance, as illustrated in Block 408, the model scoring comprises obtaining aligned methylation DNA (mDNA) sequences 129-1*m* (e.g., from a cancerous tissue DNA sample). In some embodiments, the plurality of aligned mDNA sequences 129-1*m* and the plurality of aligned DNA sequences 129-1 are obtained from a first aliquot and a second aliquot, respectively, of a respective DNA sample comprising DNA molecules from a cancerous tissue of the subject. In some embodiments, the plurality of aligned mDNA sequences is applied to a methylation model 153, and a methylation model score 143 is obtained, thus obtaining the fifth prediction based on the genomic methylation pattern of the cancerous tissue using the third plurality of sequence reads.

In some embodiments, a model used for obtaining one or more model scores (e.g., a gene expression model, a methylation model, a gwLOH model, a gene rearrangement model, and/or an ssGSEA model) is a logistic regression algorithm, a neural network algorithm, a support vector machine algorithm, a Naive Bayes algorithm, a nearest neighbor algorithm, a boosted trees algorithm, a random forest algorithm, a decision tree algorithm, a multinomial logistic regression algorithm, a linear model, or a linear regression algorithm.

HRD Prediction.

Referring to Block 528 of FIG. 5, the method further includes inputting the subject data construct into an ensemble model trained to distinguish between cancers with homologous recombination pathway deficiencies and cancers without homologous recombination pathway deficiencies, thus determining the homologous recombination pathway status of the test subject.

For example, referring to Block 410 of FIG. 4, a method for homologous recombination pathway deficiency (HRD) comprises inputting a subject data construct into an HRD ensemble model 157. The HRD ensemble model 157 provides an HRD classification 147, which determined whether the cancer in the test subject is homologous recombination deficiency (HRD) positive or is not homologous recombination deficiency (HRD) positive.

In some embodiments, the subject data construct includes the first prediction for the homologous recombination pathway status of the cancerous tissue of the subject (e.g., the gwLOH model score 144). In some embodiments, the subject data construct includes the second prediction for the homologous recombination pathway status of the cancerous tissue of the subject (e.g., the gene expression model score 142).

In some embodiments, the subject data construct includes a third prediction for the homologous recombination pathway status of the cancerous tissue of the subject based on a measure of genome-wide rearrangements for the cancerous tissue of the subject using the first plurality of sequence reads (e.g., DNA sequence reads).

In some embodiments, the subject data construct includes a third prediction for the homologous recombination pathway status of the cancerous tissue of the subject based on a measure of transcriptome-wide rearrangements for the cancerous tissue of the subject (e.g., the gene rearrangement model score 145) using the second plurality of sequence reads (e.g. RNA sequence reads).

In some embodiments, the subject data construct comprises a fourth prediction based on a plurality of single-sample gene set enrichment analysis (ssGSEA) scores for the transcriptional profile of the cancerous tissue of the subject (e.g., the ssGSEA model score 146) using the second plurality of sequence reads (e.g., RNA sequence reads).

In some embodiments, the subject data construct comprises a fifth prediction for the homologous recombination pathway status of the cancerous tissue of the subject (e.g., the methylation model score 143) based on a genomic methylation pattern of the cancerous tissue, using the third plurality of sequence reads (e.g., methylation DNA sequence reads).

Meta-learning or ensemble learning is an artificial intelligence algorithm development strategy that combines multiple classes of algorithms in an efficient way of performing a classification task. See, for example, Zhou, 2012, "Ensemble Methods: Foundations and Algorithms," Chapman Hall; Vilalta and Drissi, "A Perspective View and Survey of Meta-Learning," Artificial Intelligence Review 18(2):77-95; Chan and Stolfo, 1995, "A comparative evaluation of voting and meta-learning on partitioned data," paper presented at ICML1995; and Seewald and Fürnkranz, "An Evaluation of Grading Classifiers," in Hoffmann et al., *Advances in Intelligent Data Analysis: 4th International Conference*, IDA 2001 Cascais, Portugal, Sep. 13-15, 2001 Proc. Springer Berlin Heidelberg; 2001:115-124, each of which is hereby incorporated herein by reference in its entirety.

Binary prediction learning algorithms comprising singleton algorithms using relatively small numbers (e.g., 100 cases per group or less) are prone to overfitting. See Rokach, 2010, *Pattern Classification Using Ensemble Methods*, World Scientific Publishing Co., Inc.; and Frey et al., 2014, "Big Data Deep Phenotyping: Contribution of the IMIA Genomic Medicine Working Group," Yearbook of Medical Informatics 9(1):206-211, each of which is hereby incorporated herein by reference in its entirety. There are multiple ways to improve these situations including improvement of single algorithms. These include bagging, boosting, or both. In some embodiments, classifiers are improved by using multiple independent learners, evaluating the results of each learner based on concordance estimations, running the prediction task and gathering final results based on approximations from individual learners. See, for example, Breiman, "Bagging predictors," Machine Learning 24(2):123-140; Freund, 1995, "Boosting a weak learning algorithm by majority," Inf. Comput. 121(2):256-285; Alceu et al., 2014 "Dynamic selection of classifiers-A comprehensive review," Pattern Recogn. 47(11):3665-3680; and Micha et al., 2014 "A survey of multiple classifier systems as hybrid systems, Inf. Fusion 16:3-17, each of which is hereby incorporated herein by reference in its entirety.

In some embodiments, ensemble models comprise one or more chains of classifiers (e.g., models or learners), where the output of a first classifier is used as an input in a second classifier in the downstream classification cascade. By using a combination of classifiers, a relatively small patient population can be used to produce a trained ensemble classifier that has a high degree of accuracy. This is advantageous because large training populations can be difficult to obtain, such as when sample acquisition involves invasive procedures, limited patient access, and/or rare or precious sample specimens.

Thus, in some embodiments, an ensemble learning strategy (e.g., an ensemble model) is employed for classification of homologous recombination pathway status of a test subject. In some embodiments, the ensemble model comprises a majority voting method and/or a concordance method. In some embodiments, the ensemble model further comprises a k-fold cross validation approach to assessing sample-induced bias and error rates.

In some embodiments, the ensemble model incorporates inputs (e.g., model scores) obtained from one or more models (e.g., a gene expression model, a methylation model, a gwLOH model, a gene rearrangement model, and/or an ssGSEA model), where each respective model in the one or more models is a logistic regression algorithm, a neural network algorithm, a support vector machine algorithm, a Naive Bayes algorithm, a nearest neighbor algorithm, a boosted trees algorithm, a random forest algorithm, a decision tree algorithm, a multinomial logistic regression algorithm, a linear model, or a linear regression algorithm. In some embodiments, the HRD classification is obtained using a voting method.

Downstream Applications.

Referring to Block 530, in some embodiments, the method further includes, when it is determined that the cancer in the test subject is homologous recombination deficiency (HRD) positive, treating the cancer by administering a poly ADP ribose polymerase (PARP) inhibitor to the test subject, and, when it is determined the cancer in the test subject is not homologous recombination deficiency (HRD) positive, treating the cancer with a therapy that does not include administration of a PARP inhibitor to the test subject.

In some embodiments, the PARP inhibitor is selected from the group consisting of olaparib, veliparib, rucaparib, niraparib, and talazoparib. In some embodiments, the PARP inhibitor is olaparib, veliparib, rucaparib, niraparib, talazoparib, pamiparib, 2 X-121/Stenoparib, CEP-9722, CEP-8983, E7016, iniparib, and/or 3-aminobenzamide. In some embodiments, treatment with the PARP inhibitor is administered in combination with a radiotherapy.

In some embodiments, the PARP inhibitor is administered as monotherapy, e.g., in the absence of any other cancer treatment. In some embodiments, the PARP inhibitor is administered in combination with a chemotherapy. In some embodiments, the PARP inhibitor is administered in combination with an immunotherapy. In some embodiments, the PARP inhibitor is administered in combination with an inhibitor of a downstream or alternative oncogenic signaling pathway. The PARP inhibitor and second, non-PARP inhibitor therapy may be administered at the same time (concurrently), each treatment may only partially overlap in time (staggered), or one therapy regimen may end before the other starts. Either the PARPi or non-PARPi may be first.

In some embodiments, when the cancer is predicted to be HRD positive, the subject is administered a combination therapy that includes a PARP inhibitor and a second, non-PARP inhibitor therapy, e.g., a chemotherapy, an immunotherapy, a signaling pathway inhibitor, or radiation; and when the cancer is predicted to be HRD negative, the subject is administered only the second, non-PARP inhibitor therapy, e.g., a chemotherapy, an immunotherapy, a signaling pathway inhibitor, or radiation.

In some aspects, a report is generated, e.g., to provide clinical support for personalized cancer therapy to a medical professional, that includes the HRD status results determined according to the methods described herein. In some embodiments, the report includes comprehensive genomic profiling information, such as information about the mutational status of a patient's cancer, as well as an estimate of HRD status. In some aspects, genes reported in the comprehensive genomic profiling information may be highlighted as underlying or otherwise related to the estimate of HRD status. The number of such genes may be between 1-5, between 1-10, between 1-20, between 1-30, between 1-40, between 1-50, and so forth. In some aspects, the genes reported as mutated in the comprehensive genomic profiling information may be highlighted as being germline or somatic alterations, where detected.

It should be noted that details of other processes described herein with respect to other methods described herein (e.g., methods 300 and 500) are also applicable in an analogous manner to method 400 described above. For example, details relating to cancerous biological samples, non-cancerous biological samples, DNA samples, RNA samples, DNA sequencing, RNA sequencing, data normalization, data collection, data processing, classifiers, classifier ensembles, test subjects, associated therapies, etc., described above with reference to method 400 optionally have one or more of the characteristics of the cancerous biological samples, non-cancerous biological samples, DNA samples, RNA samples, DNA sequencing, RNA sequencing, data normalization, data collection, data processing, classifiers, classifier ensembles, test subjects, associated therapies, etc., described herein with reference to other methods described herein (e.g., methods 300 and 500). For brevity, these details are not repeated here. Further details relating to various embodiments of the cancerous biological samples, non-cancerous biological samples, DNA samples, RNA samples, DNA sequencing, RNA sequencing, data normalization, data collection, data processing, classifiers, classifier ensembles, test subjects, associated therapies, etc., that are applicable in an analogous manner to method 400 are provided below.

Similarly, the details of other processes described herein with respect to other methods described herein (e.g., methods 300 and 400) are also applicable in an analogous manner to method 500 described above. For example, details relating to cancerous biological samples, non-cancerous biological samples, DNA samples, RNA samples, DNA sequencing, RNA sequencing, data normalization, data collection, data processing, classifiers, classifier ensembles, test subjects, associated therapies, etc., described above with reference to method 500 optionally have one or more of the characteristics of the cancerous biological samples, non-cancerous biological samples, DNA samples, RNA samples, DNA sequencing, RNA sequencing, data normalization, data collection, data processing, classifiers, classifier ensembles, test subjects, associated therapies, etc., described herein with reference to other methods described herein (e.g., methods 300 and 400). For brevity, these details are not repeated here. Further details relating to various embodiments of the cancerous biological samples, non-cancerous biological samples, DNA samples, RNA samples, DNA sequencing, RNA sequencing, data normalization, data collection, data processing, classifiers, classifier ensembles, test subjects, associated therapies, etc., that are applicable in an analogous manner to method 500 are provided below.

FASTQ and Alignment

When a matched normal tissue is available for a patient, a tumor-normal matched sequencing run is performed. DNA is extracted from the normal tissue, typically blood or saliva. This is then sequenced in addition to the DNA extracted from the tumor tissue. These two sequencing runs, one for the tumor tissue, and one for the normal tissue, produce two FASTQ output files. FASTQ format is a text-based format for storing both a biological sequence, such as nucleotide sequence, and its corresponding quality scores. These FASTQ files are analyzed to determine what genetic variants or copy number changes are present in the sample. A 'matched' panel-specific workflow is run to jointly analyze the tumor-normal matched FASTQ files. When a matched normal is not available, FASTQ files from the tumor tissue are analyzed in the 'tumor-only' mode.

If two or more patient samples are processed simultaneously on the same sequencer flow cell, a difference in the sequence of the adapters used for each patient sample could serve the purpose of a barcode to facilitate associating each read with the correct patient sample and placing it in the correct FASTQ file.

For efficiency, the results of paired-end sequencing of each isolate are contained in a split pair of FASTQ files. Forward (Read 1) and reverse (Read 2) sequences of each tumor and normal isolate are stored separately but in the same order and under the same identifier.

In various embodiments, the bioinformatics pipeline may filter FASTQ data from each isolate. Such filtering may include correcting or masking sequencer errors and removing (trimming) low quality sequences or bases, adapter sequences, contaminations, chimeric reads, overrepresented sequences, biases caused by library preparation, amplification, or capture, and other errors. Entire reads, individual nucleotides, or multiple nucleotides that are likely to have errors may be discarded based on the quality rating associated with the read in the FASTQ file, the known error rate of the sequencer, and/or a comparison between each nucleotide in the read and one or more nucleotides in other reads that has been aligned to the same location in the reference genome. Filtering may be done in part or in its entirety by various software tools, for example, a software tool such as Skewer (see doi.org/10.1186/1471-2105-15-182). FASTQ files may be analyzed for rapid assessment of quality control and reads, for example, by a sequencing data QC software such as AfterQC, Kraken, RNA-SeQC, FastQC, (see Illumina, BaseSpace Labs or the webpage at URL illumina.com/products/by-type/informatics-products/basespace-sequence-hub/apps/fastqc.html), or another similar software program. For paired-end reads, reads may be merged.

In a matched panel-specific tumor-normal analysis, each FASTQ file, one for tumor, and one from normal (if available) are analyzed. In the tumor-only analysis, only tumor FASTQ is available for analysis.

Each read from the FASTQ(s) may be aligned to a location in the human genome having a sequence that best matches the sequence of nucleotides in the read. There are many software programs designed to align reads, for example, Novoalign (Novocraft, Inc.), Bowtie, Burrows Wheeler Aligner (BWA), programs that use a Smith-Waterman algorithm, etc. Alignment may be directed using a reference genome (for example, hg19, GRCh38, hg38, GRCh37, other reference genomes developed by the Genome Reference Consortium, etc.) by comparing the nucleotide sequences in each read with portions of the nucleotide sequence in the reference genome to determine the portion of the reference genome sequence that is most likely to correspond to the sequence in the read. The alignment may generate a SAM file, which stores the locations of the start and end of each read according to coordinates in the reference genome and the coverage (number of reads) for each nucleotide in the reference genome. The SAM files may be converted to BAM files, BAM files may be sorted, and duplicate reads may be marked for deletion, resulting in de-duplicated BAM files. This process produces a tumor BAM file, and a normal BAM file (when available). In various embodiments, BAM files may be analyzed to detect genetic variants and other genetic features, including single nucleotide variants (SNVs), copy number variants (CNVs), gene rearrangements, etc. In various aspects, the detected genetic variants and genetic features may be analyzed as a form of quality control. For example, a pattern of detected genetic variants or features may indicate an issue related to the sample, sequencing procedure, and/or bioinformatics pipeline, for example, contamination of the sample, mislabeling of the sample, a change in reagents, a change in the sequencing procedure and/or bioinformatics pipeline, etc.

Calling SNVs and Indels

Following alignment, tools like SamBAMBA may be used for marking and filtering duplicates on the sorted bams. Software packages such as freebayes and pindel are used to call variants using the sorted BAM files as the input, together with genome and panel bed files containing the gene targets to analyze as the reference. A raw VCF file (variant call format) file is output, showing the locations where the nucleotide base in the sample is not the same as the nucleotide base in that position in the reference genome. Software packages such as vcfbreakmulti and vt are used to normalize multi-nucleotide polymorphic variants in the raw VCF file and a variant normalized VCF file is output. SNVs in the VCFs are annotated using SNPEff for transcript information, mutation effects and prevalence in 1000 genomes databases. EGFR variants are called separately through re-alignment of tumor and normal fastq files on chr 7 using speedseq. Duplicates are marked using tools such as Sambamba, and variant calling is done analogous to the steps described for other chromosomes.

Determining Copy Number Variant

In various embodiments, the systems and methods include copy number analysis methods to compute the genomic features used to estimate HRD status. For example, in some embodiments, to assess copy number, de-duplicated BAM files and a VCF generated from the variant calling pipeline may be used to compute read depth and variation in heterozygous germline SNVs between the tumor and normal samples. If a matched normal sample is not available, comparison between a tumor sample and a pool of process matched normal controls may be utilized. Circular binary segmentation may be applied and segments may be selected with highly differential log2 ratios between the tumor and its comparator (matched normal or normal pool). Approximate integer copy number may be assessed from a combination of differential coverage in segmented regions and an estimate of stromal admixture (for example, tumor purity, or the portion of a sample that is tumor vs. non-tumor) generated by analysis of heterozygous germline SNVs.

Determining Loss of Heterozygosity

In some embodiments, LOH is determined through the use of a copy number calling algorithm. First, the tumor purity and copy states in the tumor genome may be estimated using an expectation maximization algorithm (EM). Estimation of copy states and tumor purity may involve the following steps: 1) Read alignment and normalization 2) Computation of B-allele frequencies and deviations 3) Preliminary estimation of tumor purity 4) Genomic segmentation, and 5) Refinement of initial tumor purity estimate and estimation of copy states and LOH via EM algorithm. However, other methods for estimating genome-wide loss of heterozygosity that find use in generating feature data for the HRD ensemble models described herein are known in the art.

Read alignment and normalization. To compute probe target coverage, sequenced reads from a tumor tissue sample may be aligned to the human reference genome and normalized by length and depth and GC content. Reads from the normal tissue may also be processed similarly, when available. If a matched normal is not available, a normal pool, consisting of read coverages from normal healthy individuals not known to have cancer may be used. To select a gender-matched normal pool, a gender estimation step may be performed by mapping the variants to the X-chromosome together with the X-chromosome coverages. From the normal pool, the closest neighbors may be chosen, for instance through the application of a PCA selection step. Their coverage values may be used to normalize tumor coverages. This PCA selection increases the sensitivity of somatic CNV detection. Finally, the read coverage may be expressed as the ratio of tumor coverage to normal coverage and log 2 transformed.

Computation of B-allele frequencies and deviations. Heterozygous variants contain useful information about copy numbers and LOH. These variants may be mined from the somatic and germline variant calls made using freebayes and pindel. B-allele frequency (BAF) deviations from the expected normal values are calculated for each heterozygous SNP, and also represented as the BAF log-odds ratio. If a variant is normal germline, the BAF deviation from normal should be close to 0. For a variant that shows LOH, BAF deviates significantly from 0.

Preliminary estimation of tumor purity. Initial estimations for tumor purity may be obtained from somatic variants and BAF data, to be used as input for the EM algorithm. The maximum VAF of a somatic variant should in theory equal the tumor purity. This is the somatic estimate of tumor purity. From the BAF data, for a variant that shows log odds-ratio greater than 2 is clearly LOH, as such significant deviations are only expected when a copy is lost, or copy-neutral. Twice the maximum possible VAF for such a variant should in theory equal the tumor purity, and corresponds to the BAF estimate. These two estimates are averaged to form the initial estimate of tumor purity.

Genomic segmentation. A bi-variate segmentation of the genome is performed using tumor to normal coverage ratios and BAF log-odds data. A series of rolling T-tests are performed across the genome using an algorithm similar to circular binary segmentation to identify the sections of the genome where a significant switch in copy numbers is observed. This collapses the whole genome into segments, each of which has a distinct copy number profile. The segmentation branching and pruning threshold parameters control how much segmentation and focal segment detection is possible, and is optimized for Tempus data.

Refinement of initial tumor purity estimate and estimation of copy states and LOH via EM algorithm. From the initial guesses of tumor purity, a range of tumor purity values, from half the tumor purity to maximum possible value are iterated over to estimate the best fit copy states for each genomic segment. For each tumor purity estimate and genomic segment, the expected log-ratio and BAF is computed for each copy state ranging from 0 to 20, only allowing for meaningful copy state combinations. The likelihood of observed coverage and BAF is then calculated given these expectations from the bivariate probability density function and a likelihood matrix is constructed. The copy state with the maximum likelihood is returned from this matrix. This process is iterated over all segments, and a segment to best-fit copy state map is constructed. Repeating this step for all tumor purities generates a tumor-purity likelihood matrix, and the tumor purity with smallest model error and the maximum likelihood is returned as the final estimate. Once the copy state assignments are available for all genomic segments, the segments with minor copy number of 0 are assigned LOH. These segments are either a 1-copy loss, copy-neutral, or a higher order LOH, depending on the tumor purity.

Tumor Purity

To compute tumor purity, an initial tumor purity estimate was obtained from somatic variants and germline B-allele frequencies, which was then refined using a greedy algorithm that evaluates the likelihood of the tumor purity given the tumor-normal coverage log-ratio and B-allele frequency deviations from the normal expectation. The algorithm iterates through a range of tumor-purities surrounding the initial estimate to return the tumor purity with the maximum likelihood.

Loss of Heterozygosity

For estimation of genome-wide loss of heterozygosity (LOH), each SNP was evaluated for LOH based on the germline variant allele fraction and deviation of B-allele frequencies from normal expectation. A binary 0/1 system was used to assign no LOH/LOH and average proportion of genomic bases under LOH was obtained. The number of bases undergoing LOH may be divided by the total number of bases analyzed using a copy number method, such as the method described in this patent, to determine a genome-wide LOH proportion estimate. In one example, the genome-wide LOH proportion estimate may represent LOH in the somatic (cancer) sample that may not be present in the germline (normal) sample.

Classifiers

Generally, many different classification algorithms find use in the systems and methods described herein. For instance, in some embodiments, the model is a neural network algorithm, a support vector machine algorithm, a Naive Bayes algorithm, a nearest neighbor algorithm, a boosted trees algorithm, a random forest algorithm, a decision tree algorithm, a multinomial logistic regression algorithm, a linear model, or a linear regression algorithm.

In some embodiments, the classification algorithm used in the systems and methods described herein is a random forest algorithm. In some embodiments, the trained classification method comprises a trained classifier stream. In some embodiments, by way of non-limiting example the trained classifier stream is a decision tree. Decision tree algorithms suitable for use as the classification models described herein are described in, for example, Duda, 2001, Pattern Classification, John Wiley & Sons, Inc., New York, 395-396, which is hereby incorporated by reference. Tree-based methods partition the feature space into a set of rectangles, and then fit a model (like a constant) in each one. In some embodiments, the decision tree is random forest regression. One specific algorithm that can be used as the classification model is a classification and regression tree (CART). Other examples of specific decision tree algorithms that can be used as the classifier include, but are not limited to, ID3, C4.5, MART, and Random Forests. CART, ID3, and C4.5 are described in Duda, 2001, Pattern Classification, John Wiley & Sons, Inc., New York. 396-408 and 411-412, which is hereby incorporated by reference. CART, MART, and C4.5 are described in Hastie et al., 2001, The Elements of Statistical Learning, Springer-Verlag, New York, Chapter 9, which is hereby incorporated by reference in its entirety. Random Forests are described in Breiman, 1999, "Random Forests—Random Features," Technical Report 567, Statistics Department, U.C. Berkeley, September 1999, which is hereby incorporated by reference in its entirety.

In some embodiments, tumor organoids with varied BRCA LOH statuses, pathogenic mutations and genome-wide LOH measurements may be grown and treated with PARP inhibitors to obtain an in-vitro PARP drug response. Samples could span a wide range of cancer cohorts. Tumor cell lines expected to be PARP sensitive may be tested alongside negative controls that have no HRD mutations. The PARP outcome data may be used to refine input features in the random forest classifier. Additional information could be gleaned from mutational signatures and other genes in the HRD pathway. See, for example, Gulhan D C, Lee J J, Melloni GEM, Cortés-Ciriano I, Park P J, "Detecting the mutational signature of homologous recombination deficiency in clinical samples," Nat Genet., 51(5):912-19 (2019), which is incorporated by reference herein.

In an alternative embodiment, instead of or in addition to training a random forest classifier to generate HRD calls, the systems and methods use business logic. For example, in some embodiments, a business rule set, such as is illustrated in FIG. 10, is used in the systems and methods described herein.

In some embodiments, the classification algorithm used the systems and methods described herein is a regression algorithm. The regression algorithm can be any type of regression. For example, in some embodiments, the regression algorithm is logistic regression. Logistic regression algorithms are disclosed in Agresti, An Introduction to Categorical Data Analysis, 1996, Chapter 5, pp. 103-144, John Wiley & Son, New York, which is hereby incorporated by reference. In some embodiments, the regression algorithm is logistic regression with lasso, L2 or elastic net regularization.

In some embodiments, the classification algorithm used the systems and methods described herein is a neural network. Examples of neural network algorithms, including convolutional neural network algorithms, are disclosed, for example, in Vincent et al., 2010, "Stacked denoising autoencoders: Learning useful representations in a deep network with a local denoising criterion," J Mach Learn Res 11, pp. 3371-3408; Larochelle et al., 2009, "Exploring strategies for training deep neural networks," J Mach Learn Res 10, pp. 1-40; and Hassoun, 1995, Fundamentals of Artificial Neural Networks, Massachusetts Institute of Technology, each of which is hereby incorporated by reference.

In some embodiments, the classification algorithm used the systems and methods described herein is a support vector machine (SVM). Examples of SVM algorithms are described, for example, in Cristianini and Shawe-Taylor, 2000, "An Introduction to Support Vector Machines," Cambridge University Press, Cambridge; Boser et al., 1992, "A training algorithm for optimal margin classifiers," in Proceedings of the 5th Annual ACM Workshop on Computational Learning Theory, ACM Press, Pittsburgh, Pa., pp. 142-152; Vapnik, 1998, Statistical Learning Theory, Wiley, New York; Mount, 2001, Bioinformatics: sequence and genome analysis, Cold Spring Harbor Laboratory Press, Cold Spring Harbor, N.Y.; Duda, Pattern Classification, Second Edition, 2001, John Wiley & Sons, Inc., pp. 259, 262-265; and Hastie, 2001, The Elements of Statistical Learning, Springer, New York; and Furey et al., 2000, Bioinformatics 16, 906-914, each of which is hereby incorporated by reference in its entirety. When used for classification, SVMs separate a given set of binary labeled data training set with a hyper-plane that is maximally distant from the labeled data. For cases in which no linear separation is possible, SVMs can work in combination with the technique of "kernels," which automatically realizes a non-linear mapping to a feature space. The hyper-plane found by the SVM in feature space corresponds to a non-linear decision boundary in the input space.

In some embodiments, the machine-learned model includes a logistic regression classifier. In other embodiments, the machine learning or deep learning model can be one of a decision tree, an ensemble (e.g., bagging, boosting, random forest), gradient boosting machine, linear regression, Naïve Bayes, or a neural network. The HRD model includes learned weights for the features that are adjusted during training. The term "weights" is used generically here to represent the learned quantity associated with any given feature of a model, regardless of which particular machine learning technique is used. In some embodiments, a cancer indicator score is determined by inputting values for features derived from one or more DNA sequences (or DNA sequence reads thereof) into a machine learning or deep learning model.

In some embodiments, e.g., when the HRD evaluation model is a neural network (e.g., a conventional or convolutional neural network), the output of a disease classifier is a classification, e.g., either cancer positive or cancer negative. However, in some embodiments, in order to provide a continuous or semi-continuous value for the output of the model, rather than a classification, a hidden layer of a neural network, e.g., the hidden layer just prior to the output layer, is used as the output of the classification model.

Accordingly, in some embodiments, the model includes (i) an input layer for receiving values for the plurality of genotypic characteristics, where the plurality of genotypic characteristics includes a first number of dimensions, and (ii) an embedding layer that includes a set of weights, where the embedding layer directly or indirectly receives output of the input layer, and where an output of the embedding layer is a model score set having a second number of dimensions that is less than the first number of dimensions, and (iii) an output layer that directly or indirectly receives the model score set from the embedding layer. In some embodiments, the output of the classifier is an output of a set of neurons associated with a hidden layer in a neural network termed the embedding layer. In such embodiments, each such neuron in the embedding layer is associated with a weight and an activation function and the output consists of the output of each such activation function. In some embodiments, the activation function of a neuron in the embedding layer is rectified linear unit (ReLU), tanh, or sigmoid activation function. In some such embodiments, the neurons of the embedding layer are fully connected to each of the inputs of the input layer. In some such embodiments, each neuron of the output layer is fully connected to each neuron of the embedding layer. In some embodiments, each neuron of the output layer is associated with a Softmax activation function. In some embodiments, one or more of the embedding layer and the output layer is not fully connected.

Patient Report

In some embodiments, a patient report is generated based on the output of the classifier. The report may be presented to a patient, physician, medical personnel, or researcher in a digital copy (for example, a JSON object, pdf file or an image on a website or portal), a hard copy (for example, printed on paper or another tangible medium), or in another format.

In some embodiments, the report includes information related to the HRD status of the specimen, detected genetic variants, other characteristics of a patient's sample, and/or clinical records. The report may further include clinical trials for which the patient is eligible, therapies that may match the patient and/or adverse effects predicted if the patient receives a given therapy, based on the HRD status, detected genetic variants, other characteristics of the sample and/or clinical records. In one example, if a patient specimen is predicted to have HRD, the patient may be matched with PARP inhibitors, platinum-based chemotherapy, and/or additional DNA-damaging therapies.

The results included in the report and/or additional results (for example, from the bioinformatics pipeline) may be used to analyze a database of clinical data, especially to determine whether there is a trend showing that a therapy slowed cancer progression in other patients having the same or similar results as the specimen. The results may also be used to design tumor organoid experiments. For example, an organoid may be genetically engineered to have the same characteristics as the specimen and may be observed after exposure to a therapy to determine whether the therapy can reduce the growth rate of the organoid, and thus is likely to reduce the growth rate of the patient associated with the specimen.

In this example, HRD information may be stored in a report object, such as a JSON object, for further processing and/or display. For example, information from the report object may be used to prepare a clinical laboratory report for return to an ordering physician. The information may be provided as a combination of text, images, and/or audio. An example display of text and images that indicate HRD information is presented as FIG. 11.

In some embodiments, the report also includes a listing of genetic variants related to the genes in the homologous recombination DNA repair pathway and/or genes that interact with this pathway. An example display for this listing is presented as FIG. 12.

Therapy

In some aspects, the systems and methods disclosed herein may be used as a companion diagnostic. For example, in some embodiments, an estimated HRD status may be used by a clinician to make a decision to treat a cancer with a PARP inhibitor.

Table 2 lists several PARP inhibitors and the FDA approval or clinical trial status of each PARP inhibitor for various cancer types in 2019. This table illustrates the widespread potential utility of PARP inhibitors for patients who have tested positive for HRD.

TABLE 2

Example PARP inhibitors

| Drug | Cancer Types | FDA Approval |
|---|---|---|
| Olaparib | Ovarian, Breast | Approved |
| | Gastric, Gastroesophageal Junction, Prostate, Lung (SC/NSC), Pancreatic Fallopian, Primary Peritoneal, Urothelial (Bladder), Pediatric Solid Tumors & Non-Hodgkin's | Trial |
| Rucaparib | Ovarian | Approved |
| | Fallopian, Primary Peritoneal, Any BRCA1/2 Solid, Urothelial, Prostate, Endometrial | Trial |
| Niraparib | Ovarian, Fallopian, Primary Peritoneal | Approved |
| | Pancreatic, Prostate, Solid | Trial |
| Talazoparib | Breast | Approved |
| | Advanced or Recurrent Solid Tumors, Breast Neoplasms, Epithelial Ovarian Cancer, Ewing Sarcoma, Small Cell Lung Carcinoma, Prostate Cancer, Pancreas Cancer | Trial |

In some aspects, an estimated HRD status may be used by a clinician to make a decision to treat a cancer with the addition of platinum to standard neoadjuvant chemotherapy. Adding a platinum agent to standard combination chemotherapy increases the toxicity of treatment, and so patients will benefit from an estimated HRD that indicates whether their cancer is more likely to be treated through the combination of a platinum agent and standard combination chemotherapy.

In some aspects, PARP inhibitors have been approved for treatment of cancers harboring specifically germline alterations. For example, olaparib is approved for germline BRCA (gBRCA) positive ovarian cancer treated with at least 3 prior chemo regimens and talazaparib is approved for gBRCA positive, HER2 negative localized or metastatic breast cancer. Detecting germline variants in BRCA or other genes related to DNA repair pathways may aid a physician in deciding to prescribe PARPi.

Implementation Using a Digital and Laboratory Health Care Platform

The methods and systems described herein may be utilized in combination with or as part of a digital and laboratory health care platform that is generally targeted to medical care and research. It should be understood that many uses of the methods and systems described above, in combination with such a platform, are possible. One example of such a platform is described in U.S. patent application Ser. No. 16/657,804, titled "Data Based Cancer Research and Treatment Systems and Methods", and filed Oct. 18, 2019, which is incorporated herein by reference and in its entirety for all purposes.

For example, an implementation of one or more embodiments of the methods and systems as described above may include microservices constituting a digital and laboratory health care platform supporting HRD status determination. Embodiments may include a single microservice for executing and delivering HRD status determination or may include a plurality of microservices each having a particular role which together implement one or more of the embodiments above. In one example, a first microservice may execute computation of genomic features in order to deliver features to a second microservice for training an HRD model. Similarly, the second microservice may execute training an HRD model to deliver a trained HRD model to a third microservice according to an embodiment, above. A third microservice may use a trained HRD model to analyze data associated with a specimen to determine the likelihood of the specimen having HRD.

Where embodiments above are executed in one or more micro-services with or as part of a digital and laboratory health care platform, one or more of such micro-services may be part of an order management system that orchestrates the sequence of events as needed at the appropriate time and in the appropriate order necessary to instantiate embodiments above. A micro-services based order management system is disclosed, for example, in U.S. Prov. Patent Application No. 62/873,693, titled "Adaptive Order Fulfillment and Tracking Methods and Systems", filed Jul. 12, 2019, which is incorporated herein by reference and in its entirety for all purposes.

For example, continuing with the above first and second microservices, an order management system may notify the first microservice that an order for HRD status determination has been received and is ready for processing. The first microservice may execute and notify the order management system once the delivery of HRD status determination is ready for the second microservice. Furthermore, the order management system may identify that execution parameters (prerequisites) for the second microservice are satisfied, including that the first microservice has completed, and notify the second microservice that it may continue processing the order to determine HRD status according to an embodiment, above.

Where the digital and laboratory health care platform further includes a genetic analyzer system, the genetic analyzer system may include targeted panels and/or sequencing probes. An example of a targeted panel is disclosed, for example, in U.S. Prov. Patent Application No. 62/902,950, titled "System and Method for Expanding Clinical Options for Cancer Patients using Integrated Genomic Profiling", and filed Sep. 19, 2019, which is incorporated herein by reference and in its entirety for all purposes. In one example, targeted panels may enable the delivery of next generation sequencing results for HRD status determination according to an embodiment, above. An example of the design of next-generation sequencing probes is disclosed, for example, in U.S. Prov. Patent Application No. 62/924,073, titled "Systems and Methods for Next Generation Sequencing Uniform Probe Design", and filed Oct. 21, 2019, which is incorporated herein by reference and in its entirety for all purposes.

Where the digital and laboratory health care platform further includes a bioinformatics pipeline, the methods and systems described above may be utilized after completion or substantial completion of the systems and methods utilized in the bioinformatics pipeline. As one example, the bioinformatics pipeline may receive next-generation genetic sequencing results and return a set of binary files, such as one or more BAM files, reflecting DNA and/or RNA read counts aligned to a reference genome. The methods and systems described above may be utilized, for example, to ingest the DNA and/or RNA read counts and produce a determination of HRD status as a result.

When the digital and laboratory health care platform further includes an RNA data normalizer, any RNA read counts may be normalized before processing embodiments as described above. An example of an RNA data normalizer is disclosed, for example, in U.S. patent application Ser. No. 16/581,706, titled "Methods of Normalizing and Correcting RNA Expression Data", and filed Sep. 24, 2019, which is incorporated herein by reference and in its entirety for all purposes.

When the digital and laboratory health care platform further includes a genetic data deconvoluter, any system and method for deconvoluting may be utilized for analyzing genetic data associated with a specimen having two or more biological components to determine the contribution of each component to the genetic data and/or determine what genetic data would be associated with any component of the specimen if it were purified. An example of a genetic data deconvoluter is disclosed, for example, in U.S. patent application Ser. No. 16/732,229 and PCT19/69161, both titled "Transcriptome Deconvolution of Metastatic Tissue Samples", and filed Dec. 31, 2019, U.S. Prov. Patent Application No. 62/924,054, titled "Calculating Cell-type RNA Profiles for Diagnosis and Treatment", and filed Oct. 21, 2019, and U.S. Prov. Patent Application No. 62/944,995, titled "Rapid Deconvolution of Bulk RNA Transcriptomes for Large Data Sets (Including Transcriptomes of Specimens Having Two or More Tissue Types)", and filed Dec. 6, 2019 which are incorporated herein by reference and in their entirety for all purposes.

When the digital and laboratory health care platform further includes an automated RNA expression caller, RNA expression levels may be adjusted to be expressed as a value relative to a reference expression level, which is often done in order to prepare multiple RNA expression data sets for analysis to avoid artifacts caused when the data sets have differences because they have not been generated by using the same methods, equipment, and/or reagents. An example of an automated RNA expression caller is disclosed, for example, in U.S. Prov. Patent Application No. 62/943,712, titled "Systems and Methods for Automating RNA Expression Calls in a Cancer Prediction Pipeline", and filed Dec. 4, 2019, which is incorporated herein by reference and in its entirety for all purposes.

The digital and laboratory health care platform may further include one or more insight engines to deliver information, characteristics, or determinations related to a disease state that may be based on genetic and/or clinical data associated with a patient and/or specimen. Exemplary insight engines may include a tumor of unknown origin engine, a human leukocyte antigen (HLA) loss of homozygosity (LOH) engine, a tumor mutational burden engine, a PD-L1 status engine, a homologous recombination deficiency engine, a cellular pathway activation report engine, an immune infiltration engine, a microsatellite instability engine, a pathogen infection status engine, and so forth. An example tumor of unknown origin engine is disclosed, for example, in U.S. Prov. Patent Application No. 62/855,750, titled "Systems and Methods for Multi-Label Cancer Classification", and filed May 31, 2019, which is incorporated herein by reference and in its entirety for all purposes. An example of an HLA LOH engine is disclosed, for example, in U.S. Prov. Patent Application No. 62/889,510, titled "Detection of Human Leukocyte Antigen Loss of Heterozygosity", and filed Aug. 20, 2019, which is incorporated herein by reference and in its entirety for all purposes. An example of a tumor mutational burden (TMB) engine is disclosed, for example, in U.S. Prov. Patent Application No. 62/804,458, titled "Assessment of Tumor Burden Methodologies for Targeted Panel Sequencing", and filed Feb. 12, 2019, which is incorporated herein by reference and in its entirety for all purposes. An example of a PD-L1 status engine is disclosed, for example, in U.S. Prov. Patent Application No. 62/854,400, titled "A Pan-Cancer Model to Predict The PD-L1 Status of a Cancer Cell Sample Using RNA Expression Data and Other Patient Data", and filed May 30, 2019, which is incorporated herein by reference and in its entirety for all purposes. An additional example of a PD-L1 status engine is disclosed, for example, in U.S. Prov. Patent Application No. 62/824,039, titled "PD-L1 Prediction Using H&E Slide Images", and filed Mar. 26, 2019, which is incorporated herein by reference and in its entirety for all purposes. The systems and methods disclosed herein are an example of a homologous recombination deficiency engine. An alternative homologous recombination deficiency engine is disclosed, for example, in U.S. Prov. Patent Application No. 62/804,730, titled "An Integrative Machine-Learning Framework to Predict Homologous Recombination Deficiency", and filed Feb. 12, 2019, which is incorporated herein by reference and in its entirety for all purposes. An example of a cellular pathway activation report engine is disclosed, for example, in U.S. Prov. Patent Application No. 62/888,163, titled "Cellular Pathway Report", and filed Aug. 16, 2019, which is incorporated herein by reference and in its entirety for all purposes. An example of an immune infiltration engine is disclosed, for example, in U.S. patent application Ser. No. 16/533,676, titled "A Multi-Modal Approach to Predicting Immune Infiltration Based on Integrated RNA Expression and Imaging Features", and filed Aug. 6, 2019, which is incorporated herein by reference and in its entirety for all purposes. An additional example of an immune infiltration engine is disclosed, for example, in U.S. Patent Application No. 62/804,509, titled "Comprehensive Evaluation of RNA Immune System for the Identification of Patients with an Immunologically Active Tumor Microenvironment", and filed Feb. 12, 2019, which is incorporated herein by reference and in its entirety for all purposes. An example of an MSI engine is disclosed, for example, in U.S. patent application Ser. No. 16/653,868, titled "Microsatellite Instability Determination System and Related Methods", and filed Oct. 15, 2019, which is incorporated herein by reference and in its entirety for all purposes. An additional example of an MSI engine is disclosed, for example, in U.S. Prov. Patent Application No. 62/931,600, titled "Systems and Methods for Detecting Microsatellite Instability of a Cancer Using a Liquid Biopsy", and filed Nov. 6, 2019, which is incorporated herein by reference and in its entirety for all purposes.

When the digital and laboratory health care platform further includes a report generation engine, the methods and systems described above may be utilized to create a summary report of a patient's genetic profile and the results of one or more insight engines for presentation to a physician. For instance, the report may provide to the physician information about the extent to which the specimen that was sequenced contained tumor or normal tissue from a first organ, a second organ, a third organ, and so forth. For example, the report may provide a genetic profile for each of the tissue types, tumors, or organs in the specimen. The genetic profile may represent genetic sequences present in the tissue type, tumor, or organ and may include variants, expression levels, information about gene products, or other information that could be derived from genetic analysis of a tissue, tumor, or organ. The report may include therapies and/or clinical trials matched based on a portion or all of the genetic profile or insight engine findings and summaries. For example, the therapies may be matched according to the systems and methods disclosed in U.S. Prov. Patent Application No. 62/804,724, titled "Therapeutic Suggestion Improvements Gained Through Genomic Biomarker Matching Plus Clinical History", filed Feb. 12, 2019, which is incorporated herein by reference and in its entirety for all purposes. For example, the clinical trials may be matched according to the systems and methods disclosed in U.S. Prov. Patent Application No. 62/855,913, titled "Systems and Methods of Clinical Trial Evaluation", filed May 31, 2019, which is incorporated herein by reference and in its entirety for all purposes.

The report may include a comparison of the results to a database of results from many specimens. An example of methods and systems for comparing results to a database of results are disclosed in U.S. Prov. Patent Application No. 62/786,739, titled "A Method and Process for Predicting and Analyzing Patient Cohort Response, Progression and Survival", and filed Dec. 31, 2018, which is incorporated herein by reference and in its entirety for all purposes. The information may be used, sometimes in conjunction with similar information from additional specimens and/or clinical response information, to discover biomarkers or design a clinical trial.

When the digital and laboratory health care platform further includes application of one or more of the embodiments herein to organoids developed in connection with the platform, the methods and systems may be used to further evaluate genetic sequencing data derived from an organoid to provide information about the extent to which the organoid that was sequenced contained a first cell type, a second cell type, a third cell type, and so forth. For example, the report may provide a genetic profile for each of the cell types in the specimen. The genetic profile may represent genetic sequences present in a given cell type and may include variants, expression levels, information about gene products, or other information that could be derived from genetic analysis of a cell. The report may include therapies matched based on a portion or all of the deconvoluted information. These therapies may be tested on the organoid, derivatives of that organoid, and/or similar organoids to determine an organoid's sensitivity to those therapies. For example, organoids may be cultured and tested according to the systems and methods disclosed in U.S. patent application Ser. No. 16/693,117, titled "Tumor Organoid Culture Compositions, Systems, and Methods", filed Nov. 22, 2019; U.S. Prov. Patent Application No. 62/924,621, titled "Systems and Methods for Predicting Therapeutic Sensitivity", filed Oct. 22, 2019; and U.S. Prov. Patent Application No. 62/944,292, titled "Large Scale Phenotypic Organoid Analysis", filed Dec. 5, 2019, which are incorporated herein by reference and in their entirety for all purposes.

When the digital and laboratory health care platform further includes application of one or more of the above in combination with or as part of a medical device or a laboratory developed test that is generally targeted to medical care and research, such laboratory developed test or medical device results may be enhanced and personalized through the use of artificial intelligence. An example of laboratory developed tests, especially those that may be enhanced by artificial intelligence, is disclosed, for example, in U.S. Provisional Patent Application No. 62/924,515, titled "Artificial Intelligence Assisted Precision Medicine Enhancements to Standardized Laboratory Diagnostic Testing", and filed Oct. 22, 2019, which is incorporated herein by reference and in its entirety for all purposes.

It should be understood that the examples given above are illustrative and do not limit the uses of the systems and methods described herein in combination with a digital and laboratory health care platform.

EXAMPLES

Example 1—Training of an Ensemble HRD Prediction Model

A stacked, linear-regression model ensemble model of HRD status was trained against the outputs of (i) an elastic net model trained to predict whether a cancer is homologous recombination deficiency (HRD) positive based on gene expression levels generated from RNAseq data generated from solid tumor samples, (ii) an elastic net model trained to predict a probability that a cancer is homologous recombination deficiency (HRD) positive based on ssGSEA enrichment scores, (iii) a logistic RIDGE regression model trained to predict a binarized promoter methylation status based on specimen RNA datasets, and (iv) a model trained to predict an HRD status based on the percent of sequenced nucleotide bases that had detectable loss of heterozygosity (LOH) in DNA sequencing data from a cancerous tissue. The ensemble method was trained against data from the TCGA database, labeling biallelic BRCA1/2 variant samples as HRD positive, wild type BRCA1/2 samples (containing no BRCA1 or BRCA2 mutations or deletions) as HRD negative, and excluding samples having a single BRCA1 or BRCA2 mutation. A separate model was trained, using the same dataset and HRD labeling convention, to predict whether a cancer is homologous recombination deficiency (HRD) positive based on an estimate of genome-wide loss of heterozygosity.

Figure 7:
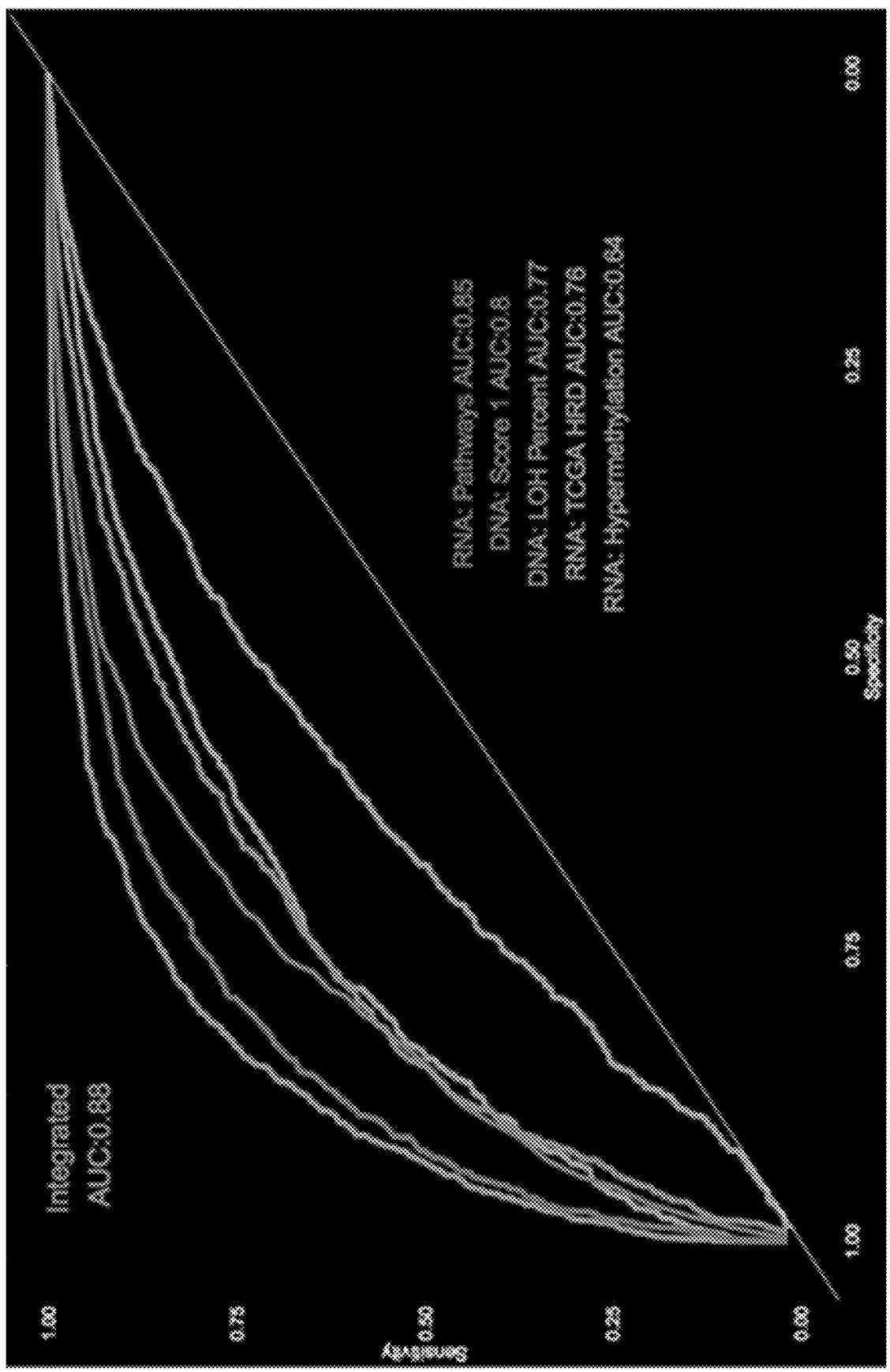
FIG. 7 illustrates ROC curves for the performance of four individual HRD models, an ensemble HRD model, and a DNA sequencing-based HRD model, as described in Example 1, and in accordance with some embodiments of the present disclosure.

FIG. 7 illustrates ROC curves for the performance of each individual model, as well as the ensemble model, on a validation cohort left out of the training cohort. In addition, the performance of a DNA sequencing-based HRD model, as described in Knijnenburg et al., Cell Reports, 23(1):239-54 (2018), the content of which is incorporated herein by reference, was assessed against the validation cohort.

The ensemble model increased the ability to detect HRD by integrating the three independent RNA-based models and a DNA-based score in a stacked model. This integrated DNA/RNA model (e.g., as described above and further with reference to block 370 of FIG. 3) outperforms each individual model, as well as the DNA-based model described in Knijnenburg et al. (Supra).

Example 2—Evaluation of an Gene Expression-Based Model of HRD Status

Various elastic models were trained to predict whether a cancer is homologous recombination deficiency (HRD) positive against gene expression levels generated from RNAseq data from single cancer types: BRCA, UCEC, BLCA, STAD, and SARC mean: Breast Cancer, Uterine Corpus Endometrial Carcinoma, Bladder Cancer, Stomach Adenocarcinoma, and Sarcoma, respectively. FIG. 8 shows the top five performance metrics for each of these elastic net models.

Figure 9A:
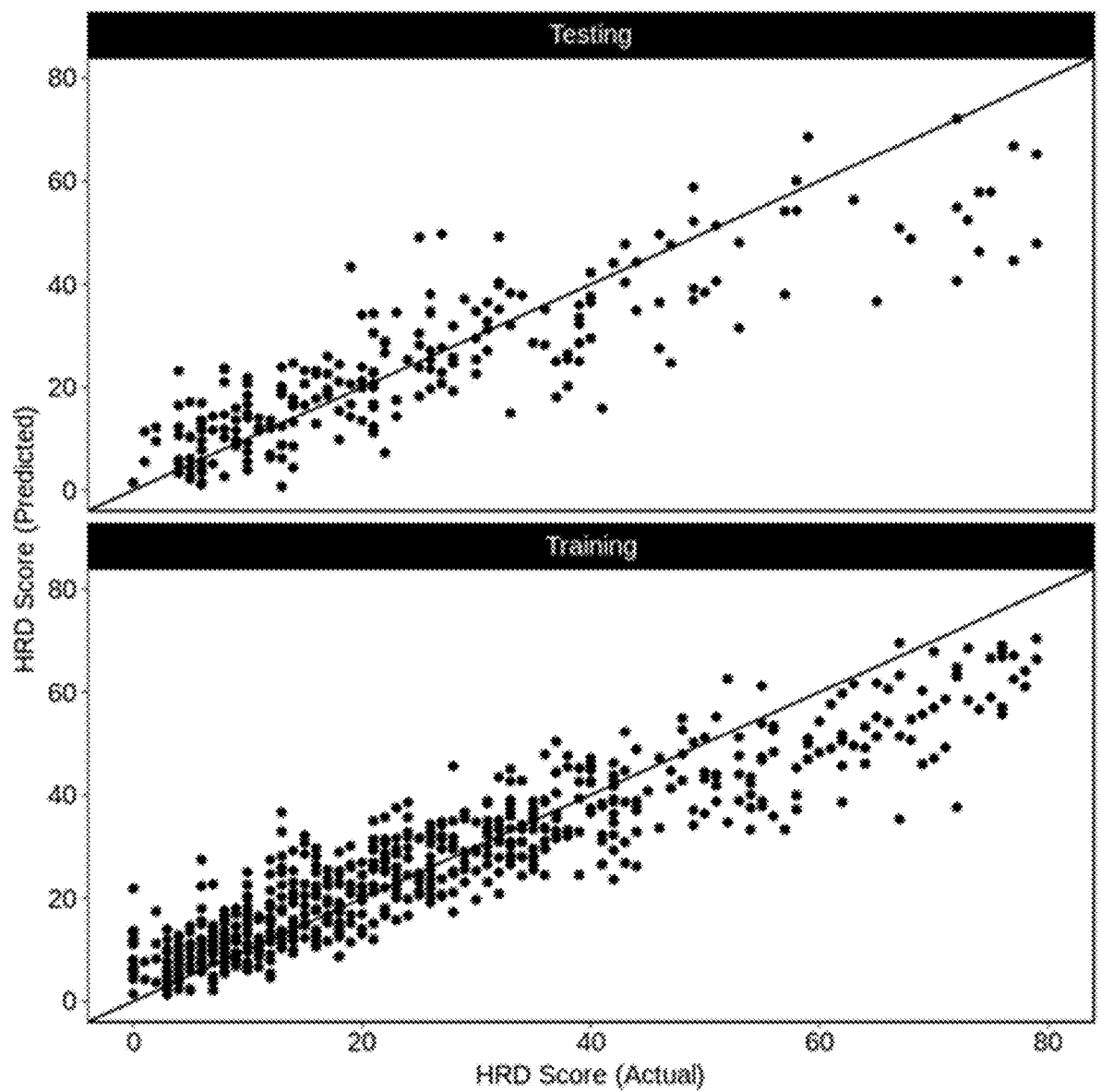
FIG. 9A illustrates a correlation between HRD scores generated using an example elastic net model trained to predict whether a cancer is homologous recombination deficiency (HRD) positive based on gene expression levels generated from RNAseq data generated from solid tumor samples and a DNA-based HRD score, in accordance with some embodiments of the present disclosure.

Example 3—Correlation Between a Gene Expression-Based Model of HRD Status and a Previously-Validated DNA-Based HRD Model FIG. 9A illustrates the correlation between HRD scores generated using an example elastic net model trained to predict whether a cancer is homologous recombination deficiency (HRD) positive based on gene expression levels generated from RNAseq data generated from solid tumor samples and the DNA-based HRD score described in Knijnenburg et al. (Supra). The x-axis shows the DNA-based HRD score for a specimen and the y-axis shows the HRD score generated for gene expression HRD model. The top panel shows results for testing data and the bottom panel shows results for training data.

Figure 9B:
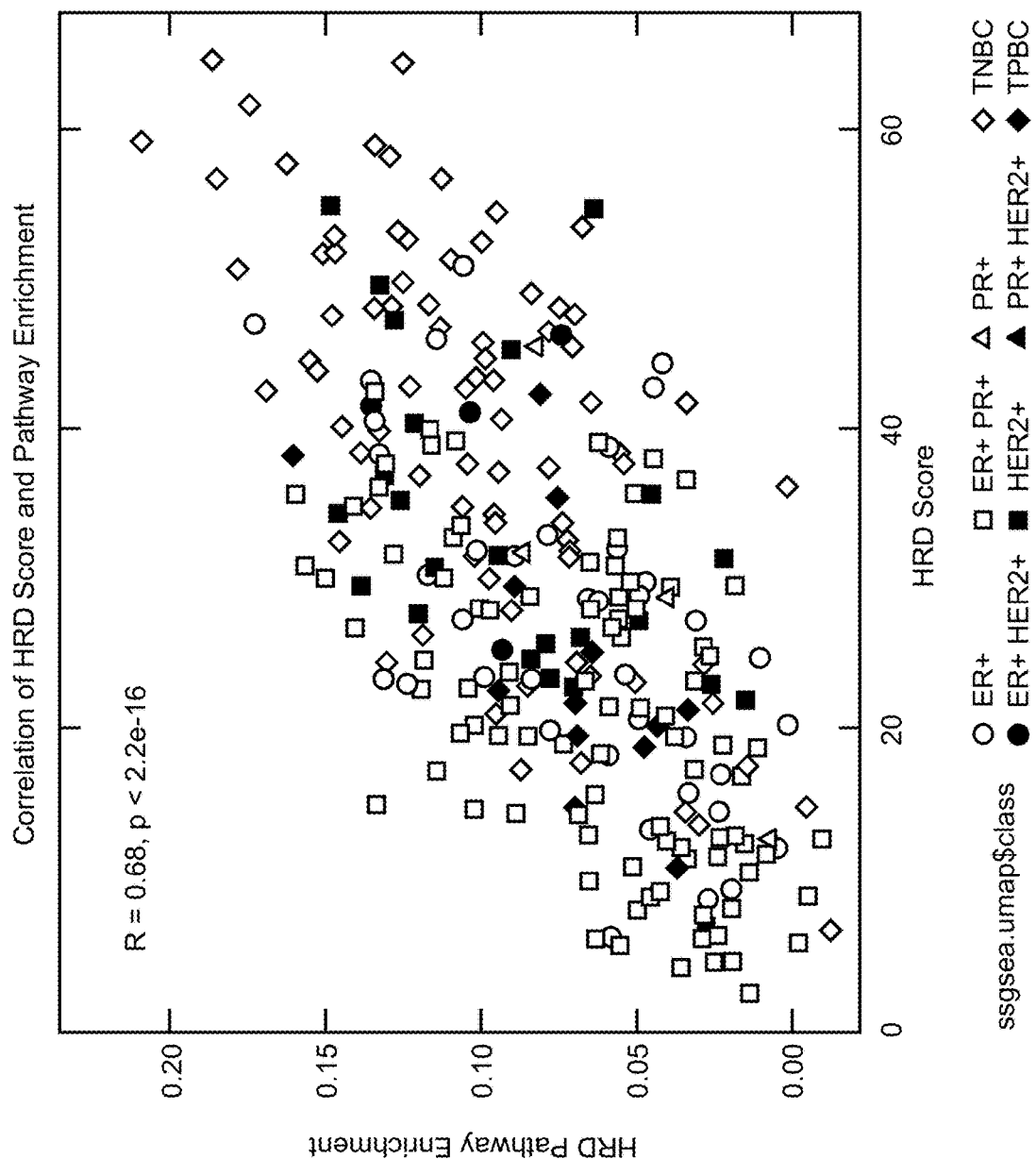
FIG. 9B illustrates a correlation between HRD scores generated using an example elastic net model trained to predict whether a cancer is homologous recombination deficiency (HRD) positive based on gene expression levels generated from RNAseq data generated from solid tumor samples (x-axis) and homologous recombination ssGSEA pathway scores, in accordance with some embodiments of the present disclosure.

Example 4—Correlation Between a Gene Expression-Based Model of HRD Status and ssGSEA Pathway Scores FIG. 9B illustrates the correlation between HRD scores generated using an example elastic net model trained to predict whether a cancer is homologous recombination deficiency (HRD) positive based on gene expression levels generated from RNAseq data generated from solid tumor samples (x-axis) and homologous recombination ssGSEA pathway scores for various classes of cancer, as indicated in the legend (y-axis).

Figure 9C:
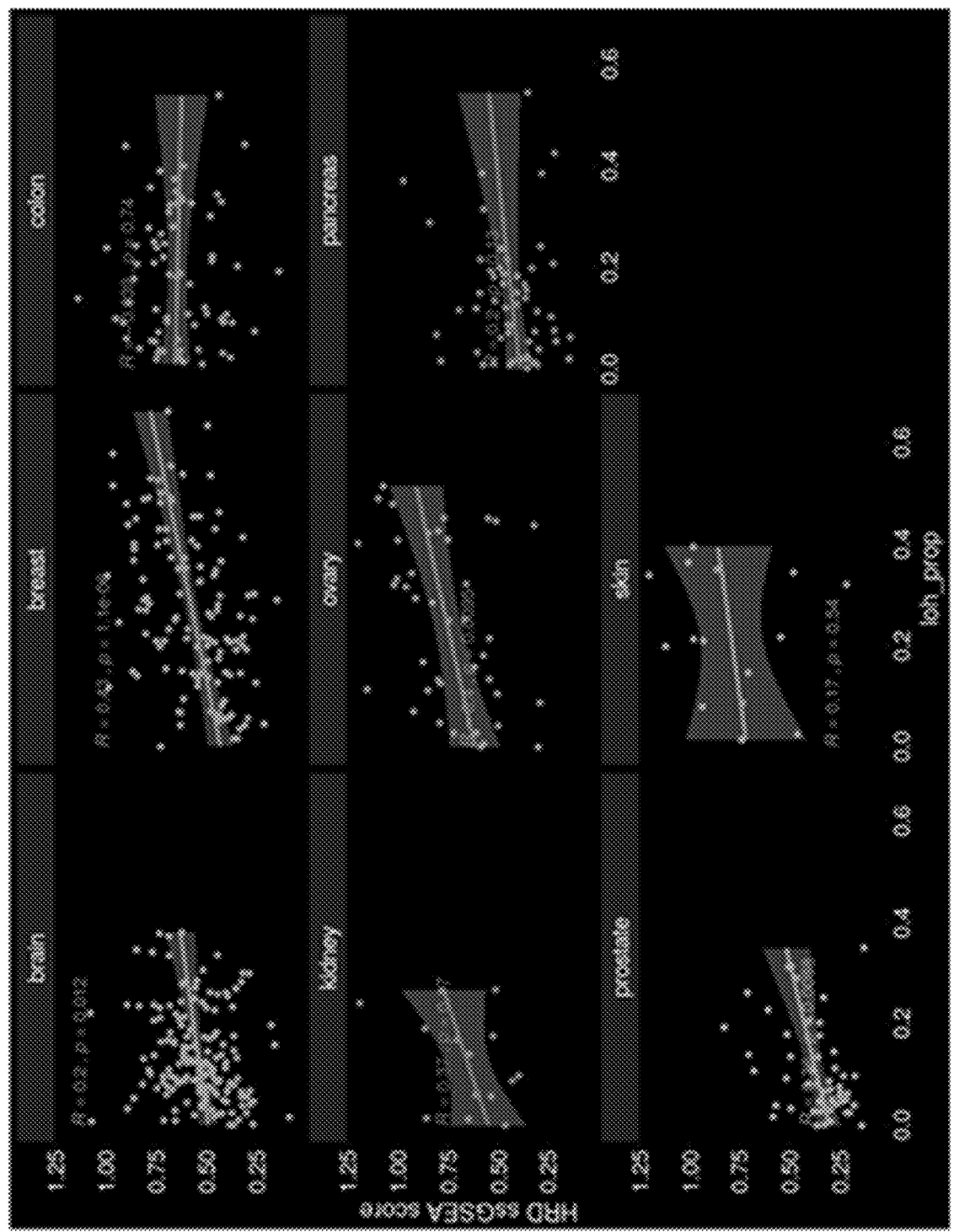
FIG. 9C illustrates correlations between homologous recombination ssGSEA pathway scores and a DNA-based loss of heterozygosity (LOH) model for HRD for various cancer types, in accordance with some embodiments of the present disclosure.

Example 5—Correlations Between ssGSEA Pathway Scores and a Previously-Validated DNA-Based HRD Model FIG. 9C illustrates correlations between homologous recombination ssGSEA pathway scores and the model trained to predict an HRD status based on the percent of sequenced nucleotide bases that had detectable loss of heterozygosity (LOH) in DNA sequencing data, for various cancer types as labeled. The x-axis shows the LOH model score for a specimen and the y-axis shows the homologous recombination ssGSEA pathway score.

Example 6—Training an Ensemble Method for Determining a Homologous Recombination Pathway Status of a Cancer One obstacle to training a model for determining HRD status is the relative unavailability of ground truth target labels for the training data. Specifically, determining which specimens in a training dataset actually have HRD and would respond, e.g., to PARPi therapy and/or platinum-containing neoadjuvant chemotherapy, and which do not.

One training data label that would facilitate this is a PARPi sensitivity label, but there are currently not enough PARPi response/outcomes available for patients or tumor organoids yet. Instead, BRCA deficiency (bi-allelic loss of either BRCA1 or BRCA2) and/or genome wide loss of heterozygosity (gwLOH) was used as a substitute, in order to label each specimen in training data as HRD positive or HRD negative. Cancer labels for each of the samples were also used in the training of the ensemble model, as some variability in transcriptional profiles and loss of heterozygosity is attributable to the type of cancer, rather than the HRD status of the cancer.

As an example, models trained in this fashion can be stacked models using outputs from one or more of the following modules: a transcriptome (RNA expression level) model, a genome-wide and/or promoter-level (e.g., BRCA promoter) methylation model, a genome-wide Loss of heterozygosity (gwLOH) model, a gene rearrangement (e.g., including one or more of gene fusions, intergenic insertions, intergenic deletions, and inversions) model, and a ssGSEA enrichment scores/pathway model.

Individual models of HRD status were trained for each of these biological features. Two RNA expression models were trained, using training sets from different sources. Samples were only used for training if they were completely wild-type for BRCA1 and BRCA2 (no single nucleotide variants, no short insertions or deletions, and diploid copy number), which are treated as negative, and samples with biallelic inactivation (BRCA-deficient, at least two pathogenic mutations or copy-loss events in either BRCA1 or BRCA2) are treated as positive.

Figure 11B:
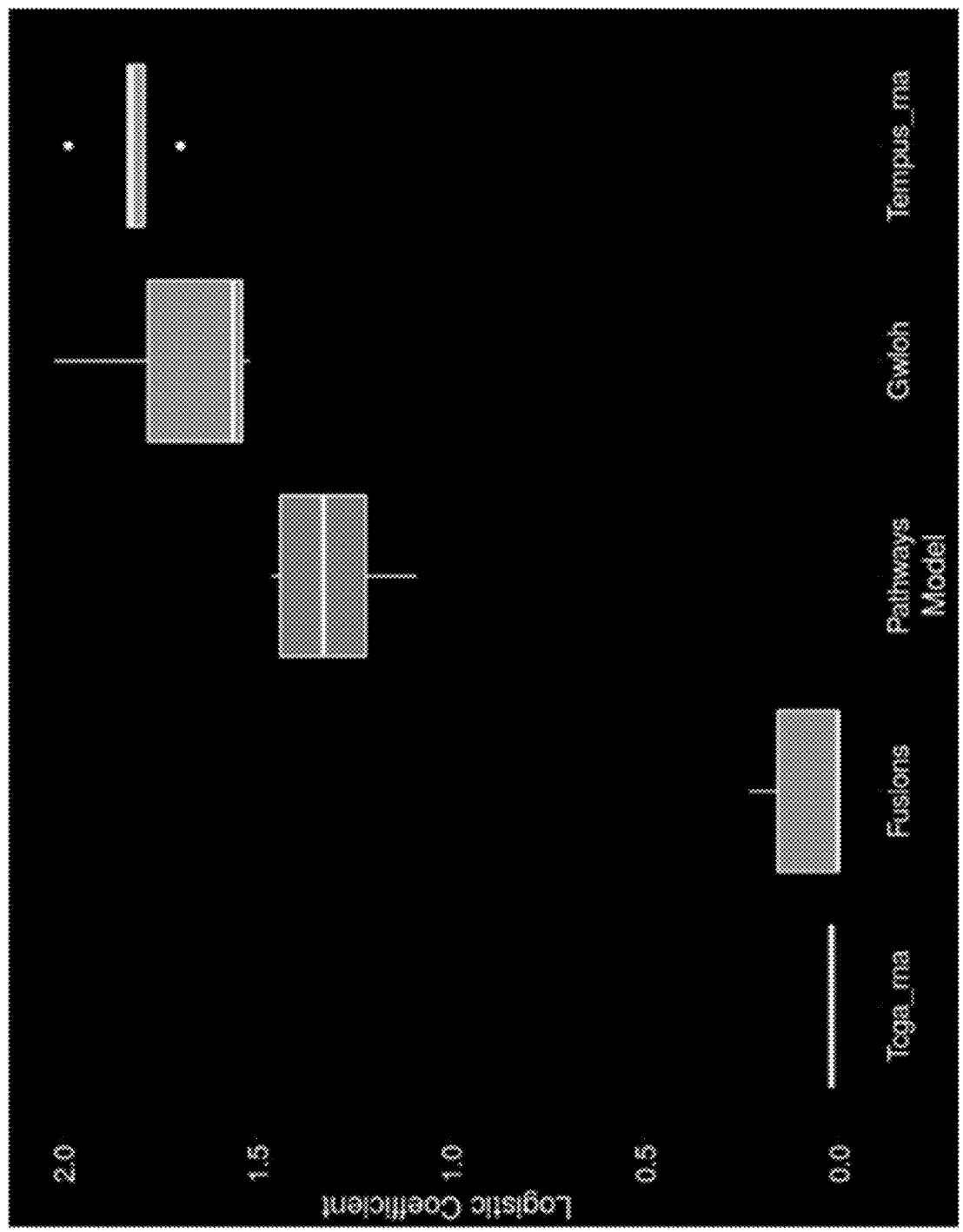

FIGS. 11A and 11B illustrates metrics for the best-performing individual models of each data type, trained as described in Example 6, where ground truth HRD status is defined using bi-allelic inactivation (BRCA-deficient, at least two pathogenic mutations or copy-loss events in either BRCA1 or BRCA2) as a proxy for HRD+ status.

Figure 12A:
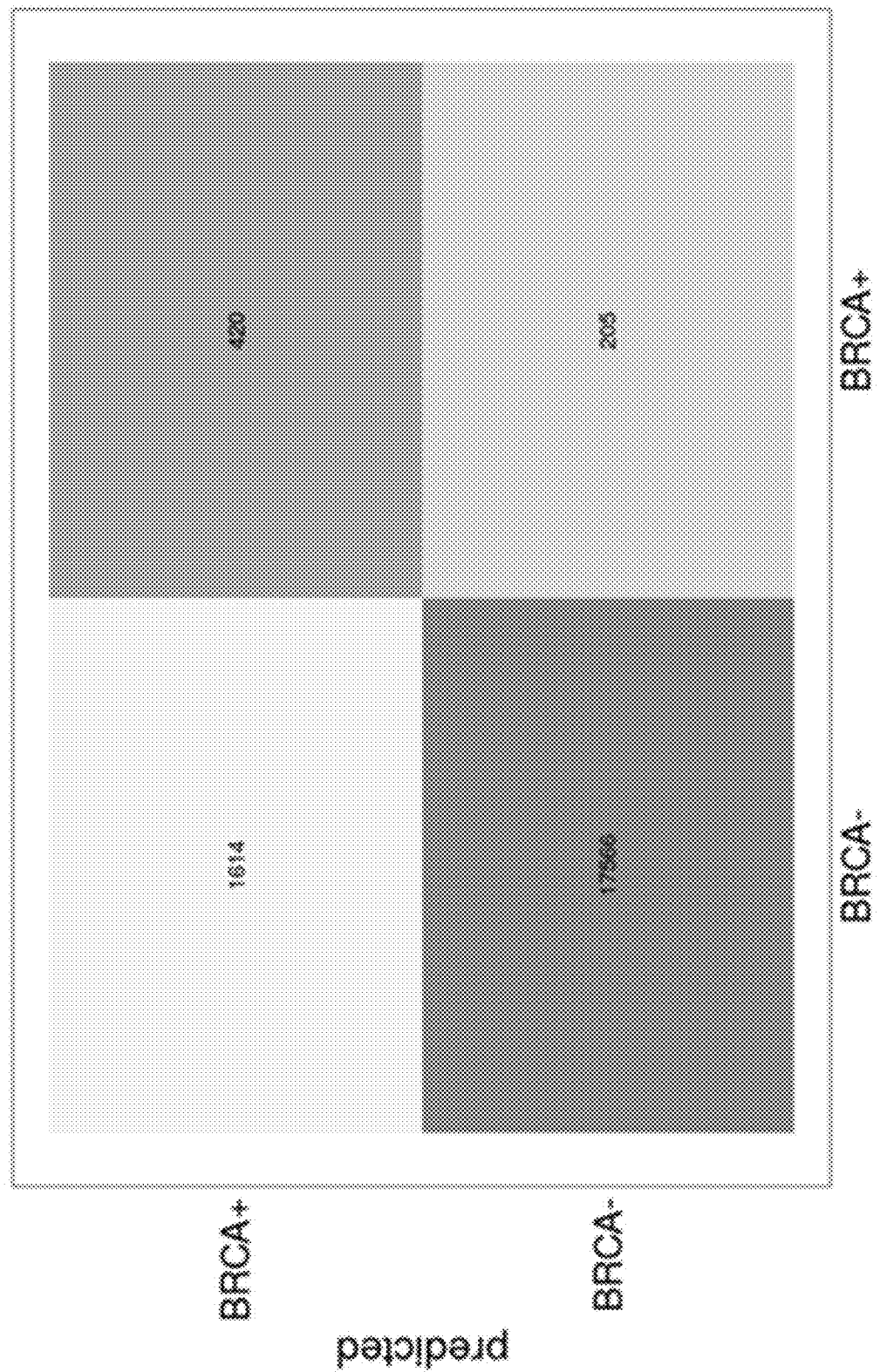
Figure 12B:
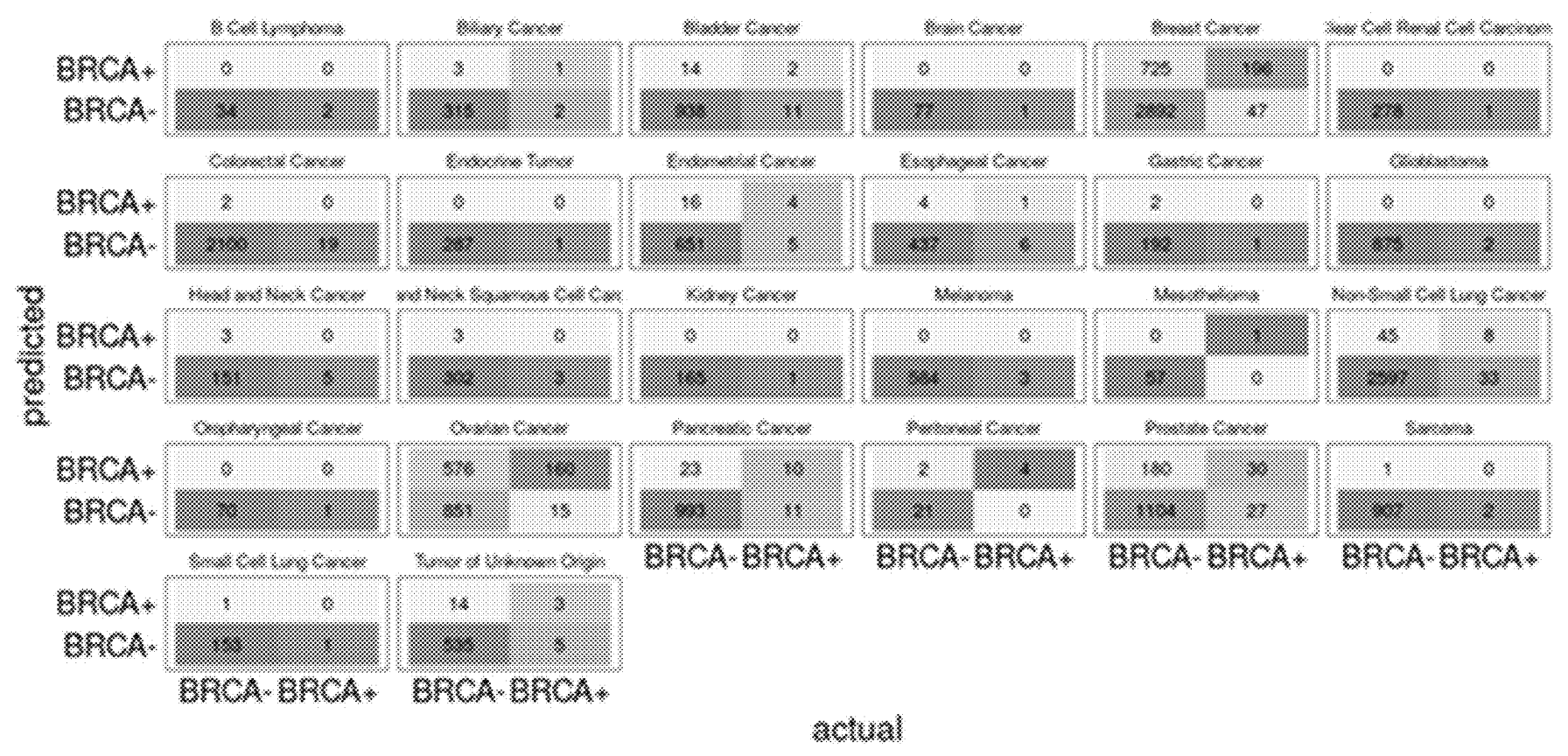

FIGS. 12A and 12B illustrate confusion matrices for the performance of a stacked model where ground truth HRD status is defined using bi-allelic inactivation (BRCA-deficient, at least two pathogenic mutations or copy-loss events in either BRCA1 or BRCA2) as a proxy for HRD+ status (FIG. 12A) and confusion matrices for the performance of the stacked model on single cancer-type cohorts, again using bi-allelic inactivation as a proxy for HRD+ status (FIG. 12B).

Figure 13A:
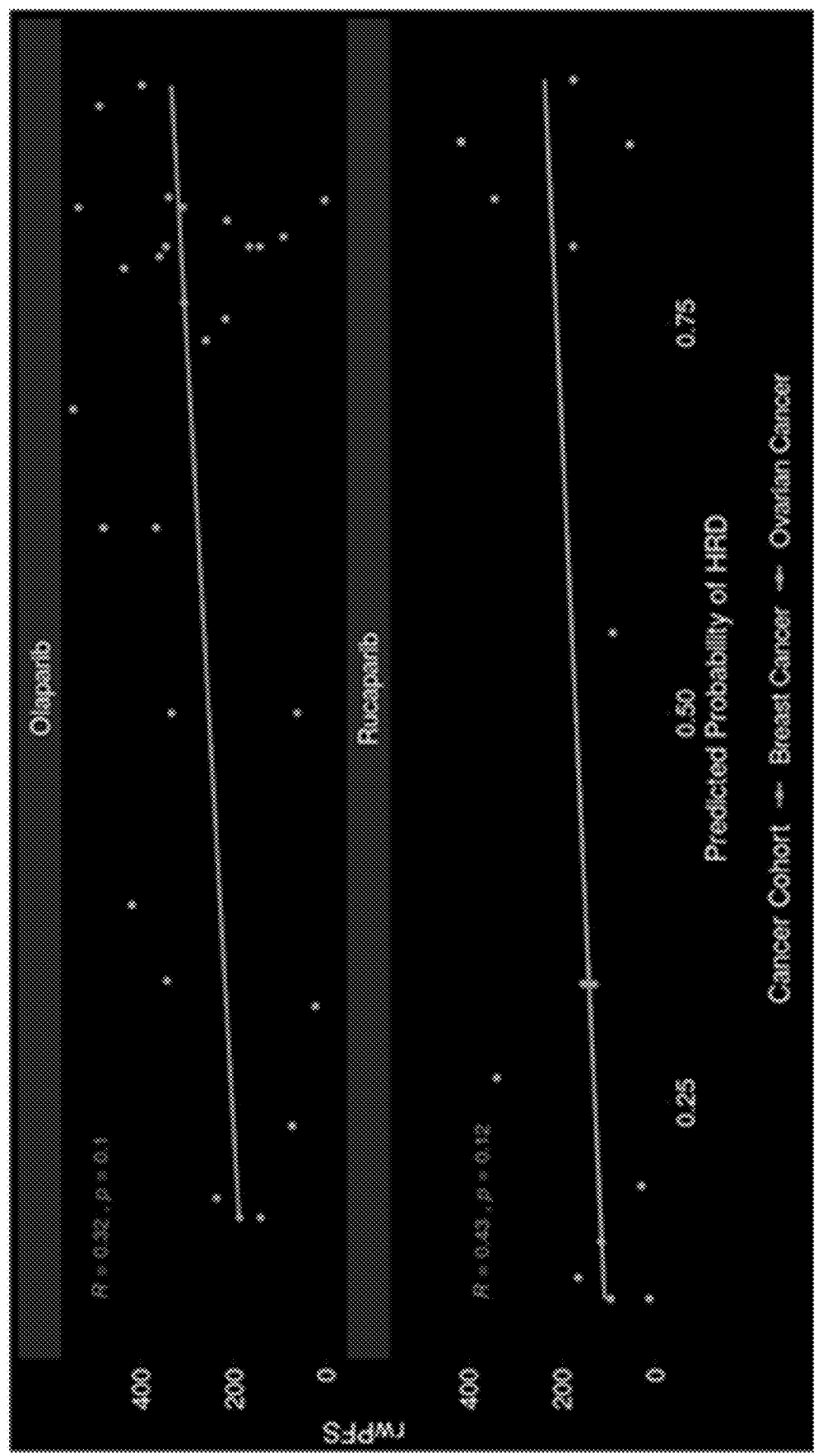
FIGS. 13A and 13B illustrate correlations between HRD status predicted by the stacked model and PARPi treatment outcomes, for a limited dataset where RNA sequencing data, DNA sequencing data, and PARPi treatment outcomes is available. HRD negative predictions are shown in the top panel of FIG. 13A and the left plot of each pair in FIG. 13B.
Figure 13B:
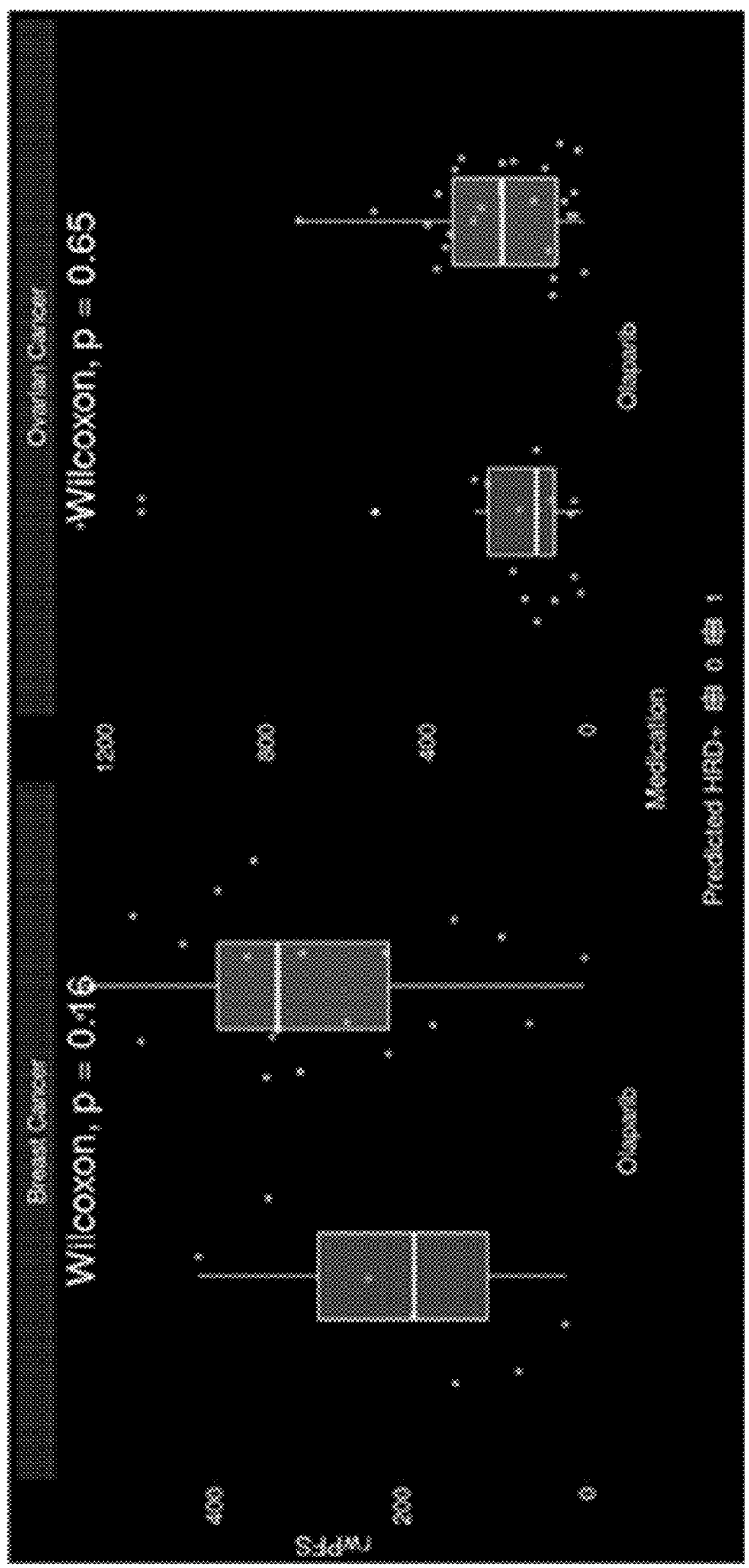

FIGS. 13A and 13B illustrate correlations between HRD status predicted by the stacked model and PARPi treatment outcomes, for a limited dataset where RNA sequencing data, DNA sequencing data, and PARPi treatment outcomes is available. HRD negative predictions are shown in the top panel of FIG. 13A and the left plot of each pair in FIG. 13B.

Figure 10A:
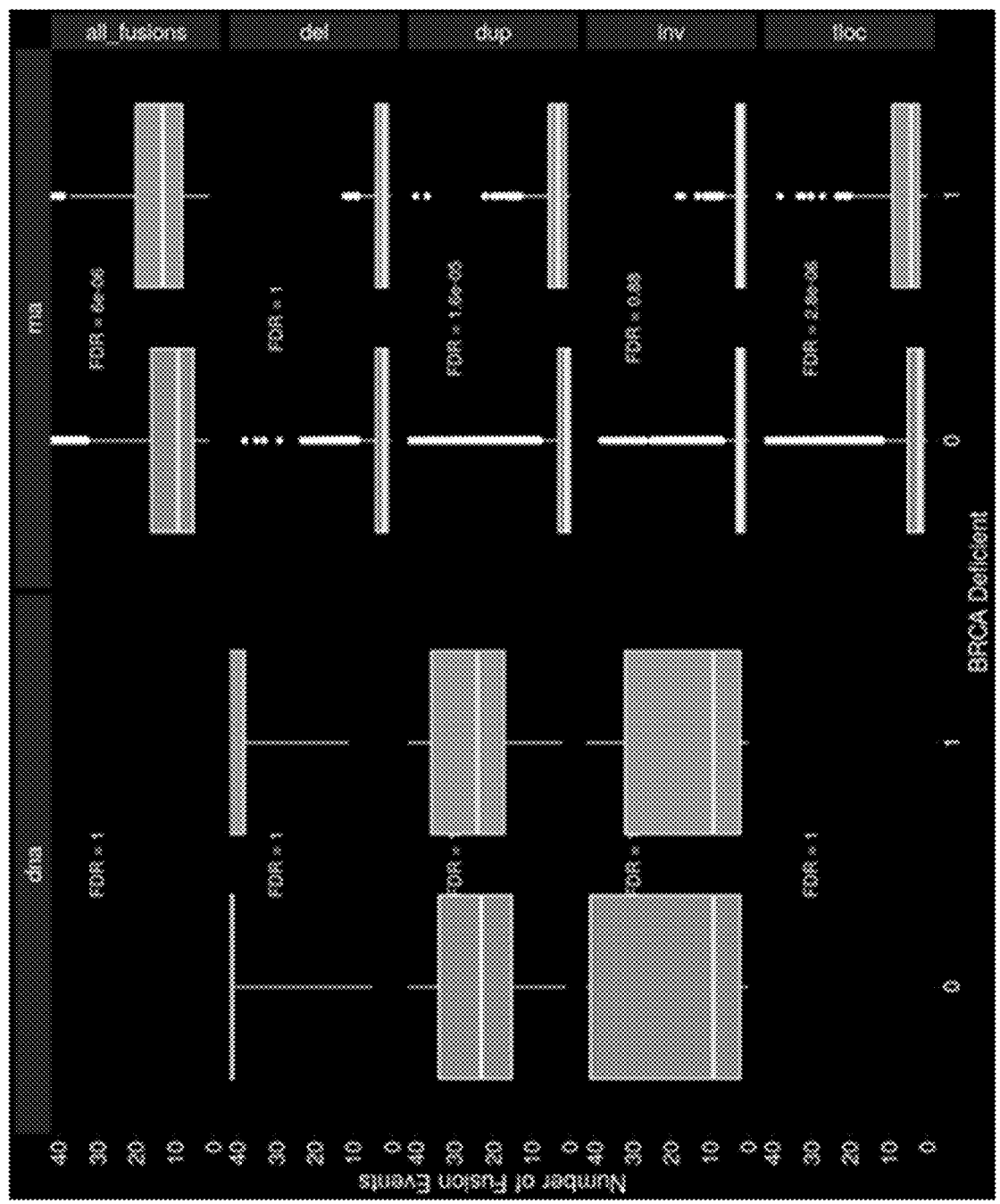
FIG. 10A illustrates the number of fusion events determined using DNA sequencing data (left) and RNA sequencing data (right), in BRCA wild-type (0—top reported statistics) and BRCA deficient (1—bottom reported statistics) cancers. Fusion events were determined for (i) all fusion types, (ii) deletions only, (iii) duplications only, (iv) inversion only, and (v) translocations only.

FIG. 10A illustrates the number of fusion events determined using DNA sequencing data (left) and RNA sequencing data (right), in BRCA wild-type (0—top reported statistics) and BRCA deficient (1—bottom reported statistics) cancers. Fusion events were determined for (i) all fusion types, (ii) deletions only, (iii) duplications only, (iv) inversion only, and (v) translocations only.

Figure 10B:
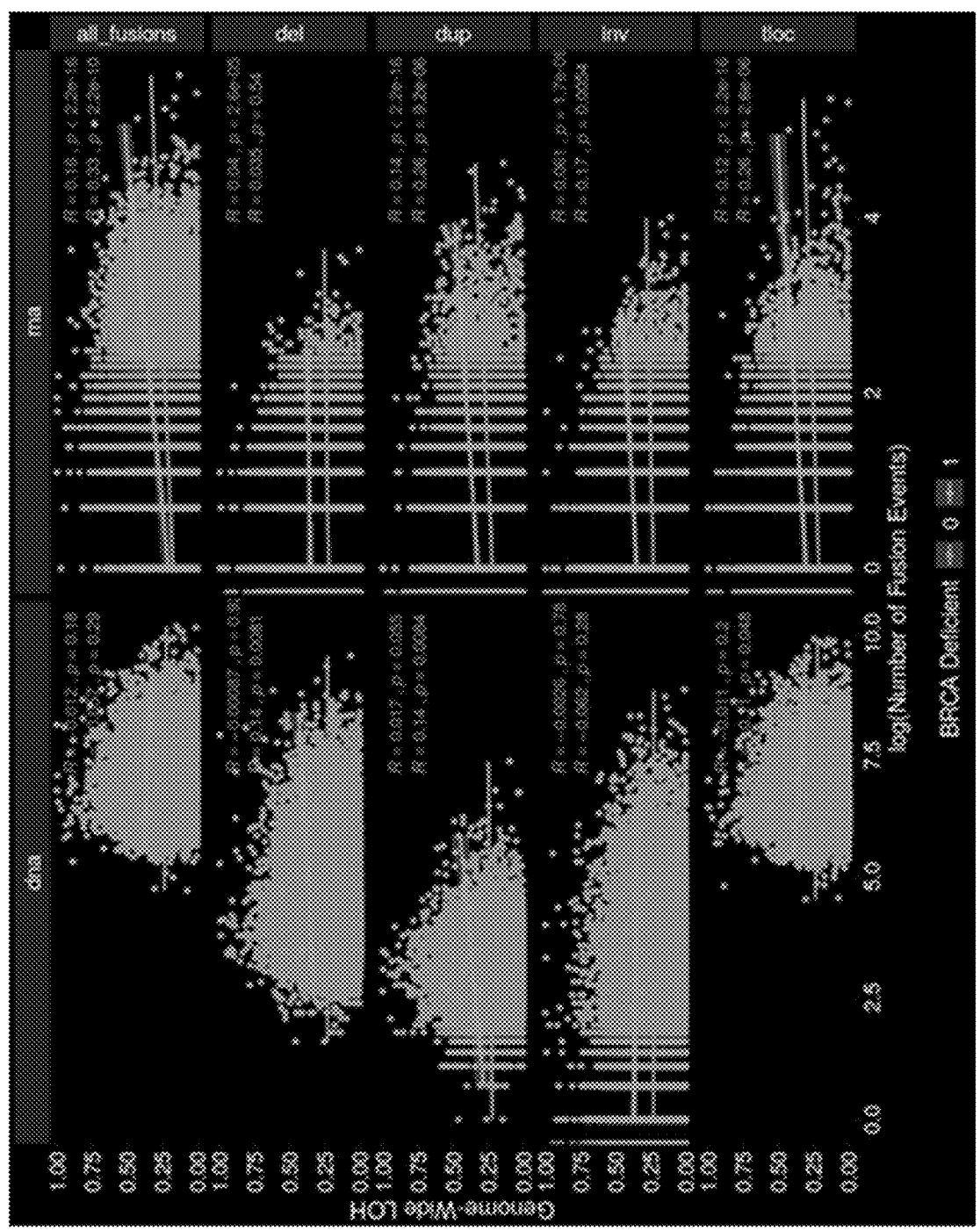
FIG. 10B illustrates association between the number of fusion events determined using DNA sequencing data (left) and RNA sequencing data (right) with gwLOH, in BRCA wild-type (0—top reported statistics) and BRCA deficient (1—bottom reported statistics) cancers. Associations were determined using (i) all fusion types, (ii) deletions only, (iii) duplications only, (iv) inversion only, and (v) translocations only.

FIG. 10B illustrates association between the number of fusion events determined using DNA sequencing data (left) and RNA sequencing data (right) with gwLOH, in BRCA wild-type (0—top reported statistics) and BRCA deficient (1—bottom reported statistics) cancers. Associations were determined using (i) all fusion types, (ii) deletions only, (iii) duplications only, (iv) inversion only, and (v) translocations only.

Example 7—Training an Ensemble Model for Determining a Homologous Recombination Pathway Status of a Cancer Canonically, HRD is primarily known to result from biallelic loss of BRCA1 or of BRCA2. While biallelic loss is definitional of HRD, a number of other factors can result in HRD, including mutation of other DNA repair genes, epigenetic mechanisms, and unknown factors.

An ensemble model for predicting the HRD status of a cancer was trained as a stacked model using outputs from a transcriptome (RNA expression level) model of HRD status and a genome-wide Loss of heterozygosity (gwLOH) model. Samples were only used for training if they were completely wild-type for BRCA1 and BRCA2 (no single nucleotide variants, no short insertions or deletions, and diploid copy number), which are treated as negative, and samples with biallelic inactivation (BRCA-deficient, at least two pathogenic mutations or copy-loss events in either BRCA1 or BRCA2) are treated as positive. While not all BRCA WT samples are expected to be negative, all BRCA deficient samples are expected to be positive. While imperfect in this regard, BRCA status is the most robust available orthogonal proxy for HRD with a long history of use in the field. Cancer labels for each of the samples were also used in the training of the ensemble model, as some variability in transcriptional profiles and loss of heterozygosity is attributable to the type of cancer, rather than the HRD status of the cancer.

Samples for training data were also chosen based on having at least 30% final tumor purity, to ensure strong tumor transcriptome signal and accurate GWLOH % calculation.

Figure 14A:
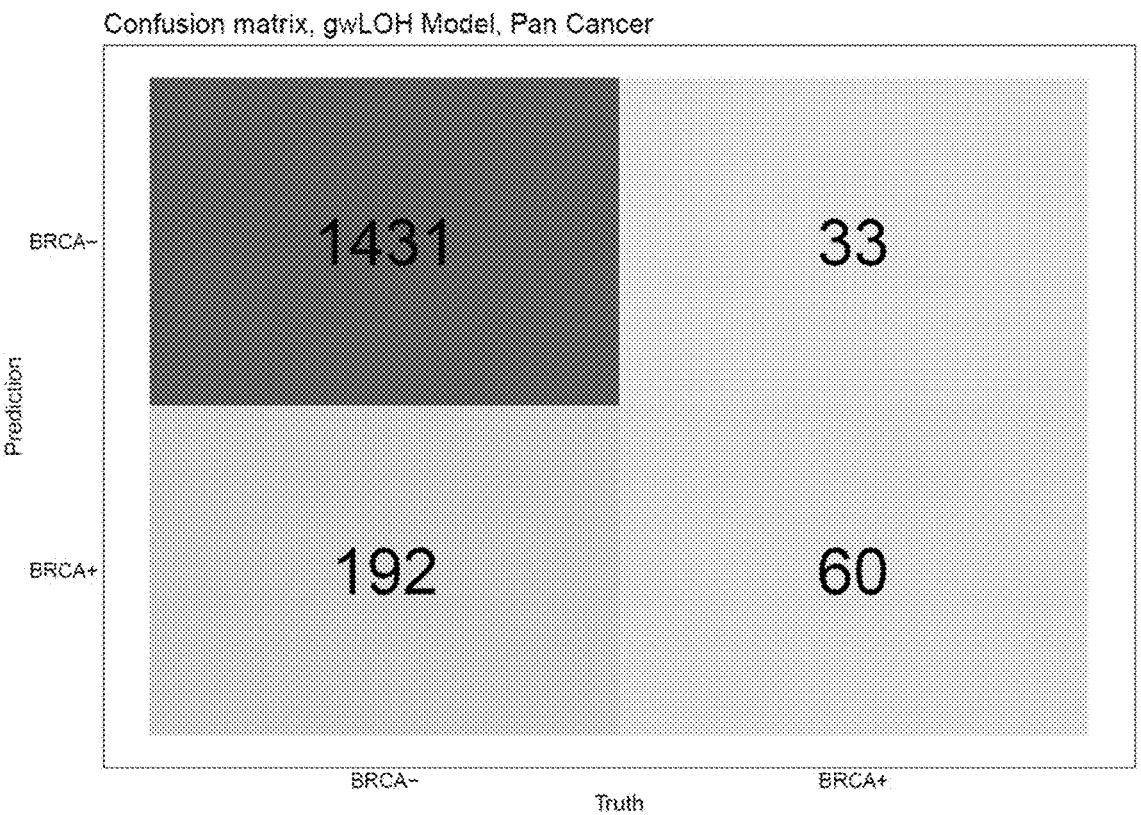
FIGS. 14A, 14B, 14C, 14D, 14E, 14F, 14G, 14H, 14I, 14J, 14K, 14L, 14M, 14N, 14O, 14P, 14Q, 14R, 14S, 14T, and 14U illustrate confusion matrices for the performance of either the genome-wide loss of heterozygosity (gwLOH) model based on DNA data, a model based on RNA data, or a stacked model based on both the gwLOH and RNA models, where each model is either a pan-cancer model or a model generated specifically for a single cancer cohort (see chart title in each figure).
Figure 14B:
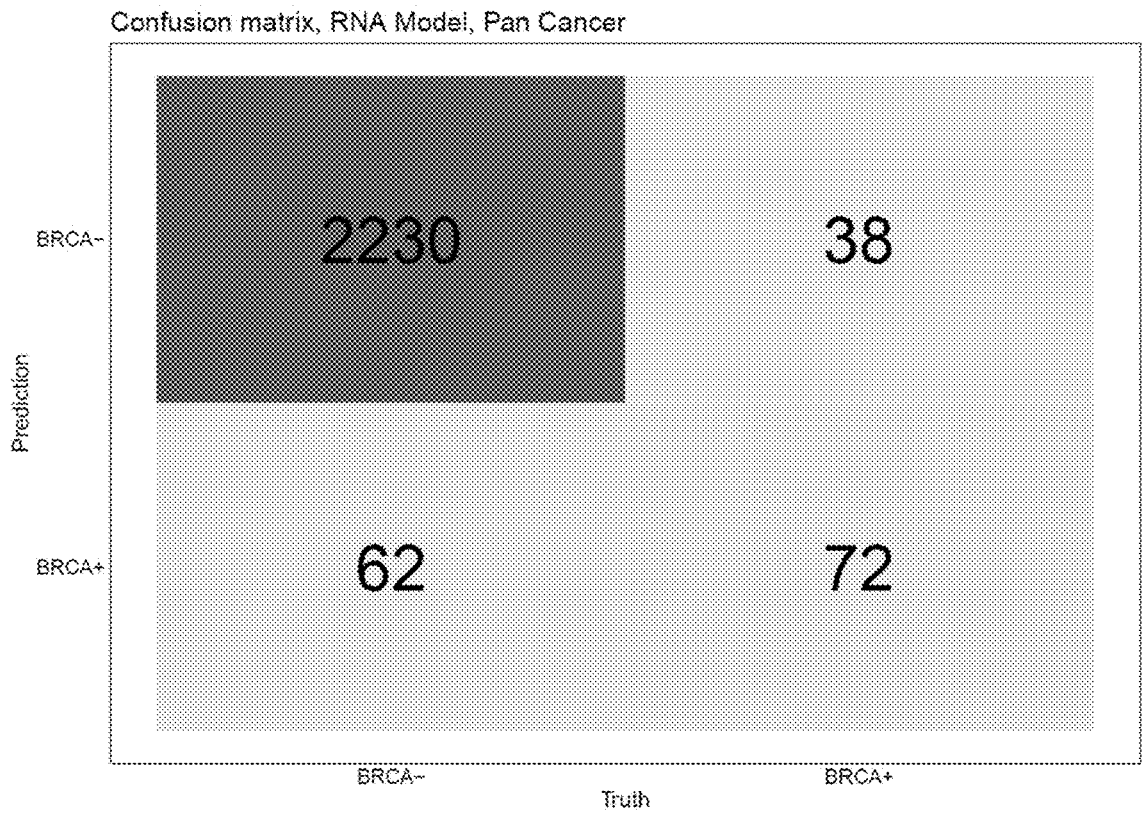
Figure 14C:
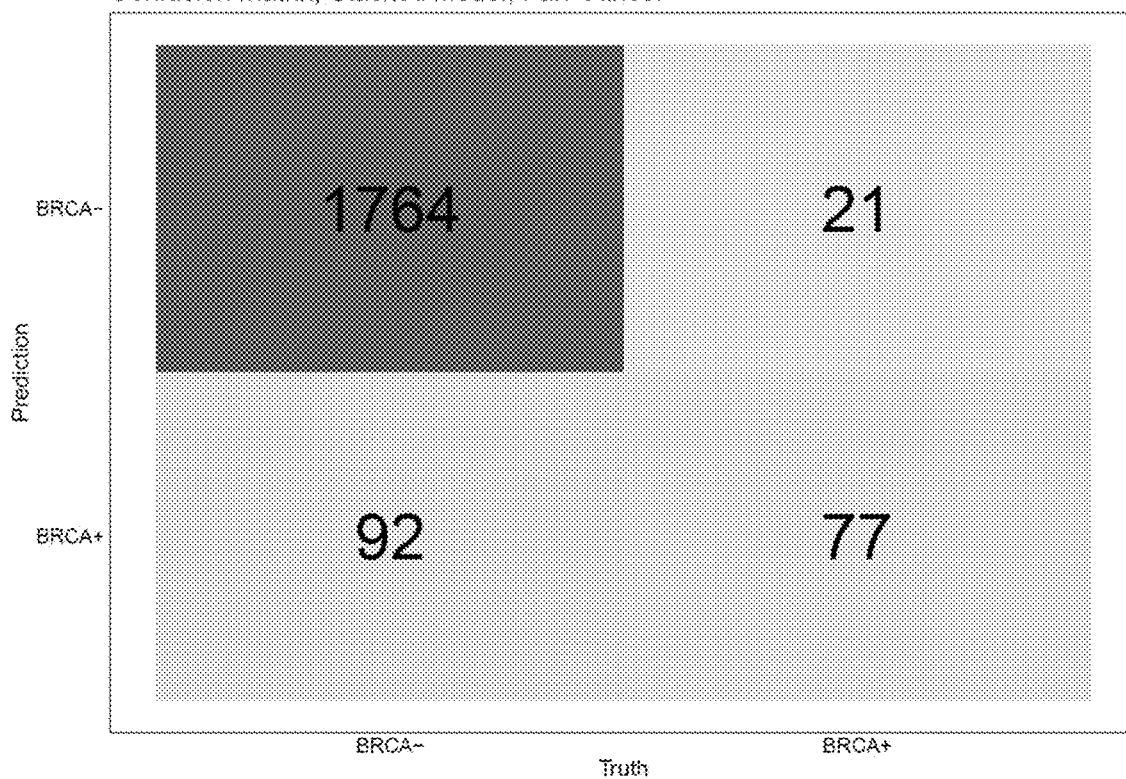
Figure 14D:
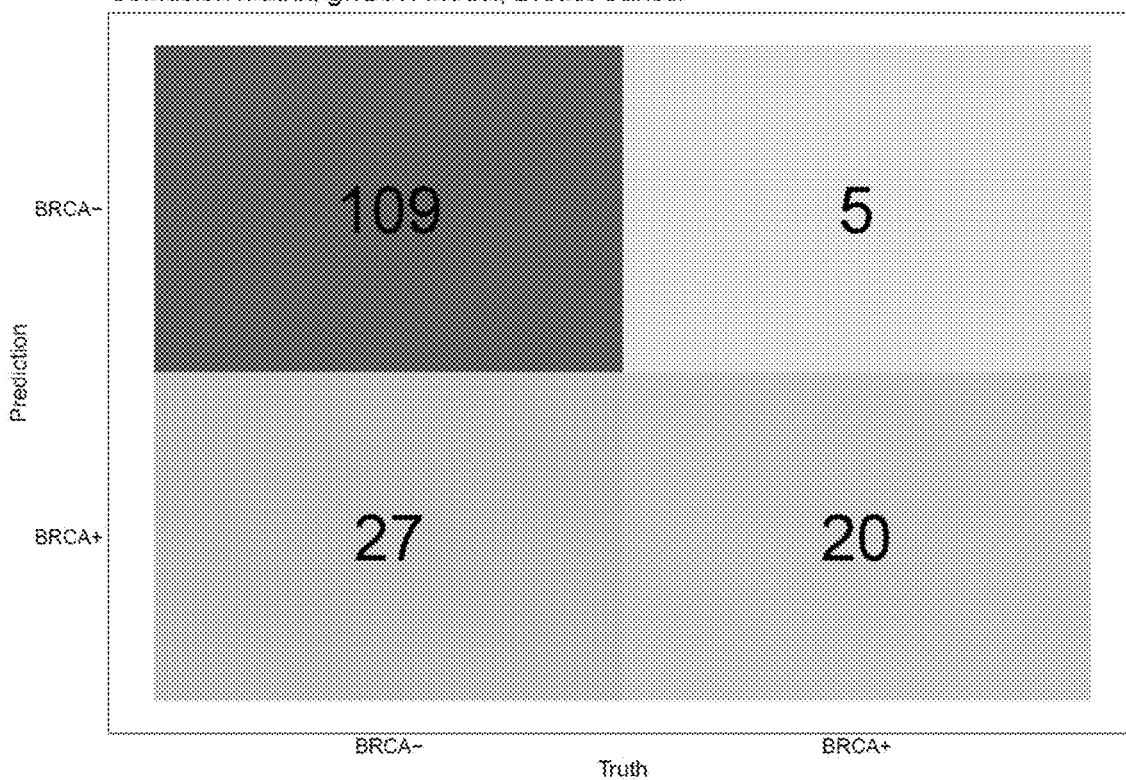
Figure 14E:
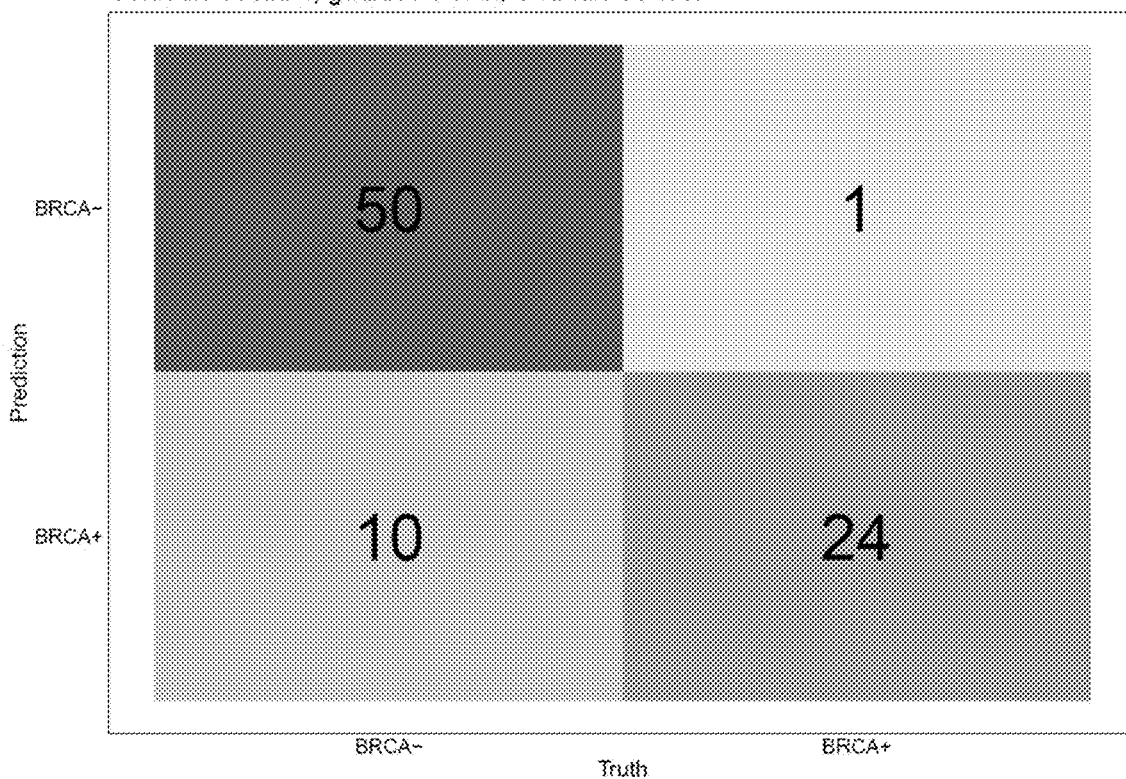
Figure 14F:
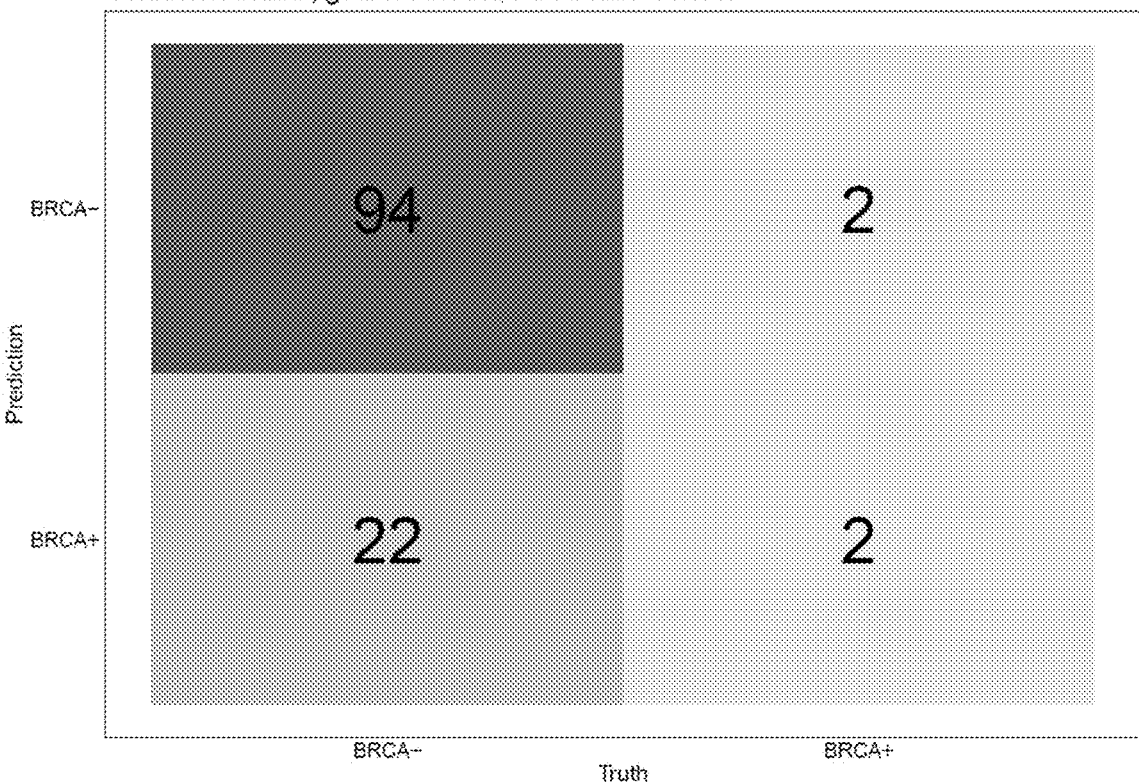
Figure 14G:
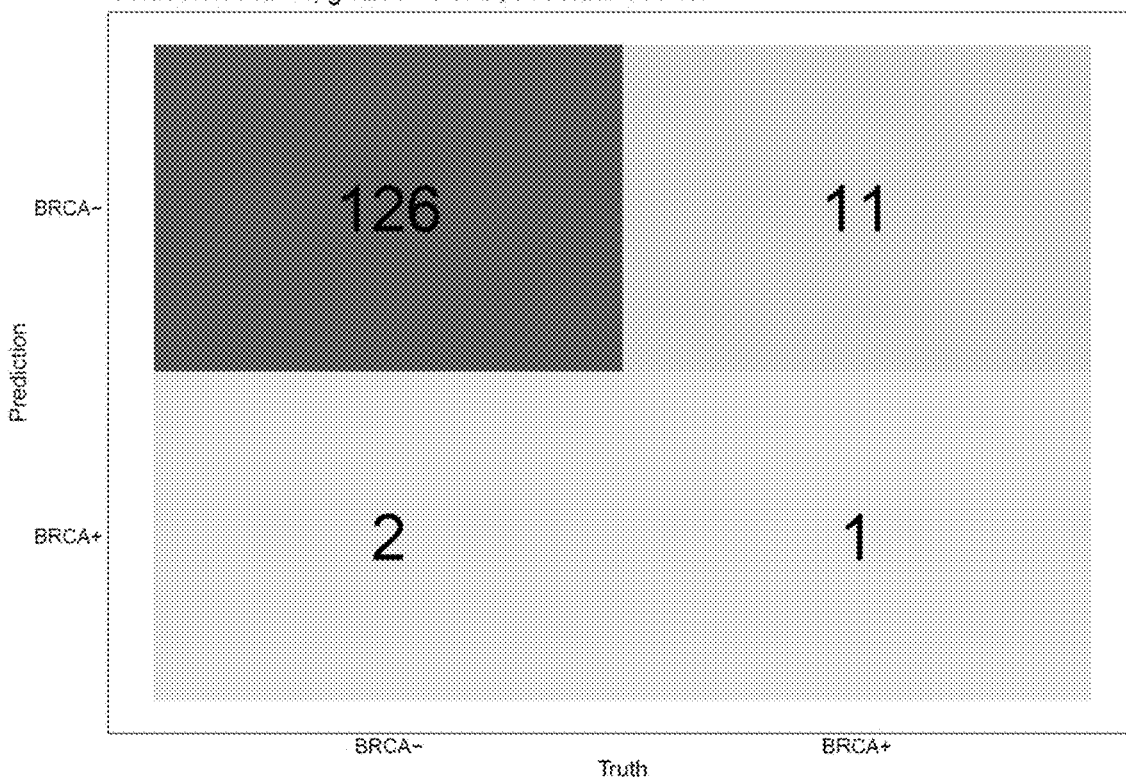
Figure 14H:
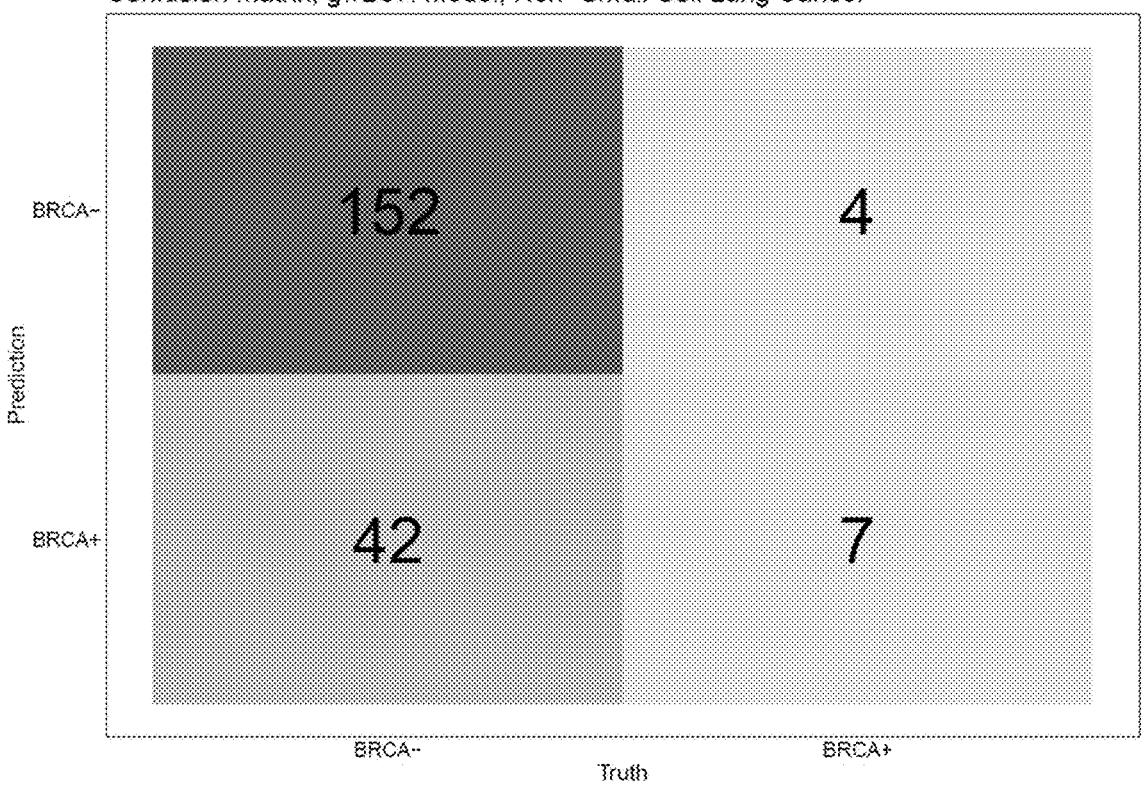
Figure 14I:
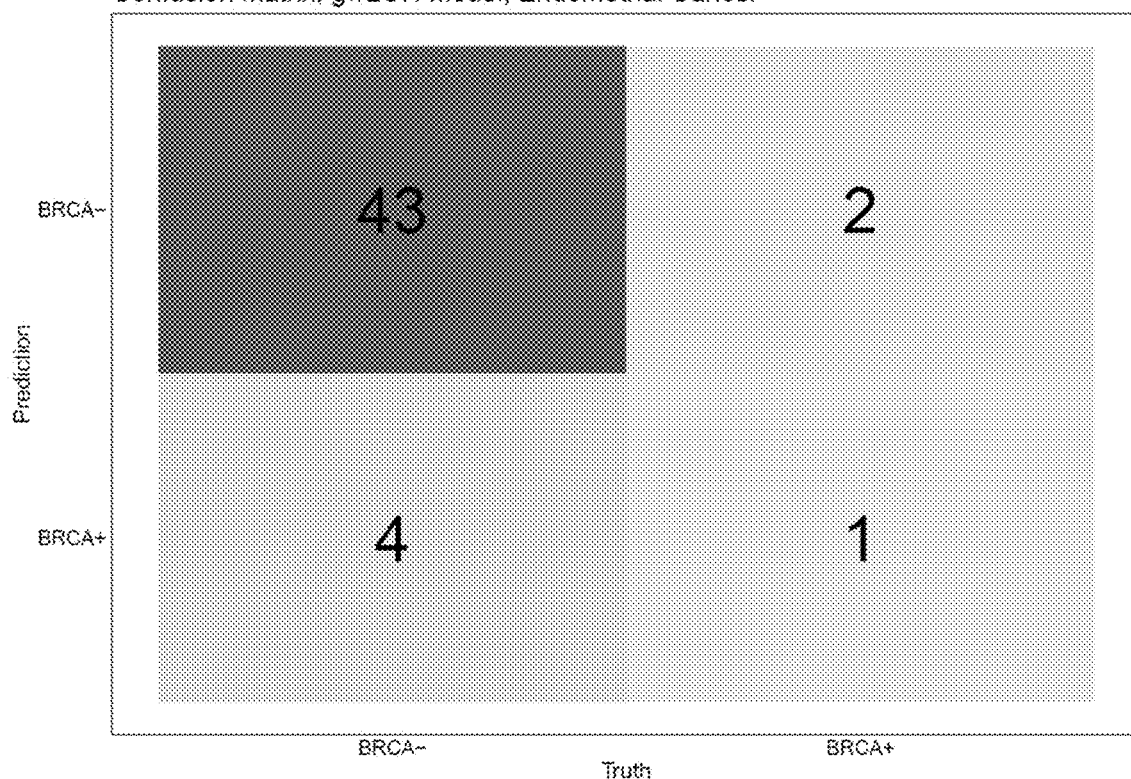
Figure 14J:
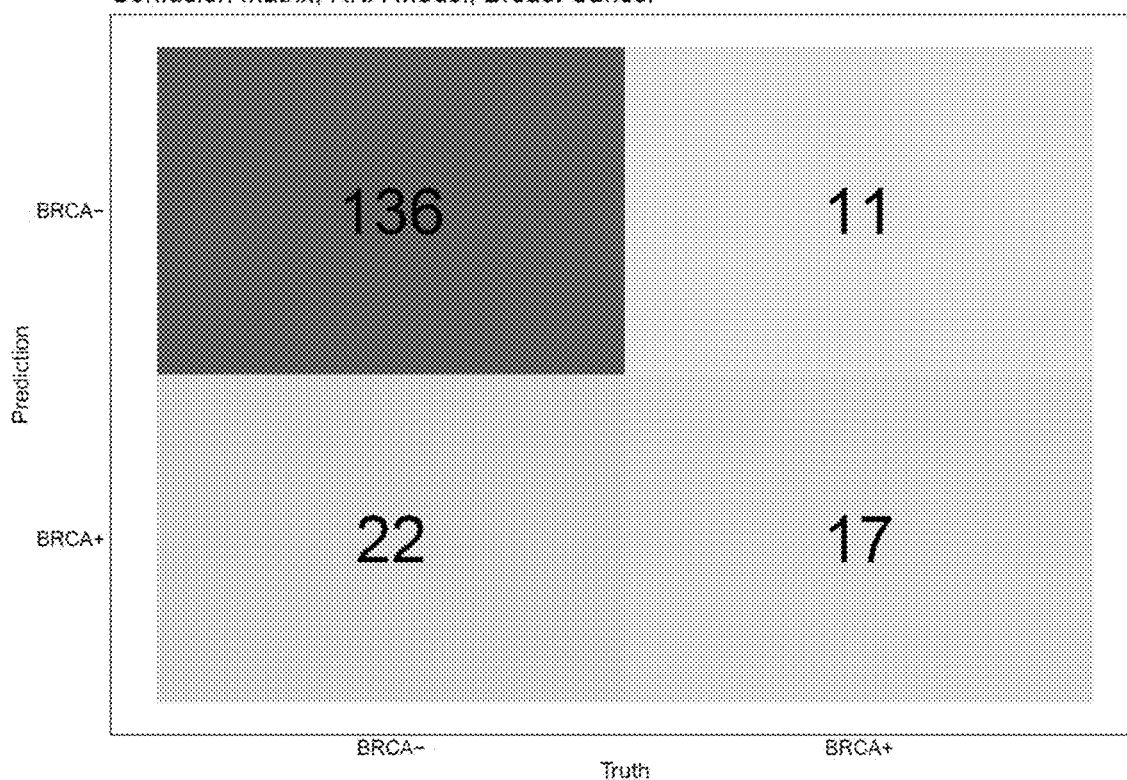
Figure 14K:
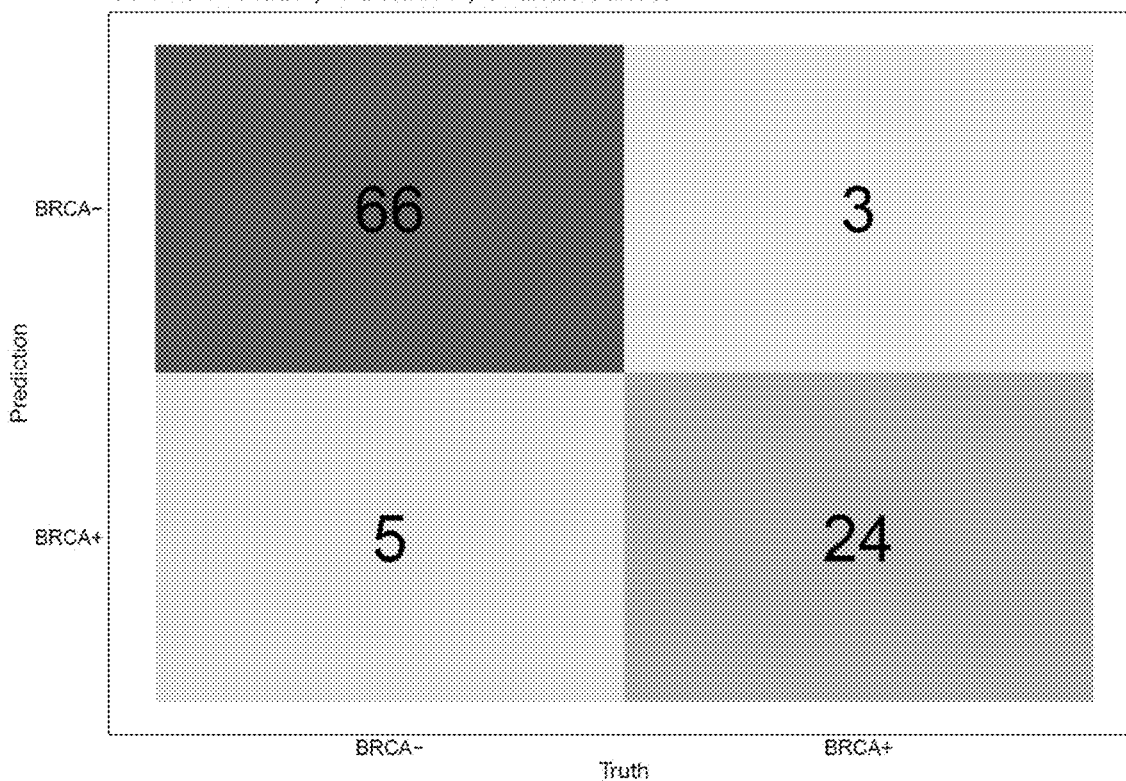
Figure 14L:
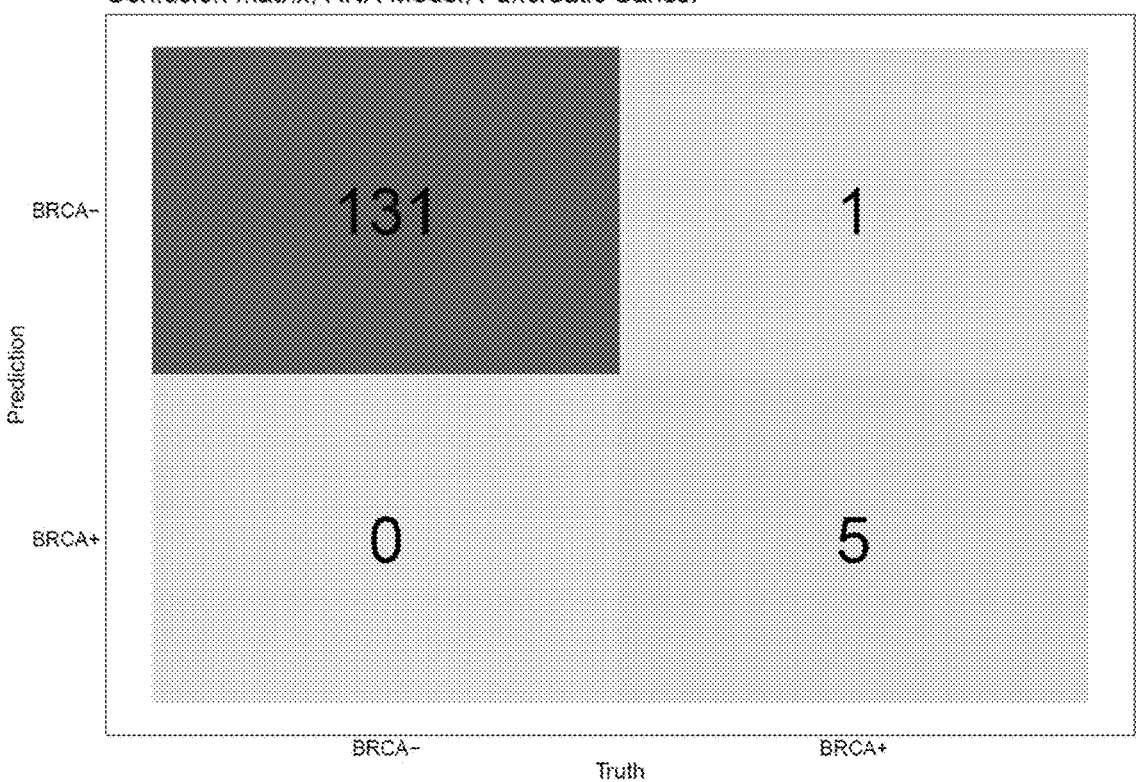
Figure 14M:
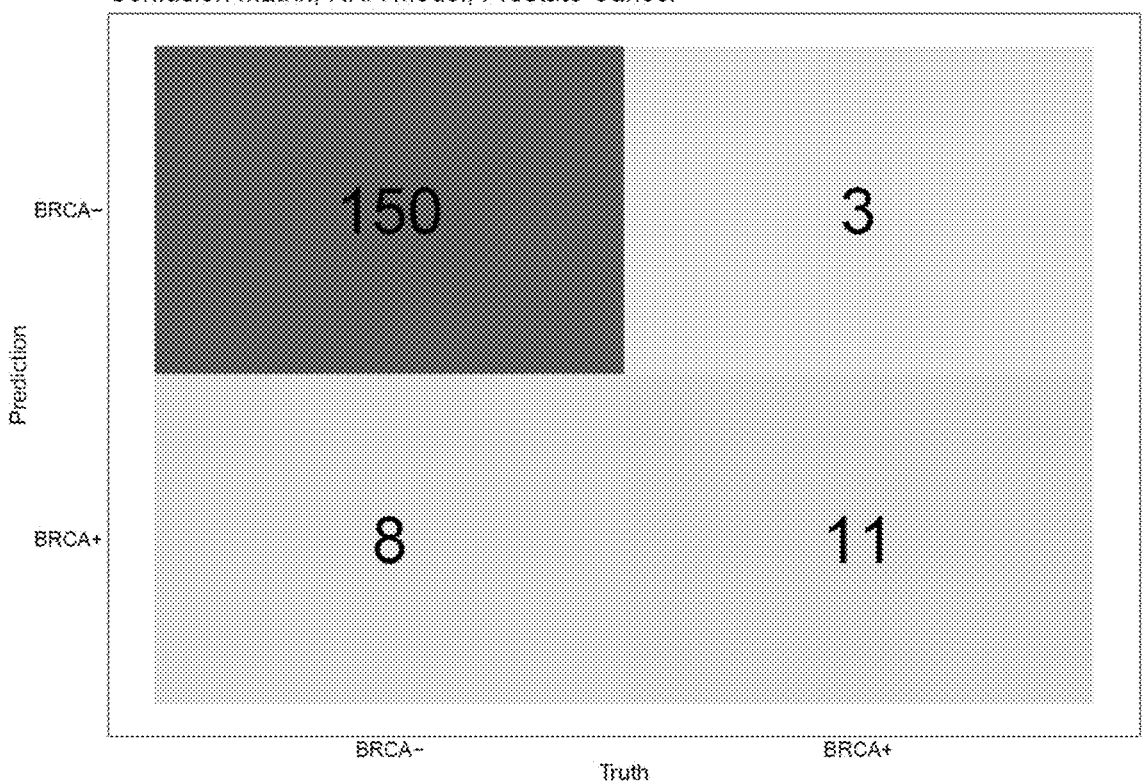
Figure 14N:
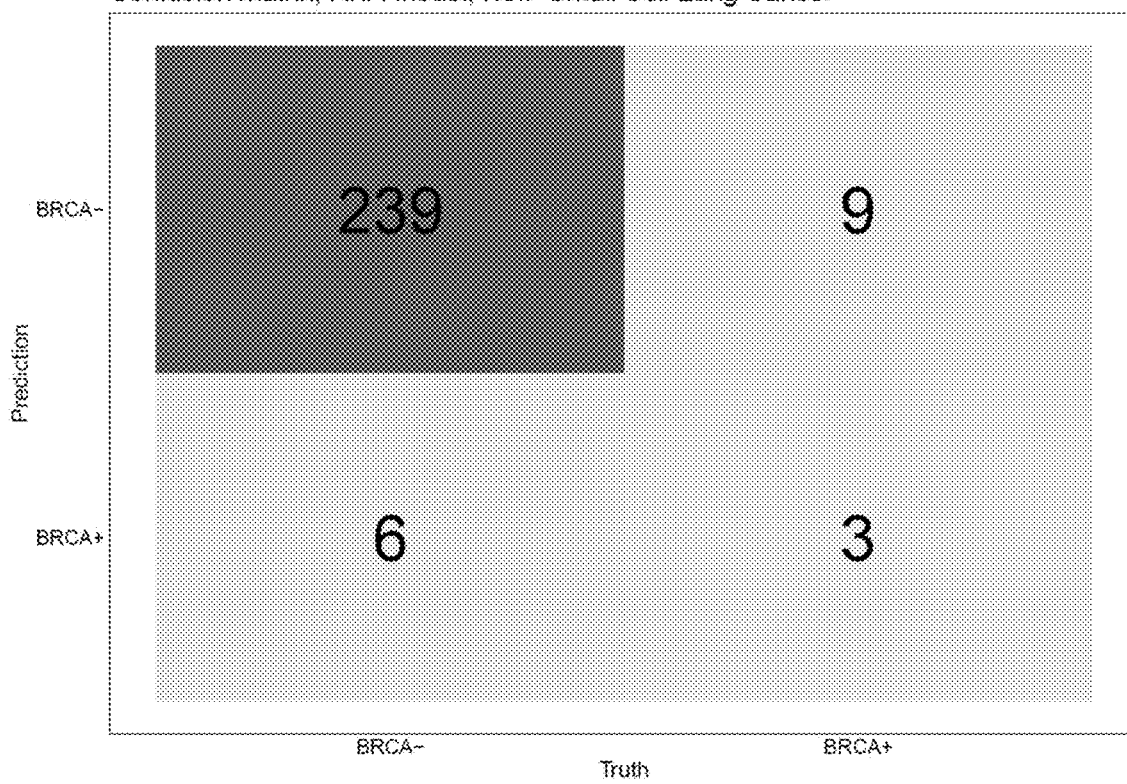
Figure 14O:
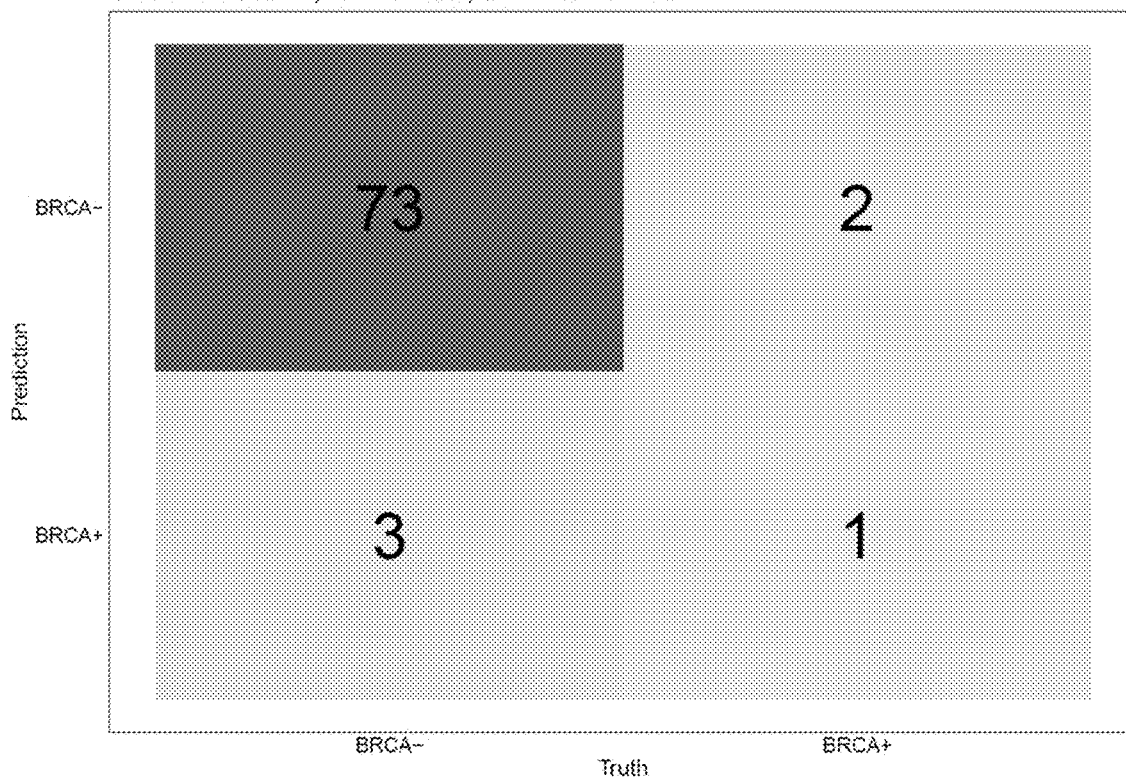
Figure 14P:
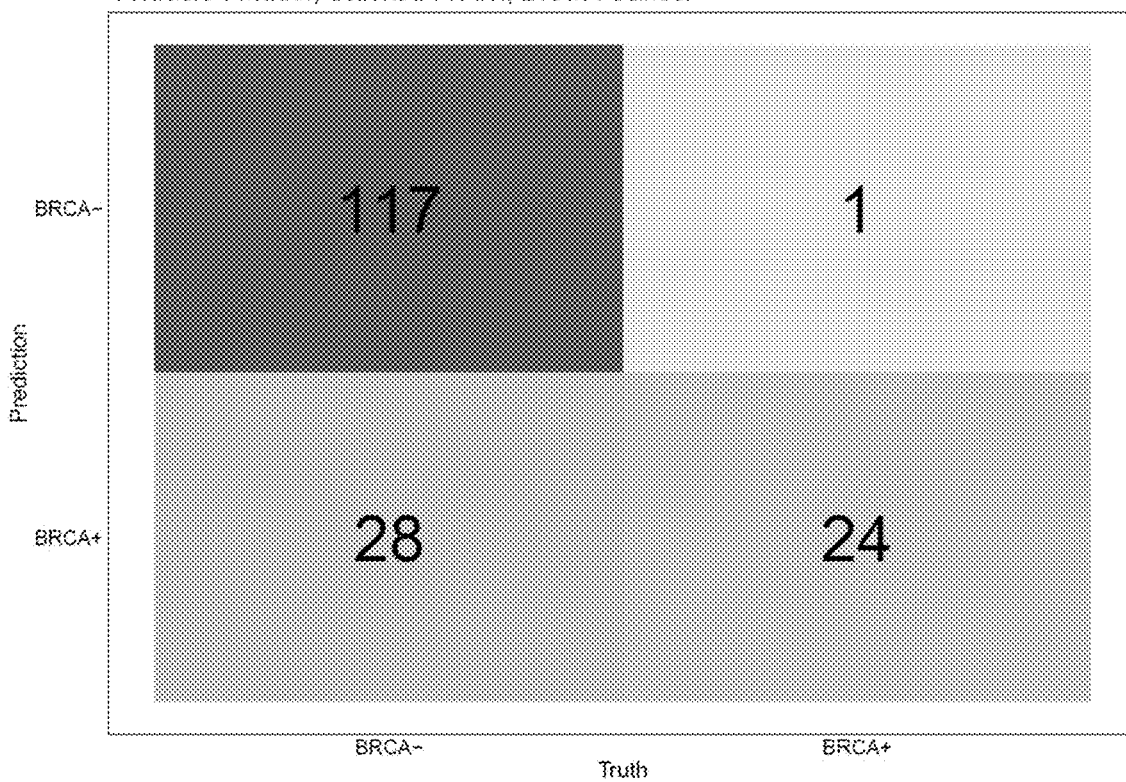
Figure 14Q:
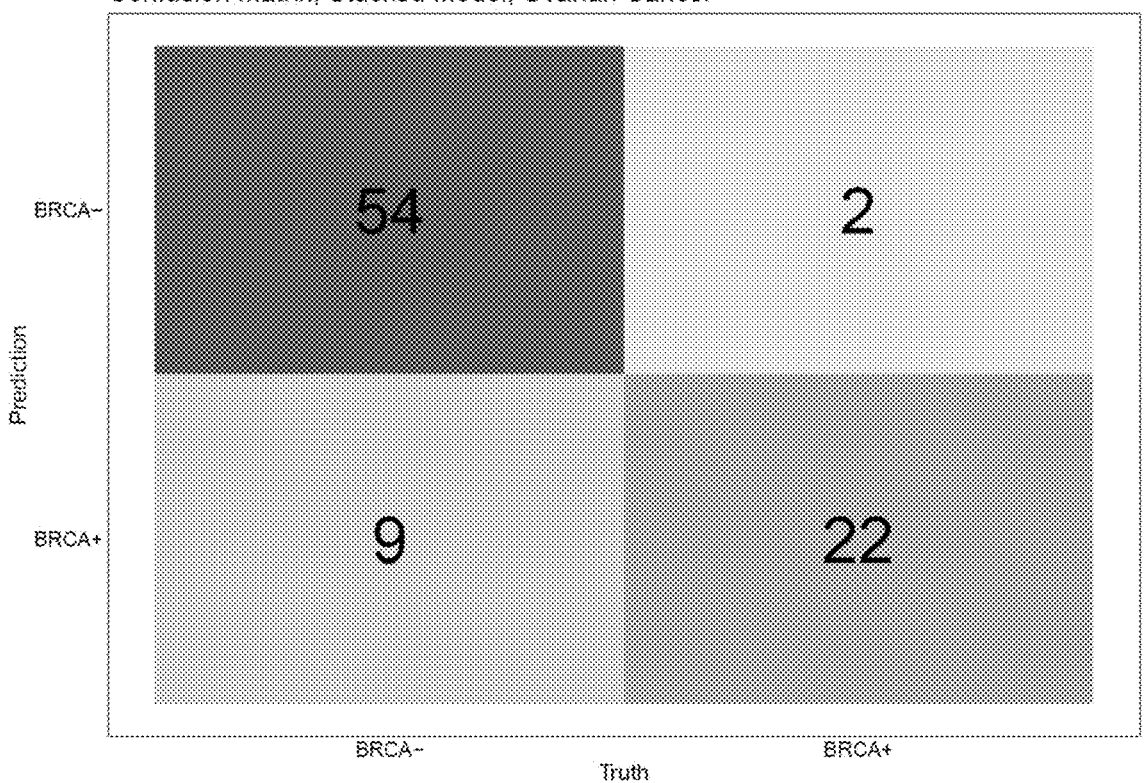
Figure 14R:
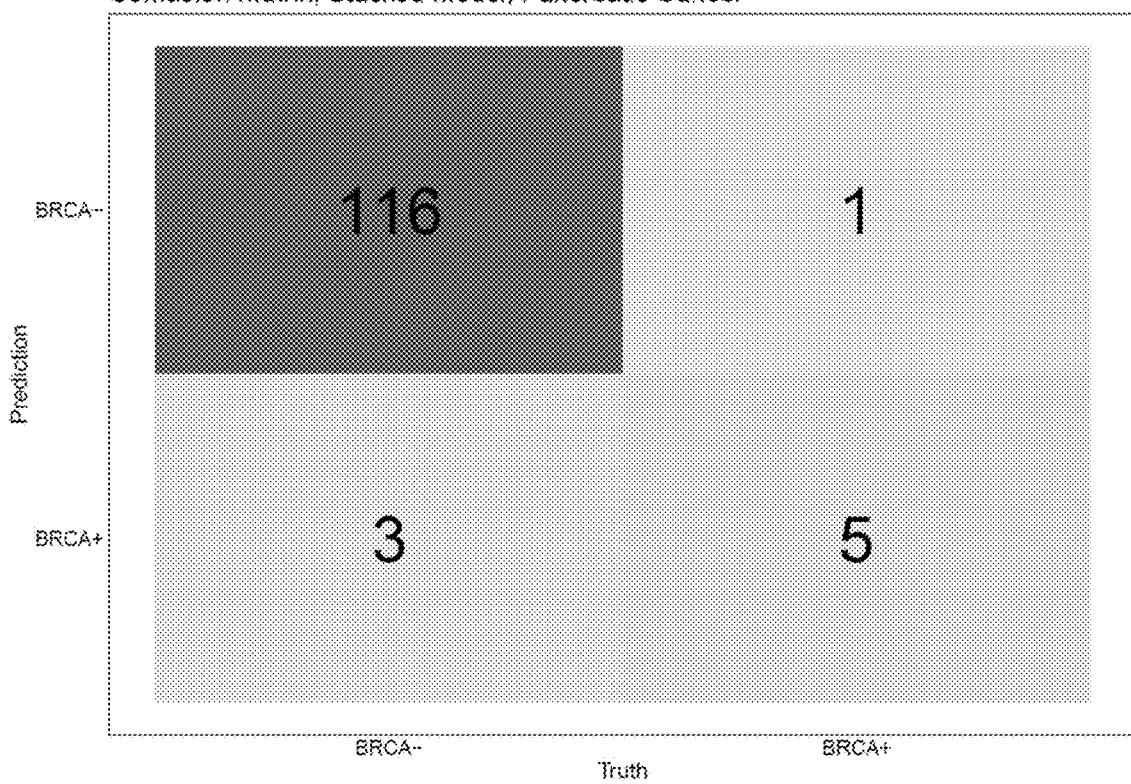
Figure 14S:
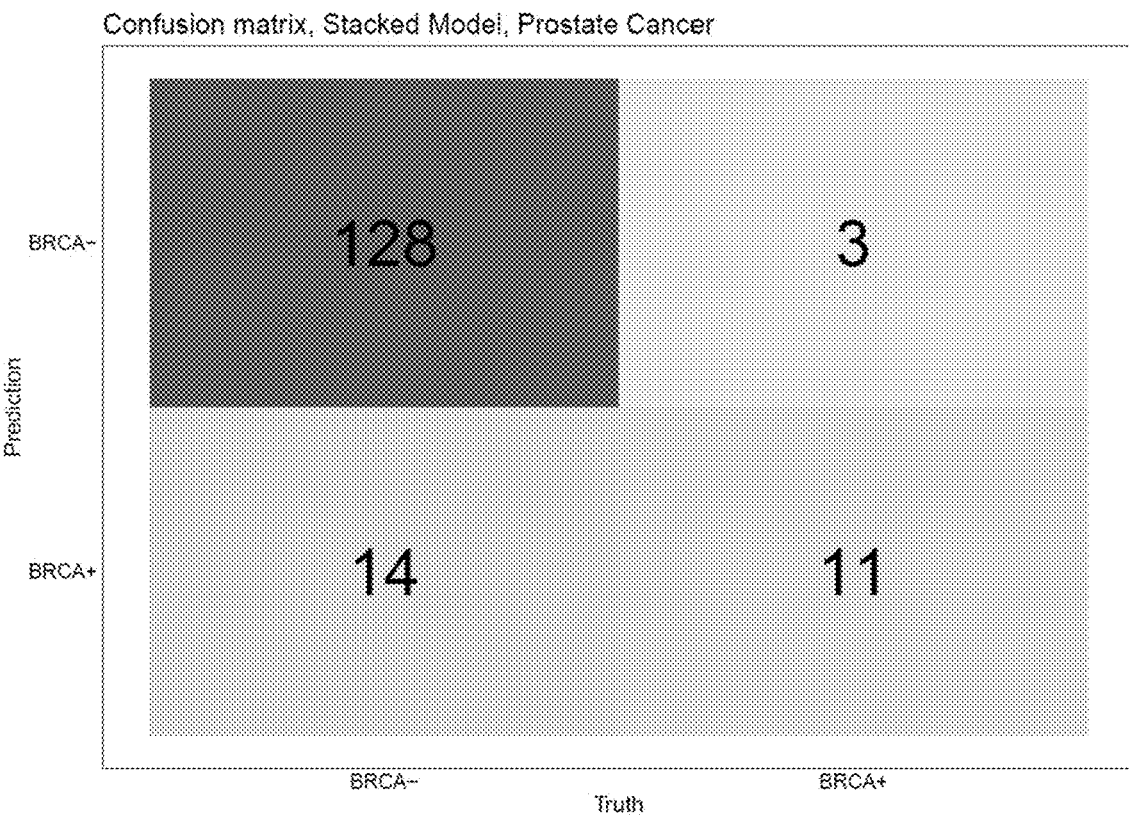
Figure 14T:
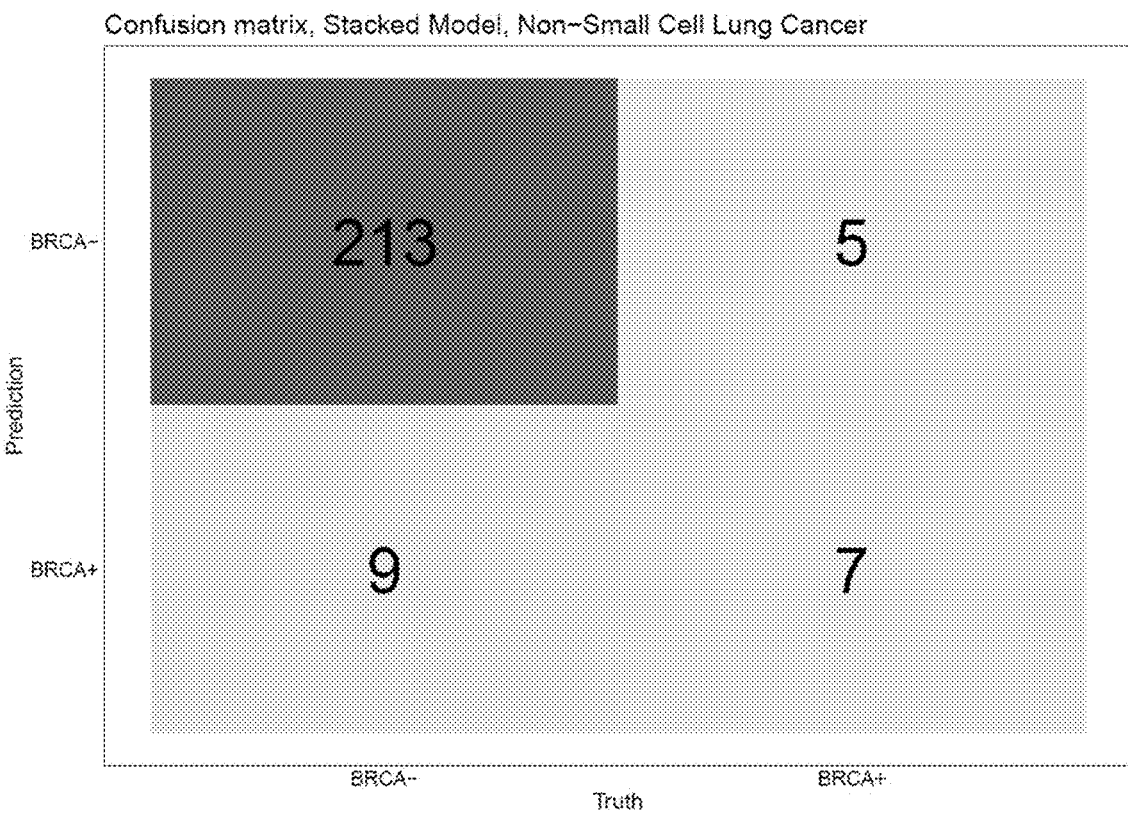
Figure 14U:
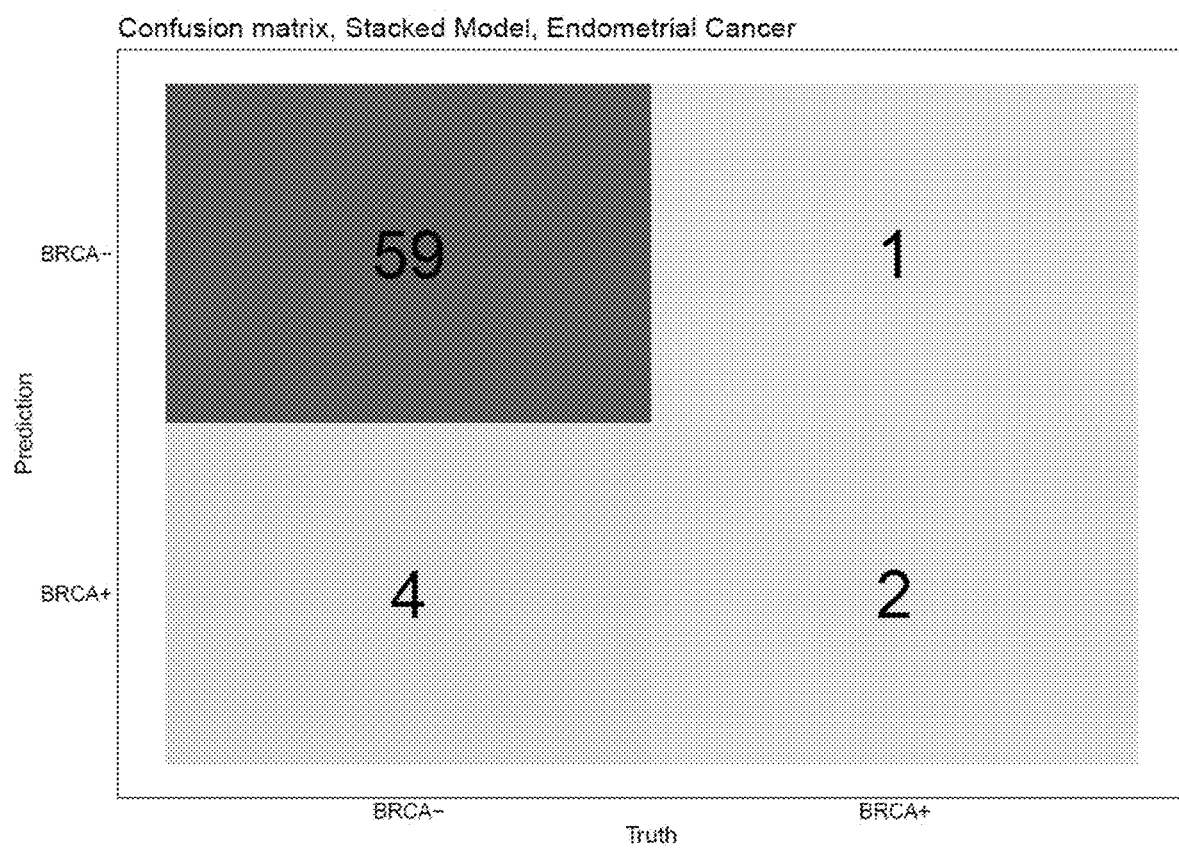
Figure 16:
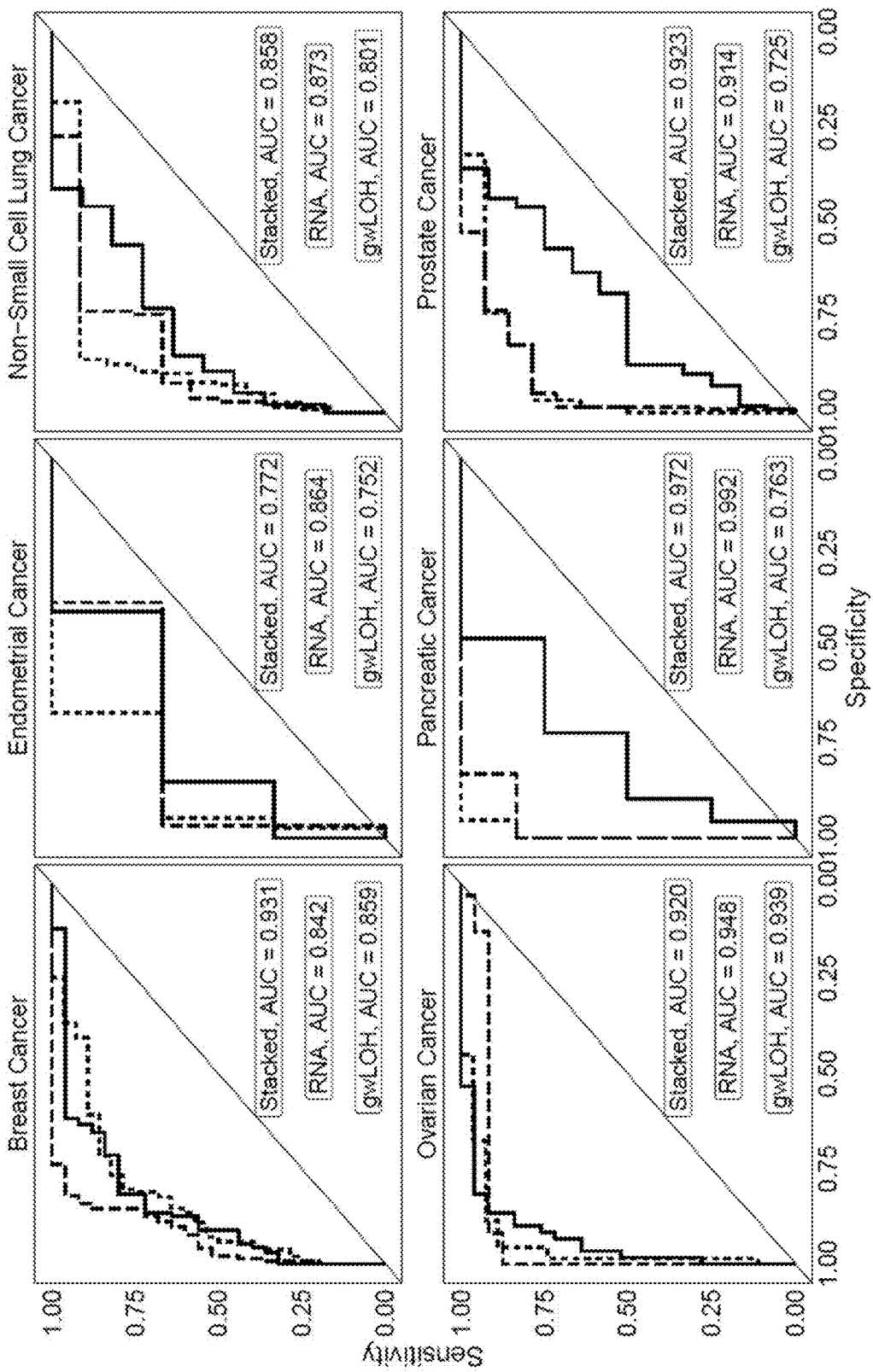
FIG. 16 illustrates ROC curves and provides AUC calculations for the performance of each individual model, as well as the stacked ensemble model, on single cancer-type cohorts, again using bi-allelic inactivation as a proxy for HRD+ status.

To hone in on the transcriptomic signal of HRD, the ~20,000 genes for which transcriptome-level RNAseq data is available for were prioritized based on which had the highest coefficient absolute values from a logistic regression trained on subsets of the training data. After feature prioritization, the transcriptome model was free to select from the genes with highest priority. The number of features selected was tuned, along with class weight and regularization strength, to maximize overall model sensitivity FIGS. 14A-14C illustrate confusion matrices for the performance of each individual model, as well as the stacked ensemble model, on a pan cancer cohort, where ground truth HRD status is defined using bi-allelic inactivation (BRCA-deficient, at least two pathogenic mutations or copy-loss events in either BRCA1 or BRCA2) as a proxy for HRD+ status, as described above. FIGS. 14D-14U 16 illustrate confusion matrices for the performance of each individual model, as well as the stacked ensemble model, on single cancer-type cohorts, again using bi-allelic inactivation as a proxy for HRD+ status.

Figure 15:
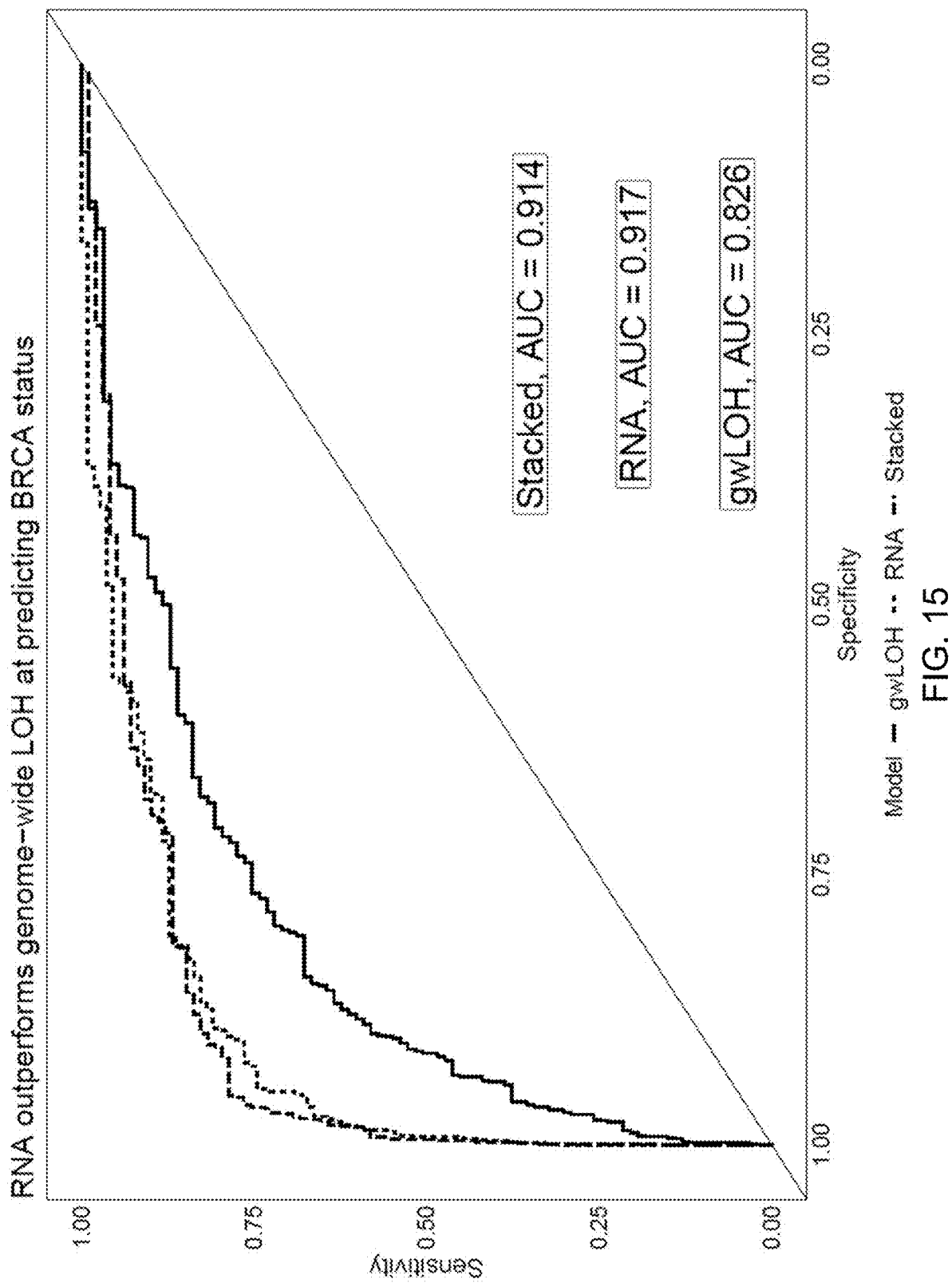
FIG. 15 illustrates ROC curves and provides AUC calculations for the performance of each individual model, as well as the stacked ensemble model, on a pan cancer cohort, where ground truth HRD status is defined using bi-allelic inactivation (BRCA-deficient, at least two pathogenic mutations or copy-loss events in either BRCA1 or BRCA2) as a proxy for HRD+ status.

FIG. 15 illustrates ROC curves and provides AUC calculations for the performance of each individual model, as well as the stacked ensemble model, on a pan cancer cohort, where ground truth HRD status is defined using bi-allelic inactivation (BRCA-deficient, at least two pathogenic mutations or copy-loss events in either BRCA1 or BRCA2) as a proxy for HRD+ status, as described above. FIG. 16 illustrates ROC curves and provides AUC calculations for the performance of each individual model, as well as the stacked ensemble model, on single cancer-type cohorts, again using bi-allelic inactivation as a proxy for HRD+ status.

Figure 17:
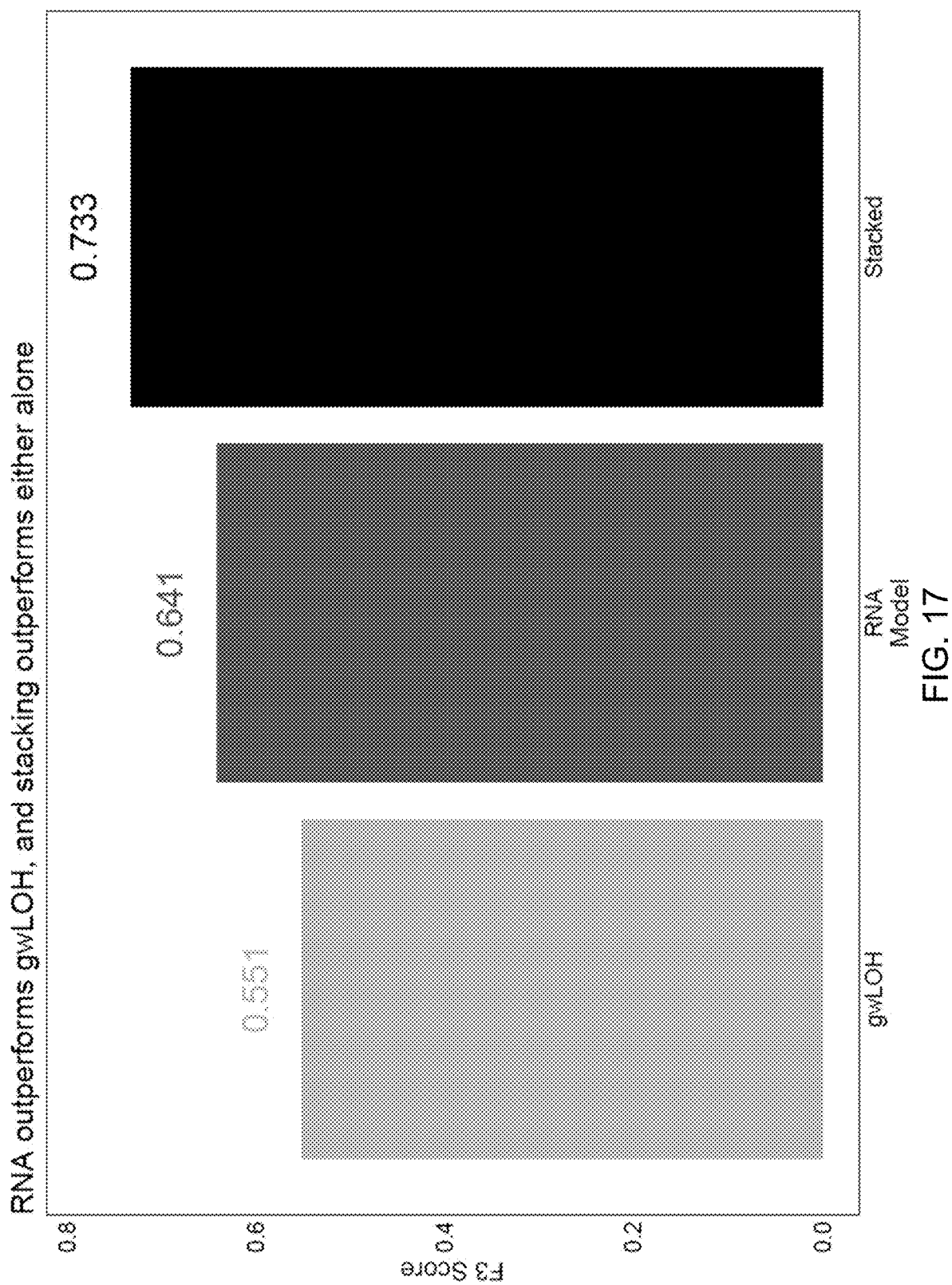
FIG. 17 illustrates F3 scores for the performance of each individual model, as well as the stacked ensemble model, on a pan cancer validation cohort, where ground truth HRD status is defined using bi-allelic inactivation (BRCA-deficient, at least two pathogenic mutations or copy-loss events in either BRCA1 or BRCA2) as a proxy for HRD+ status.
Figure 18:
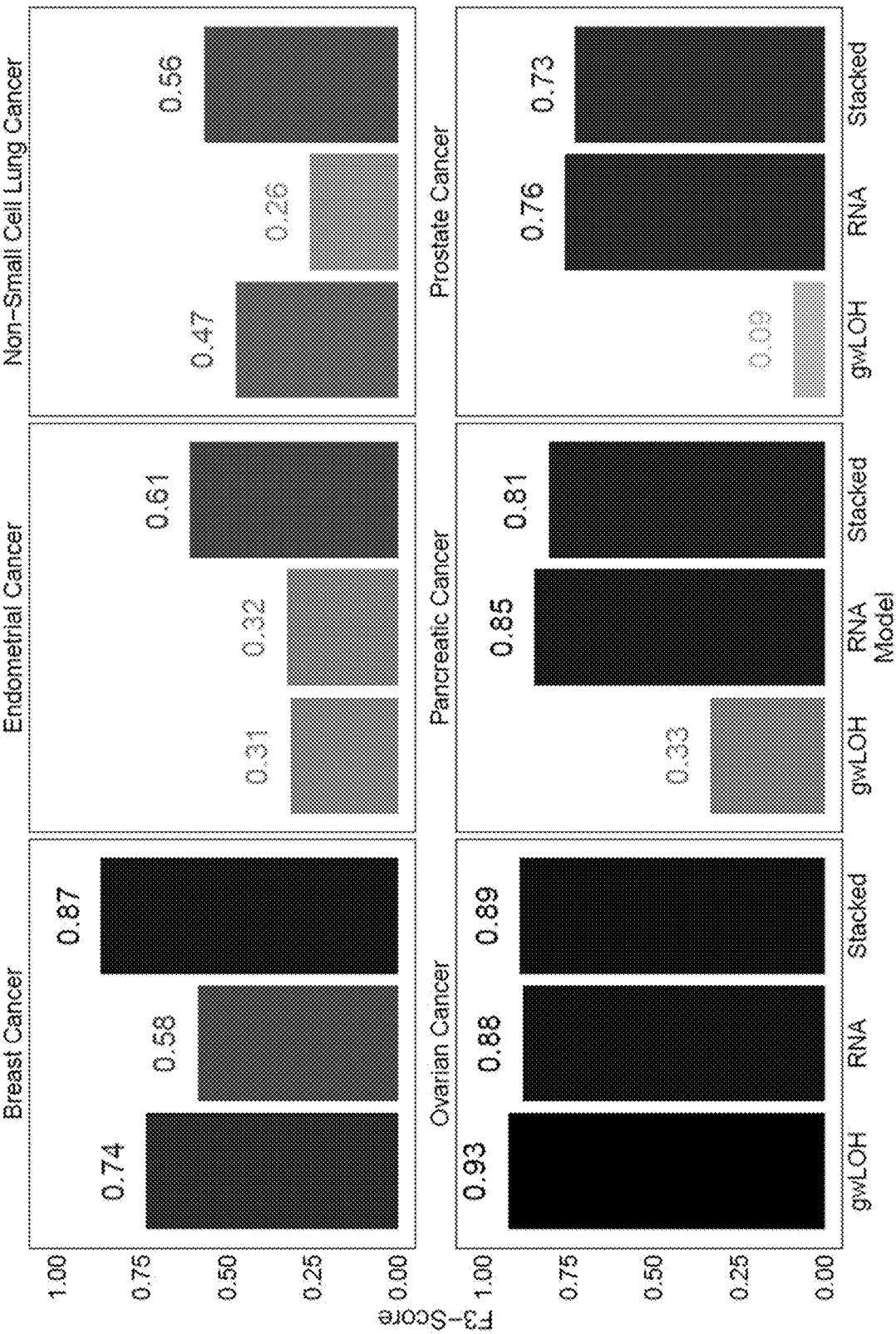
FIG. 18 illustrates F3 scores for the performance of each individual model, as well as the stacked ensemble model, on single cancer-type validation cohorts, again using bi-allelic inactivation as a proxy for HRD+ status.

FIG. 17 illustrates F3 scores for the performance of each individual model, as well as the stacked ensemble model, on a pan cancer validation cohort, where ground truth HRD status is defined using bi-allelic inactivation (BRCA-deficient, at least two pathogenic mutations or copy-loss events in either BRCA1 or BRCA2) as a proxy for HRD+ status, as described above. FIG. 18 illustrates F3 scores for the performance of each individual model, as well as the stacked ensemble model, on single cancer-type validation cohorts, again using bi-allelic inactivation as a proxy for HRD+ status.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

Another aspect of the present disclosure provides a computer system comprising one or more processors, and a non-transitory computer-readable medium including computer-executable instructions that, when executed by the one or more processors, cause the processors to perform a method according to any one of the embodiments disclosed herein, and/or any combinations, modifications, substitutions, additions, or deletions thereof as will be apparent to one skilled in the art.

Another aspect of the present disclosure provides a non-transitory computer-readable storage medium having stored thereon program code instructions that, when executed by a processor, cause the processor to perform the method according to any one of the embodiments disclosed herein, and/or any combinations, modifications, substitutions, additions, or deletions thereof as will be apparent to one skilled in the art.

The present invention can be implemented as a computer program product that comprises a computer program mechanism embedded in a non-transitory computer readable storage medium. For instance, the computer program product could contain the program modules shown in any combination in FIG. 1 and/or as described elsewhere within the application. These program modules can be stored on a CD-ROM, DVD, magnetic disk storage product, USB key, or any other non-transitory computer readable data or program storage product.

Many modifications and variations of this disclosure can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The disclosure is to be limited only by the terms of the appended claims, along with the full scope of equivalents to which such claims are entitled.

What is claimed is:

1. A method of obtaining a homologous recombination pathway status of a cancer in a test subject, the method comprising:
   at a computer system having one or more processors, and memory storing one or more programs for execution by the one or more processors:
   (A) obtaining a first plurality of at least 10,000 sequence reads, in electronic form, of a DNA sample from the test subject, the DNA sample comprising DNA molecules from a cancerous tissue of the subject;
   (B) obtaining a second plurality of at least 10,000 sequence reads, in electronic, of an RNA sample from the test subject, the RNA sample comprising RNA molecules from the cancerous tissue of the subject; and
   (C) evaluating the first plurality of at least 10,000 sequence reads and the second plurality of at least 10,000 sequence reads using an ensemble model trained to distinguish between cancers with homologous recombination pathway deficiencies and cancers without homologous recombination pathway deficiencies, wherein the evaluating comprises:
      determining, using the first plurality of at least 10,000 sequence reads, a first prediction for the homologous recombination pathway status of the cancerous tissue of the subject based on a measure of genome-wide loss of heterozygosity for the cancerous tissue of the subject;
      determining, using the second plurality of at least 10,000 sequence reads, a second prediction for the homologous recombination pathway status of the cancerous tissue of the subject based on the expression levels of a plurality of genes in the cancerous tissue of the subject;
      determining, using the second plurality of at least 10,000 sequence reads, a third prediction for the homologous recombination pathway status of the cancerous tissue of the subject based on a measure of transcriptome-wide rearrangements for the cancerous tissue of the subject; and
      determining a final prediction for the homologous recombination pathway status based on the first prediction, the second prediction, and the third prediction,
   thereby obtaining the homologous recombination pathway status of the test subject as an output of the ensemble model.

2. The method of claim 1, wherein the measure of transcriptome-wide rearrangements is a measure of sequence insertions, sequence deletions, sequence inversions, and sequence translocations identified in the second plurality of sequence reads.

3. The method of claim 1, wherein:
   the method further comprises determining, based on the first plurality of at least 10,000 sequence reads, a fourth prediction for the homologous recombination pathway status of the cancerous tissue of the subject based on a measure of genome-wide rearrangements for the cancerous tissue of the subject; and
   the final prediction is further based on the fourth prediction for the homologous recombination pathway status of the cancerous tissue of the subject.

4. The method of claim 3, wherein the measure of genome-wide rearrangements is a measure of sequence insertions, sequence deletions, sequence inversions, and sequence translocations identified in the first plurality of sequence reads.

5. The method of claim 1, wherein determining the third prediction is further based on a cancer type of the cancerous tissue of the subject.

6. The method of claim 1, wherein:
   the method further comprises determining, based on the second plurality of at least 10,000 sequence reads, a fourth prediction for the homologous recombination pathway status of the cancerous tissue of the subject based on a plurality of single-sample gene set enrichment analysis (ssGSEA) scores for the transcriptional profile of the cancerous tissue of the subject; and
   the final prediction is further based on the fourth prediction for the homologous recombination pathway status of the cancerous tissue of the subject.

7. The method of claim 6, wherein determining the fourth prediction is further based on a cancer type of the cancerous tissue of the subject.

8. The method of claim 1, wherein:
   the method further comprises obtaining a third plurality of at least 10,000 sequence reads comprising the methylation status of cytosine nucleotides, in electronic form, of a DNA sample from the test subject, the DNA sample comprising DNA molecules from a cancerous tissue of the subject;
   determining, based on the third plurality of at least 10,000 sequence reads, a fourth prediction for the homologous recombination pathway status of the cancerous tissue of the subject based on a genomic methylation pattern of the cancerous tissue; and
   the final prediction is further based on the fourth prediction for the homologous recombination pathway status of the cancerous tissue of the subject.

9. The method of claim 8, wherein the first plurality of sequence reads and the third plurality of sequence reads were generated using different aliquots of the same DNA sample comprising the DNA molecules from the cancerous tissue of the subject.

10. The method of claim 8, wherein the genomic methylation pattern of the cancerous tissue comprises a methylation pattern for a promoter region of a homologous recombination gene.

11. The method of claim 8, wherein determining the fourth prediction is further based on a cancer type of the cancerous tissue of the subject.

12. The method of claim 1, wherein:
   the method further comprises obtaining a third plurality of at least 10,000 sequence reads, in electronic form, of a second DNA sample from the test subject, the second DNA sample comprising DNA molecules from a non-cancerous tissue of the subject; and
   determining the first prediction is based on the first plurality of at least 10,000 sequence reads and the third plurality of at least 10,000 sequence reads.

13. The method of claim 1, wherein determining the first prediction is further based on a cancer type of the cancerous tissue of the subject.

14. The method of claim 1, wherein the cancerous tissue of the subject does not have a variant BRCA1 gene and does not have a variant BRCA2 gene.

15. The method of claim 1, wherein the cancerous tissue of the subject has no more than one variant BRCA1 or BRCA2 gene.

16. The method of claim 1, wherein the method further comprises:
   when it is determined that the cancer in the test subject is homologous recombination deficiency (HRD) positive, treating the cancer by administering a poly ADP ribose polymerase (PARP) inhibitor to the test subject; and when it is determined the cancer in the test subject is not homologous recombination deficiency (HRD) positive, treating the cancer with a therapy that does not include administration of a PARP inhibitor to the test subject.

17. The method of claim 1, wherein the method further comprises:

when it is determined that the cancer in the test subject is homologous recombination deficiency (HRD) positive, treating the cancer by administering a platinum-containing neoadjuvant chemotherapy to the test subject; and when it is determined the cancer in the test subject is not homologous recombination deficiency (HRD) positive, treating the cancer with a therapy that does not include administration of a platinum-containing neoadjuvant chemotherapy to the test subject.

18. The method of claim 17, wherein the cancer is a triple-negative breast cancer.

19. A method of obtaining a homologous recombination pathway status of a cancer in a test subject, the method comprising:

at a computer system having one or more processors, and memory storing one or more programs for execution by the one or more processors:

(A) obtaining a first plurality of at least 10,000 sequence reads, in electronic form, of a DNA sample from the test subject, the DNA sample comprising DNA molecules from a cancerous tissue of the subject;

(B) obtaining a second plurality of at least 10,000 sequence reads, in electronic form, of an RNA sample from the test subject, the RNA sample comprising RNA molecules from the cancerous tissue of the subject; and (C) evaluating the first plurality of at least 10,000 sequence reads and the second plurality of at least 10,000 sequence reads using an ensemble model trained to distinguish between cancers with homologous recombination pathway deficiencies and cancers without homologous recombination pathway deficiencies, wherein the evaluating comprises:

determining, based on the first plurality of at least 10,000 sequence reads, a first prediction for the homologous recombination pathway status of the cancerous tissue of the subject based on a measure of genome-wide loss of heterozygosity for the cancerous tissue of the subject;

determining, based on the second plurality of at least 10,000 sequence reads, a second prediction for the homologous recombination pathway status of the cancerous tissue of the subject based on the expression levels of a plurality of genes in the cancerous tissue of the subject;

determining, based on the first plurality of at least 10,000 sequence reads, a third prediction for the homologous recombination pathway status of the cancerous tissue of the subject based on a measure of genome-wide rearrangements for the cancerous tissue of the subject; and determining a final prediction for the homologous recombination pathway status based on the first prediction, the second prediction, and the third prediction, thereby obtaining the homologous recombination pathway status of the test subject as an output of the ensemble model.

20. A method of obtaining a homologous recombination pathway status of a cancer in a test subject, the method comprising:

at a computer system having one or more processors, and memory storing one or more programs for execution by the one or more processors:

(A) obtaining a first plurality of at least 10,000 sequence reads, in electronic form, of a DNA sample from the test subject, the DNA sample comprising DNA molecules from a cancerous tissue of the subject;

(B) obtaining a second plurality of at least 10,000 sequence reads, in electronic form, of an RNA sample from the test subject, the RNA sample comprising RNA molecules from the cancerous tissue of the subject;

(C) obtaining a third plurality of at least 10,000 sequence reads, in electronic form, of a second DNA sample from the test subject, the second DNA sample comprising DNA molecules from a non-cancerous tissue of the subject;

(D) evaluating the first plurality of at least 10,000 sequence reads, the second plurality of at least 10,000 sequence reads, and the third plurality of sequence reads using an ensemble model trained to distinguish between cancers with homologous recombination pathway deficiencies and cancers without homologous recombination pathway deficiencies, wherein the evaluating comprises:

determining, based on the first plurality of at least 10,000 sequence reads and the third plurality of at least 10,000 sequence reads, a first prediction for the homologous recombination pathway status of the cancerous tissue of the subject based on a measure of genome-wide loss of heterozygosity for the cancerous tissue of the subject; and determining, based on the second plurality of at least 10,000 sequence reads, a second prediction for the homologous recombination pathway status of the cancerous tissue of the subject based on the expression levels of a plurality of genes in the cancerous tissue of the subject;

thereby obtaining the homologous recombination pathway status of the test subject.

21. A computer system comprising:

one or more processors; and a non-transitory computer-readable medium including computer-executable instructions that, when executed by the one or more processors, cause the processors to perform a method for obtaining a homologous recombination pathway status of a cancer in a test subject, the method comprising:

(A) obtaining a first plurality of at least 10,000 sequence reads, in electronic form, of a DNA sample from the test subject, the DNA sample comprising DNA molecules from a cancerous tissue of the subject;

(B) obtaining a second plurality of at least 10,000 sequence reads, in electronic form, of an RNA sample from the test subject, the RNA sample comprising RNA molecules from the cancerous tissue of the subject; and (C) evaluating the first plurality of at least 10,000 sequence reads and the second plurality of at least 10,000 sequence reads using an ensemble model trained to distinguish between cancers with homologous recombination pathway deficiencies and cancers without homologous recombination pathway deficiencies, wherein the evaluating comprises:

determining, using the first plurality of at least 10,000 sequence reads, a first prediction for the homologous recombination pathway status of the cancerous tissue of the subject based on a measure of genome-wide loss of heterozygosity for the cancerous tissue of the subject;

determining, using the second plurality of at least 10,000 sequence reads, a second prediction for the homologous recombination pathway status of the cancerous tissue of the subject based on the expression levels of a plurality of genes in the cancerous tissue of the subject;

determining, using the second plurality of at least 10,000 sequence reads, a third prediction for the homologous recombination pathway status of the cancerous tissue of the subject based on a measure of transcriptome-wide rearrangements for the cancerous tissue of the subject; and determining a final prediction for the homologous recombination pathway status based on the first prediction, the second prediction, and the third prediction, thereby obtaining the homologous recombination pathway status of the test subject.

22. A non-transitory computer-readable storage medium having stored thereon program code instructions that, when executed by a processor, cause the processor to perform a method for obtaining a homologous recombination pathway status of a cancer in a test subject, the method comprising:

(A) obtaining a first plurality of at least 10,000 sequence reads, in electronic form, of a DNA sample from the test subject, the DNA sample comprising DNA molecules from a cancerous tissue of the subject;

(B) obtaining a second plurality of at least 10,000 sequence reads, in electronic form, of an RNA sample from the test subject, the RNA sample comprising RNA molecules from the cancerous tissue of the subject; and (C) evaluating the first plurality of at least 10,000 sequence reads and the second plurality of at least 10,000 sequence reads using an ensemble model trained to distinguish between cancers with homologous recombination pathway deficiencies and cancers without homologous recombination pathway deficiencies, wherein the evaluating comprises:

determining, based on the first plurality of at least 10,000 sequence reads, a first prediction for the homologous recombination pathway status of the cancerous tissue of the subject based on a measure of genome-wide loss of heterozygosity for the cancerous tissue of the subject;

determining, based on the second plurality of at least 10,000 sequence reads, a second prediction for the homologous recombination pathway status of the cancerous tissue of the subject based on the expression levels of a plurality of genes in the cancerous tissue of the subject;

determining, based on the first plurality of at least 10,000 sequence reads, a third prediction for the homologous recombination pathway status of the cancerous tissue of the subject based on a measure of genome-wide rearrangements for the cancerous tissue of the subject; and determining a final prediction for the homologous recombination pathway status based on the first prediction, the second prediction, and the third prediction, thereby obtaining the homologous recombination pathway status of the test subject as an output of the ensemble model.

23. A computer system comprising:
one or more processors; and
a non-transitory computer-readable medium including computer-executable instructions that, when executed by the one or more processors, cause the processors to perform a method for obtaining a homologous recombination pathway status of a cancer in a test subject, the method comprising:

(A) obtaining a first plurality of at least 10,000 sequence reads, in electronic form, of a DNA sample from the test subject, the DNA sample comprising DNA molecules from a cancerous tissue of the subject;

(B) obtaining a second plurality of at least 10,000 sequence reads, in electronic form, of an RNA sample from the test subject, the RNA sample comprising RNA molecules from the cancerous tissue of the subject; and (C) evaluating the first plurality of at least 10,000 sequence reads and the second plurality of at least 10,000 sequence reads using an ensemble model trained to distinguish between cancers with homologous recombination pathway deficiencies and cancers without homologous recombination pathway deficiencies, wherein the evaluating comprises:

determining, based on the first plurality of at least 10,000 sequence reads, a first prediction for the homologous recombination pathway status of the cancerous tissue of the subject based on a measure of genome-wide loss of heterozygosity for the cancerous tissue of the subject;

determining, based on the second plurality of at least 10,000 sequence reads, a second prediction for the homologous recombination pathway status of the cancerous tissue of the subject based on the expression levels of a plurality of genes in the cancerous tissue of the subject;

determining, based on the first plurality of at least 10,000 sequence reads, a third prediction for the homologous recombination pathway status of the cancerous tissue of the subject based on a measure of genome-wide rearrangements for the cancerous tissue of the subject; and determining a final prediction for the homologous recombination pathway status based on the first prediction, the second prediction, and the third prediction, thereby obtaining the homologous recombination pathway status of the test subject as an output of the ensemble model.

24. A non-transitory computer-readable storage medium having stored thereon program code instructions that, when executed by a processor, cause the processor to perform a method for obtaining a homologous recombination pathway status of a cancer in a test subject, the method comprising:

(A) obtaining a first plurality of at least 10,000 sequence reads, in electronic form, of a DNA sample from the test subject, the DNA sample comprising DNA molecules from a cancerous tissue of the subject;

(B) obtaining a second plurality of at least 10,000 sequence reads, in electronic form, of an RNA sample from the test subject, the RNA sample comprising RNA molecules from the cancerous tissue of the subject; and (C) evaluating the first plurality of at least 10,000 sequence reads and the second plurality of at least 10,000 sequence reads using an ensemble model trained to distinguish between cancers with homologous recombination pathway deficiencies and cancers without homologous recombination pathway deficiencies, wherein the evaluating comprises:
  determining, based on the first plurality of at least 10,000 sequence reads, a first prediction for the homologous recombination pathway status of the cancerous tissue of the subject based on a measure of genome-wide loss of heterozygosity for the cancerous tissue of the subject;
  determining, based on the second plurality of at least 10,000 sequence reads, a second prediction for the homologous recombination pathway status of the cancerous tissue of the subject based on the expression levels of a plurality of genes in the cancerous tissue of the subject;
  determining, based on the first plurality of at least 10,000 sequence reads, a third prediction for the homologous recombination pathway status of the cancerous tissue of the subject based on a measure of genome-wide rearrangements for the cancerous tissue of the subject; and
  determining a final prediction for the homologous recombination pathway status based on the first prediction, the second prediction, and the third prediction,
thereby obtaining the homologous recombination pathway status of the test subject as an output of the ensemble model.

25. A computer system comprising:
one or more processors; and
a non-transitory computer-readable medium including computer-executable instructions that, when executed by the one or more processors, cause the processors to perform a method for obtaining a homologous recombination pathway status of a cancer in a test subject, the method comprising:
(A) obtaining a first plurality of at least 10,000 sequence reads, in electronic form, of a DNA sample from the test subject, the DNA sample comprising DNA molecules from a cancerous tissue of the subject;
(B) obtaining a second plurality of at least 10,000 sequence reads, in electronic form, of an RNA sample from the test subject, the RNA sample comprising RNA molecules from the cancerous tissue of the subject;
(C) obtaining a third plurality of at least 10,000 sequence reads, in electronic form, of a second DNA sample from the test subject, the second DNA sample comprising DNA molecules from a non-cancerous tissue of the subject;
(D) evaluating the first plurality of at least 10,000 sequence reads, the second plurality of at least 10,000 sequence reads, and the third plurality of sequence reads using an ensemble model trained to distinguish between cancers with homologous recombination pathway deficiencies and cancers without homologous recombination pathway deficiencies, wherein the evaluating comprises:
  determining, based on the first plurality of at least 10,000 sequence reads and the third plurality of at least 10,000 sequence reads, a first prediction for the homologous recombination pathway status of the cancerous tissue of the subject based on a measure of genome-wide loss of heterozygosity for the cancerous tissue of the subject; and
  determining, based on the second plurality of at least 10,000 sequence reads, a second prediction for the homologous recombination pathway status of the cancerous tissue of the subject based on the expression levels of a plurality of genes in the cancerous tissue of the subject;
thereby obtaining the homologous recombination pathway status of the test subject.

26. A non-transitory computer-readable storage medium having stored thereon program code instructions that, when executed by a processor, cause the processor to perform a method for obtaining a homologous recombination pathway status of a cancer in a test subject, the method comprising:
(A) obtaining a first plurality of at least 10,000 sequence reads, in electronic form, of a DNA sample from the test subject, the DNA sample comprising DNA molecules from a cancerous tissue of the subject;
(B) obtaining a second plurality of at least 10,000 sequence reads, in electronic form, of an RNA sample from the test subject, the RNA sample comprising RNA molecules from the cancerous tissue of the subject;
(C) obtaining a third plurality of at least 10,000 sequence reads, in electronic form, of a second DNA sample from the test subject, the second DNA sample comprising DNA molecules from a non-cancerous tissue of the subject;
(D) evaluating the first plurality of at least 10,000 sequence reads, the second plurality of at least 10,000 sequence reads, and the third plurality of sequence reads using an ensemble model trained to distinguish between cancers with homologous recombination pathway deficiencies and cancers without homologous recombination pathway deficiencies, wherein the evaluating comprises:
  determining, based on the first plurality of at least 10,000 sequence reads and the third plurality of at least 10,000 sequence reads, a first prediction for the homologous recombination pathway status of the cancerous tissue of the subject based on a measure of genome-wide loss of heterozygosity for the cancerous tissue of the subject; and
  determining, based on the second plurality of at least 10,000 sequence reads, a second prediction for the homologous recombination pathway status of the cancerous tissue of the subject based on the expression levels of a plurality of genes in the cancerous tissue of the subject;
thereby obtaining the homologous recombination pathway status of the test subject.

* * * * *